United States Patent
McClain et al.

(10) Patent No.: US 12,157,766 B2
(45) Date of Patent: Dec. 3, 2024

(54) CYTOPLASMIC EXPRESSION SYSTEM

(71) Applicant: ABSCI CORPORATION, Vancouver, WA (US)

(72) Inventors: Sean McClain, Vancouver, WA (US); Philip Barish, Vancouver, WA (US)

(73) Assignee: ABSCI CORPORATION, Vancouver, WA (US)

( * ) Notice: Subject to any disclaimer, the term of this patent is extended or adjusted under 35 U.S.C. 154(b) by 768 days.

(21) Appl. No.: 16/009,147

(22) Filed: Jun. 14, 2018

(65) Prior Publication Data
US 2018/0282405 A1    Oct. 4, 2018

Related U.S. Application Data

(63) Continuation of application No. PCT/US2016/067064, filed on Dec. 15, 2016, and a continuation-in-part of application No. 14/952,535, filed on Nov. 25, 2015, now Pat. No. 10,465,197, which is a continuation of application No. 14/419,653, filed as application No. PCT/US2013/053562 on Aug. 5, 2013, now Pat. No. 9,617,335.

(60) Provisional application No. 62/267,898, filed on Dec. 15, 2015, provisional application No. 61/747,246, filed on Dec. 29, 2012, provisional application No. 61/679,751, filed on Aug. 5, 2012.

(51) Int. Cl.
| | |
|---|---|
| *C12N 15/70* | (2006.01) |
| *C07K 16/00* | (2006.01) |
| *C07K 16/24* | (2006.01) |
| *C07K 16/28* | (2006.01) |
| *C07K 14/62* | (2006.01) |

(52) U.S. Cl.
CPC ............ *C07K 16/241* (2013.01); *C07K 16/00* (2013.01); *C07K 16/2803* (2013.01); *C12N 15/70* (2013.01); *C07K 14/62* (2013.01); *C07K 2317/14* (2013.01); *C07K 2317/21* (2013.01); *C07K 2317/24* (2013.01); *C07K 2317/92* (2013.01)

(58) Field of Classification Search
CPC ............ C07K 2317/14; C07K 2317/21; C07K 2317/24; C07K 2317/92; C07K 16/241; C07K 16/00; C07K 16/2803; C07K 14/62; C12N 15/70
See application file for complete search history.

(56) References Cited

U.S. PATENT DOCUMENTS

| | | | | |
|---|---|---|---|---|
| 6,083,715 A | * | 7/2000 | Georgiou | ............ C07K 14/4743 435/252.1 |
| 6,803,210 B2 | * | 10/2004 | Better | ............ C12N 15/635 435/69.1 |
| 6,872,563 B1 | | 3/2005 | Beckwith | |
| 7,816,117 B2 | | 10/2010 | Beckwith | |
| 8,178,338 B2 | | 5/2012 | Keasling | |
| 9,238,817 B2 | | 1/2016 | Ruddock | |
| 9,416,388 B2 | | 8/2016 | Ruddock | |
| 11,214,807 B2 | * | 1/2022 | McClain | ............ C12P 21/02 |
| 2002/0156234 A1 | * | 10/2002 | Rubroder | ............ A61P 3/10 530/305 |
| 2003/0104981 A1 | | 6/2003 | Mandic | |
| 2011/0117625 A1 | | 5/2011 | Lippow et al. | |
| 2013/0244925 A1 | | 9/2013 | Nur et al. | |
| 2015/0353940 A1 | | 12/2015 | McClain et al. | |
| 2020/0032276 A1 | * | 1/2020 | McClain | ............ C12N 15/70 |

FOREIGN PATENT DOCUMENTS

| | | |
|---|---|---|
| EP | 2386641 | 11/2011 |
| WO | WO 2006/133210 | 12/2006 |

OTHER PUBLICATIONS

Lobstein, J. et al. (2012). SHuffle, a novel *Escherichia coli* protein expression strain capable of correctly folding disulfide bonded proteins in its cytoplasm. Microbial cell factories, 11, 56, pp. 1-16 and Supplemental Materials. (Year: 2012).*

Jeong, K. J., & Lee, S. Y. (1999). High-level production of human leptin by fed-batch cultivation of recombinant *Escherichia coli* and its purification. Applied and environmental microbiology, 65(7), 3027-3032. (Year: 1999).*

Choi, J. H., Keum, K. C., & Lee, S. Y. (2006). Production of recombinant proteins by high cell density culture of *Escherichia coli*. Chemical engineering science, 61(3), 876-885. (Year: 2006).*

Kim, S. S., Kim, E. K., & Rhee, J. S. (1996). Effects of growth rate on the production of Pseudomonas fluorescens lipase during the fed-batch cultivation of *Escherichia coli*. Biotechnology progress, 12(5), 718-722. (Year: 1996).*

Vinther, T. N., Pettersson, I., Huus, K., Schlein, M., Steensgaard, D. B., Sørensen, A., . . . & Hubalek, F. (2015). Additional disulfide bonds in insulin: Prediction, recombinant expression, receptor binding affinity, and stability. Protein Science, 24(5), 779-788. (Year: 2015).*

(Continued)

Primary Examiner — Nancy J Leith
Assistant Examiner — Khaleda B Hasan
(74) Attorney, Agent, or Firm — MARSHALL, GERSTEIN & BORUN LLP

(57) ABSTRACT

The present invention provides host cells having an oxidizing cytoplasm, which are capable of growing to high cell densities and producing recombinant proteins in soluble form. Also provided are methods for growing such host cells to high densities, methods for optionally modulating the growth rates of the host cells, and methods for inducing the host cells to produce the desired gene product in soluble form. Further aspects of the invention relate to host cell preparation and storage methods, which utilize the advantages of producing gene products in host cell cytoplasm to provide methods for long-term storage and/or transport of expressed gene products that are retained in a stable and soluble form within the host cells.

23 Claims, 6 Drawing Sheets
Specification includes a Sequence Listing.

(56) References Cited

OTHER PUBLICATIONS

Bao et al., "Direct over-expression, characterization and H2O2 stability study of active Pleurotus eryngii versatile peroxidase in *Escherichia coli*," *Biotechnol Lett* vol. 34, No. 8, pp. 1537-1543, 2012.
Canadian IP Office, Examination Report in CA Application No. 2880285; Jan. 15, 2019.
CIPO, Office Action in CN Application No. 201380041522X, English Translation; May 10, 2019.
CIPO, Office Action in CN Application No. 201380041522X; May 10, 2019.
EMBL Protein Expression and Purification Facility, "Expression in *Escherichia coli*," Sep. 11, 2001 https://www.embl.de/pepcore/pepcore_services/protein_expression/ecoli/, retrieved Nov. 10, 2015.
European Patent Office, Search Opinion in EP Application No. 16201998; May 3, 2017.
Faulkner et al., "Functional plasticity of a peroxidase allows evolution of diverse disulfide-reducing pathways," *Proc Natl Acad Sci*, vol. 105, No. 18, pp. 6735-6740, 2008.
Guzman et al., Tight regulation, modulation, and high-level expression by vectors containing the arabinose PBAD promoter, vol. 177, No. 14, pp. 4121-4130, 1995.
IP Australia, Examination Report in AU Application No. 2013299910; Mar. 28, 2018.
Japan Patent Office, First Notification of Reasons for Refusal in JP Application No. 2015526598; Jun. 22, 2017.
Japan Patent Office, Second Notification of Reasons for Refusal in JP Application No. 2015526598; Jan. 30, 2018.
Khlebnikov et al., "Regulatable arabinose-inducible gene expression system with consistent control in all cells of a culture," *J Bacteriol*, vol. 182, No. 24, pp. 7029-7034, 2000.
Khlebnikov, "Homogeneous expression of the P(BAD) promoter in *Escherichia coli* by constitutive expression of the low-affinity high-capacity AraE transporter," *Microbiology*, vol. 147(Pt 12), pp. 3241-3247, 2001.
Lee and Keasling, "A propionate-inducible expression system for enteric bacteria," *Appl Environ Microbiol*, vol. 71, No. 11, pp. 6856-6862, 2005.
Levy et al., "Production of correctly folded Fab antibody fragment in the cytoplasm of *Escherichia coli* trxB gor mutants via the coexpression of molecular chaperones," *Protein Expr Purif*, vol. 23, No. 2, pp. 338-347, 2001.
Lobstein et al., "SHuffle, a novel *Escherichia coli* protein expression strain capable of correctly folding disulfide bonded proteins in its cytoplasm," *Microbial Cell Factories*, vol. 11, No. 56, pp. 1-16. 2012.
Mayer, "A new set of useful cloning and expression vectors derived from pBlueScript," *Gene*, vol. 163, No. 1, pp. 41-46, 1995.
Ollis et al., "Cytoplasmic membrane proton motive force energizes periplasmic interactions between ExbD and TonB," *Mol Microbiol*, vol. 73, No. 3, pp. 466-481, 2009.
Qiu et al., "Expression of active human tissue-type plasminogen activator in *Escherichia coli*," *Appl Environ Microbiol*, vol. 64, No. 12, pp. 4891-4896, 1998.
Sorensen and Mortensen, "Advanced genetic strategies for recombinant protein expression in *Escherichia coli*," *J Biotechnol*, vol. 115, No. 2, pp. 113-128, 2005.
Samuelson et al., "Recent developments in difficult protein expression: a guide to *E. coli* strains, promoters, and relevant host mutations," *Methods Mol Biol*, vol. 705, pp. 195-209, 2011.
Stancombe et al., "Engineering botulinum neurotoxin domains for activation by toxin light chain," *FEBS J*, vol. 279, No. 3, pp. 515-523, 2012.
Terpe, "Overview of bacterial expression systems for heterologous protein production: from molecular and biochemical fundamentals to commercial systems," *Appl Microbial Biotechnol*, vol. 72, No. 2, pp. 211-222, 2006.
USPTO, Final Office Action in U.S. Appl. No. 14/909,707; filed Nov. 8, 2018.
USPTO, Non-Final Office Action in U.S. Appl. No. 14/909,707; filed Apr. 26, 2018.
Varsani et al., "Arthrobacter D-xylose isomerase: protein-engineered subunit interfaces," *Biochem J*, vol. 291 (Pt 2), pp. 575-583, 1993.
Makino et al., Comprehensive engineering of *Escherichia coli* for enhanced expression of IgG antibodies, Metab Eng., 13(2): 241-251 (Mar. 2011).

* cited by examiner

CYTOPLASMIC EXPRESSION SYSTEM

REFERENCE TO RELATED APPLICATIONS

This application (1) is a continuation of International Application No. PCT/US2016/067064 filed 15 Dec. 2016, which claims the benefit of priority of U.S. Provisional Application No. 62/267,898, filed on 15 Dec. 2015; and (2) is a continuation-in-part of U.S. application Ser. No. 14/952,535, filed on 25 Nov. 2015, which is a continuation of U.S. application Ser. No. 14/419,653, which is a national-stage entry under 35 U.S.C. § 371 of International Application No. PCT/US2013/053562 filed 5 Aug. 2013, which claims the benefit of priority of U.S. Provisional Application No. 61/679,751, filed 5 Aug. 2012, and of U.S. Provisional Application No. 61/747,246, filed 29 Dec. 2012;

the entire disclosures of all of which are incorporated by reference herein.

REFERENCE TO THE SEQUENCE LISTING

This application includes a sequence listing submitted electronically, in a file entitled "AbSci-002PCT_ST25.txt", created on Dec. 15, 2016 and having a size of 23,774 bytes, which is incorporated by reference herein.

FIELD OF THE INVENTION

The present invention is in the general technical fields of molecular biology and biotechnological manufacturing. More particularly, the present invention is in the technical field of recombinant protein expression.

BACKGROUND OF THE INVENTION

Many proteins of commercial value, such as antibodies, antibody fragments, insulin, granulocyte colony-stimulating factor, tissue-type plasminogen activator, etc., contain at least one disulfide bond formed between the sulfur atoms of cysteine amino acids. Disulfide bonds form more readily in an oxidizing environment, in which the sulfur atoms participating in a disulfide bond are less likely to be reduced to form sulfhydryl groups, which would eliminate the disulfide bond. An oxidizing environment can be found within certain subcellular compartments of cells, such as the secretory pathway and certain topologically 'extracellular' compartments of eukaryotic cells (Go and Jones, "Redox compartmentalization in eukaryotic cells", Biochim Biophys Acta 2008 November; 1780(11): 1273-1290; doi: 10.1016/j.bbagen.2008.01.011; Epub 2008 Jan. 26; Review), and the periplasm of bacteria such as *E. coli*. The cell cytoplasm is normally maintained in a relatively reduced state by the thioredoxin and the glutaredoxin/glutathione enzyme systems. This generally inhibits the formation of disulfide bonds in the cytoplasm, and most proteins that need disulfide bonds to function are exported into the eukaryotic secretory pathway or the bacterial periplasm where disulfide bond formation can readily occur.

Expression of recombinant proteins in the cytoplasm of microorganisms such as *E. coli* has been investigated as a method for efficient protein production that is less expensive than use of mammalian cell systems. Since many of the most commercially valuable therapeutic proteins contain disulfide bonds, the bacterial cytoplasm has, through genetic manipulation of the host cell, been made more oxidizing so that heterologous proteins produced in the bacterial cytoplasm would be more likely to form disulfide bonds and be correctly folded. This approach has met with mixed success in small-volume protein expression experiments (Lobstein et al., "SHuffle, a novel *Escherichia coli* protein expression strain capable of correctly folding disulfide bonded proteins in its cytoplasm", Microb Cell Fact 2012 May 8; 11:56; doi: 10.1186/1475-2859-11-56), where many proteins, especially those with multiple disulfide bonds, have been produced predominantly in an insoluble form.

Growth of host cells with oxidizing cytoplasm to high cell density using fermentation methods, or "oxidizing cytoplasmic fermentation", has previously proved to be unsuccessful for commercial protein production. In most reported examples, the host cells are not capable of growing to high density (Neubauer et al., "Fermentation process for tetrameric human collagen prolyl 4-hydroxylase in *Escherichia coli*: improvement by gene optimisation of the PDI/beta subunit and repeated addition of the inducer anhydrotetracycline", J Biotechnol. 2007 Feb. 1; 128(2): 308-321; Epub 2006 Nov. 7). When oxidized cytoplasmic fermentation has been achieved at higher cell densities, the proteins produced have formed insoluble inclusion bodies (Chung et al., "Recombinant production of biologically active giant grouper (*Epinephelus lanceolatus*) growth hormone from inclusion bodies of *Escherichia coli* by fed-batch culture", Protein Expr Purif 2015 June; 110: 79-88; doi: 10.1016/j.pep.2015.02.012; Epub 2015 Feb. 19). A method utilizing the advantages of protein production in an oxidizing cytoplasm, efficiently producing soluble and active proteins—that is, proteins that are properly folded and in which any disulfide bonds are correctly formed—in a manner that is capable of scaling up to commercial production levels, is clearly needed.

SUMMARY OF THE INVENTION

The present invention provides host cells having an altered gene function of at least one gene that makes the reduction/oxidation environment of the host cell cytoplasm more oxidizing, which are capable of growing to high cell densities and producing recombinant proteins in soluble form. Also provided are methods for growing such host cells to high densities, for optionally modulating the growth rates of the host cells, and for inducing the host cells to produce the desired gene product in soluble form. Further aspects of the invention relate to host cell preparation and storage methods, which utilize the advantages of producing gene products in host cell cytoplasm to provide methods for long-term storage and/or transport of expressed gene products retained in a stable and soluble form within the host cells.

In one set of embodiments of the invention, Method I is a method of producing at least one gene product; Method I comprises a set of combinations of steps A-F, as described below. Method I can be symbolized by the following schema:

Method I{A[1-8], B[1-3], C[1]$_{0-1}$, D[1-3]$_{0-1}$, E[1-2]$_{0-1}$, F[1]$_{0-1}$} wherein A-F represent steps of Method I. A subscript of 0-1 indicates that a step can be present or absent in Method I, and if present, with no limitation on the number of times the step can be performed. A letter followed by bracketed numbers, for example A[1-3], indicates that step A has attributes A1, A2, and A3, and step A can optionally include any combination of attributes A1, A2, and/or A3. Each attribute, such as A1 for example, may have a number of alternative instances, such as A1.1, A1.2, and A1.3 for example. Alternative instances such as A1.1 can be presented as a list wherein every member of the list is an alternative instance of A1 and can therefore be combined with any instance of any other attributes of step A, and/or with any other instances and/or attribute(s) of any other step of Method I.

The following paragraphs set forth the steps A-F of Method I, along with any attributes of each step and any alternative instances of each attribute.

Step A of Method I: Providing One or More Host Cells.

A1: providing host cells comprising at least one expression construct.

A1.1: providing host cells comprising at least one expression construct comprising a polynucleotide sequence selected from the group consisting of: pSOL (SEQ ID NO:3) or fragments thereof.

A.1.2: providing host cells comprising at least two expression constructs.

A2: providing host cells comprising at least one expression construct comprising at least one inducible promoter.

A2.1: providing host cells comprising at least one expression construct comprising at least one inducible promoter, wherein the inducible promoter is not a lactose-inducible promoter.

A2.2: providing host cells comprising at least one expression construct comprising at least one inducible promoter, wherein the inducible promoter is selected from the group consisting of an L-arabinose-inducible promoter, a propionate-inducible promoter, a rhamnose-inducible promoter, a xylose-inducible promoter, a lactose-inducible promoter, and a promoter inducible by phosphate depletion.

A2.3: providing host cells comprising at least one expression construct comprising at least one inducible promoter, wherein the inducible promoter is selected from the group consisting of the araBAD promoter, the prpBCDE promoter, the rhaSR promoter, the xlyA promoter, the lacZYA promoter, and the phoA promoter.

A3: providing host cells comprising at least one expression construct comprising at least one inducible promoter and at least one polynucleotide sequence encoding a gene product to be transcribed from at least one said inducible promoter.

A3.1: providing host cells comprising at least one expression construct comprising at least one inducible promoter and at least one polynucleotide sequence encoding a gene product to be transcribed from at least one said inducible promoter, wherein the gene product lacks a signal sequence.

A3.2: providing host cells comprising at least one expression construct comprising at least one inducible promoter and at least one polynucleotide sequence encoding a gene product to be transcribed from at least one said inducible promoter, wherein the gene product further comprises a tag selected from the group consisting of: polyhistidine, pestivirus N$^{pro}$, CSFV N$^{pro}$, CSFV N$^{pro}$ (strain Alfort), BDV N$^{pro}$, BVDV N$^{pro}$, SEQ ID NO:13, SEQ ID NO:14, SEQ ID NO:15, and fragments thereof.

A3.3: providing host cells comprising at least one expression construct comprising at least one inducible promoter and at least one polynucleotide sequence encoding a gene product to be transcribed from at least one said inducible promoter, wherein the gene product forms a number of disulfide bonds selected from the group consisting of: at least one and fewer than twenty disulfide bonds; at least two and fewer than seventeen disulfide bonds; at least eighteen and fewer than one hundred disulfide bonds; at least three and fewer than ten disulfide bonds; at least three and fewer than eight disulfide bonds; one disulfide bond; two disulfide bonds; three disulfide bonds; four disulfide bonds; five disulfide bonds; six disulfide bonds; seven disulfide bonds; eight disulfide bonds; and nine disulfide bonds.

A3.4: providing host cells comprising at least one expression construct comprising at least one inducible promoter and at least one polynucleotide sequence encoding a gene product to be transcribed from at least one said inducible promoter, wherein the gene product is an insulin polypeptide comprising an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and fragments thereof.

A3.5: providing host cells comprising at least one expression construct comprising at least one inducible promoter and at least one polynucleotide sequence encoding a gene product to be transcribed from at least one said inducible promoter, wherein the gene product is selected from the group consisting of: an immunoglobulin heavy chain, an immunoglobulin light chain, and fragments thereof.

A3.6: providing host cells comprising at least one expression construct comprising at least one inducible promoter and at least one polynucleotide sequence encoding a gene product to be transcribed from at least one said inducible promoter, wherein the gene product is selected from the group consisting of: 1-antitrypsin; 2C4; activin; addressins; alkaline phosphatase; anti-CD11a; anti-CD18; anti-CD20; anti-clotting factors such as Protein C; anti-HER-2 antibody; anti-IgE; anti-IgG; anti-VEGF; antibodies and antibody fragments; antibodies to ErbB2 domain(s) such as 2C4 (WO 01/00245 hybridoma ATCC HB-12697), which binds to a region in the extracellular domain of ErbB2 (e.g., any one or more residues in the region from about residue 22 to about residue 584 of ErbB2, inclusive); Apo2 ligand (Apo2L); atrial naturietic factor; BDNF; beta-lactamase; bombesin; bone morphogenetic protein (BMP); brain IGF-I; calcitonin; cardiotrophins (cardiac hypertrophy factor) such as cardiotrophin-1 (CT-1); CD proteins such as CD-3, CD-4, CD-8, and CD-19; clotting factors such as factor VIIIC, factor IX, tissue factor, and von Willebrands factor; colony stimulating factors (CSFs), e.g., M-CSF, GM-CSF, and G-CSF; decay-accelerating factor; des(1-3)-IGF-I (brain IGF-I); DNase; enkephalinase; epidermal growth factor (EGF); erythropoietin; fibroblast growth factor such as aFGF and bFGF; follicle-stimulating hormone; glucagon; gp120; growth hormone, including human growth hormone or bovine growth hormone; growth-hormone releasing factor; hemopoietic growth factor; homing receptors; HSA; IGF-I; IGF-II; immunotoxins; inhibin; insulin chains (insulin A-chain, insulin B-chain) or proinsulin; insulin-like growth factor binding proteins; insulin-like growth factor-I and -II (IGF-I and IGF-II); integrin; interferon such as interferon-alpha, -beta, and -gamma; interleukins (ILs), e.g., IL-1 to IL-10; lipoproteins; lung surfactant; luteinizing hormone; mouse gonadotropin-associated peptide; mullerian-inhibiting substance; nerve growth factor (NGF); neurotrophic factor such as brain-derived neurotrophic factor (BDNF), neurotrophin-3, -4, -5, or -6 (NT-3, NT-4, NT-5, or NT-6); osteoinductive factors; parathyroid hormone; plasminogen activator, such as urokinase or human urine or tissue-type plasminogen activator (t-PA); platelet-derived growth factor (PDGF); prorelaxin; protein A or D; receptors for hormones or growth factors; regulatory proteins; relaxin A-chain; relaxin B-chain; rennin; rheumatoid factors; serum albumin, such as human serum albumin (HSA) or bovine serum albumin (BSA); superoxide dismutase; surface-membrane proteins; T-cell receptors; TGF-beta; thrombin; thrombopoietin; thyroid-stimulating hormone; transforming growth factor (TGF) such as TGF-alpha and TGF-beta, including TGF-1, TGF-2, TGF-3, TGF-4, or TGF-5; transport proteins; tumor necrosis factor-alpha and -beta; urokinase; vascular endothelial growth factor (VEGF); viral antigens such as, for example, a portion of the AIDS envelope; and fragments of any of the above-listed polypeptides.

A4: providing host cells having an altered gene function of at least one gene that affects the reduction/oxidation environment of the host cell cytoplasm.
  A4.1: providing host cells having an altered gene function of at least one gene that increases the oxidizing environment of the host cell cytoplasm.
  A4.2: providing host cells having an altered gene function of at least one gene that increases the oxidizing environment of the host cell cytoplasm selected from the group consisting of gor, gshA, gshB, and trxB.
  A4.3: providing host cells having an altered gene function of at least one gene selected from the group consisting of ahpC, katG, and katE.
  A4.4: providing host cells having an ahpC$^\Delta$ gene.
A5: providing host cells having a reduced level of gene function of at least one gene encoding a protein that metabolizes an inducer of at least one inducible promoter.
  A5.1: providing host cells having a reduced level of gene function of at least one gene encoding a protein that metabolizes an inducer of at least one inducible promoter, wherein the gene is selected from the group consisting of araA, araB, araD, prpB, prpD, rhaA, rhaB, rhaD, xylA, and xylB.
A6: providing host cells having an altered level of gene function of at least one gene encoding a transporter protein for an inducer of at least one inducible promoter.
  A6.1: providing host cells having an altered level of gene function of at least one gene encoding a transporter protein for an inducer of at least one inducible promoter, wherein the gene is selected from the group consisting of araE, araF, araG, araH, rhaT, xylF, xylG, and xylH.
  A6.2: providing host cells having an altered level of gene function of at least one gene encoding a transporter protein for an inducer of at least one inducible promoter, wherein the altered gene function is expressing the transporter protein from a constitutive promoter.
A7: providing host cells further comprising a polynucleotide encoding a polypeptide selected from the group consisting of: cDsbA, cDsbC, a protein disulfide isomerase, Erv1p, a chaperone, and a transporter protein for a cofactor of the gene product to be transcribed from at least one inducible promoter.
A8: providing host cells wherein the host cells are prokaryotic cells.
  A8.1: providing host cells wherein the host cells are $E. coli$ cells.
  A8.2: providing host cells wherein the host cells are $E. coli$ B strain cells.
  A8.3: providing host cells wherein the host cells are $E. coli$ EB0001 cells.
  A8.3: providing host cells wherein the host cells are $E. coli$ EB0002 cells.

Step B of Method I: Growing the Host Cells.
  B1: growing the host cells until the host cells reach a density greater than 50 ($OD_{600}$).
    B1.1: growing the host cells until the host cells reach a density greater than a cell density selected from the group consisting of: 60 ($OD_{600}$); 70 ($OD_{600}$); 80 ($OD_{600}$); 90 ($OD_{600}$); 95 ($OD_{600}$); 100 ($OD_{600}$); 105 ($OD_{600}$); 110 ($OD_{600}$); 115 ($OD_{600}$); 120 ($OD_{600}$); 125 ($OD_{600}$); 130 ($OD_{600}$); 135 ($OD_{600}$); 140 ($OD_{600}$); 145 ($OD_{600}$); 150 ($OD_{600}$); 155 ($OD_{600}$); 160 ($OD_{600}$); 165 ($OD_{600}$); 170 ($OD_{600}$); and 175 ($OD_{600}$).
  B2: growing the host cells at a specific cell growth rate between 0.01 and 0.2.
    B2.1: growing the host cells at a specific cell growth rate selected from the group consisting of: 0.01 to 0.7; 0.05 to 0.3; 0.1 to 0.2; approximately 0.15 (0.15 plus-or-minus 10%); and 0.15.
  B3: growing the host cells in a fermentation volume between 0.1 L and 1,000,000 L.
    B3.1: growing the host cells in a fermentation volume selected from the group consisting of: 0.1 L, 0.25 L, 0.5 L; 0.6 L; 0.75 L; 0.8 L; 1 L; 2 L; 3 L; 4 L; 5 L; 7.5 L; 10 L; 15 L; 20 L; 25 L; 30 L; 40 L; 50 L; 60 L; 70 L; 80 L; 90 L; 100 L; 200 L; 250 L; 300 L; 500 L; 750 L; 1000 L; 1500 L; 2000 L; 2500 L; 3000 L; 5000 L; 7500 L; 10,000 L; 15,000 L; 20,000 L; 25,000 L; 50,000 L; 75,000 L; 100,000 L; greater than 100,000 L and less than 1,000,000 L, and 1,000,000 L.

Step C of Method I: Adding at Least One Inducer to the Host Cells.
  C1: adding at least one inducer to the host cells per host cell density ($OD_{600}$) unit.
    C1.1: adding at least one inducer to the host cells per host cell density ($OD_{600}$) unit, wherein the inducer is selected from the group consisting of: L-arabinose at a concentration between 200 micromolar and 1 pM; L-arabinose at a concentration between 100 micromolar and 1 nM; L-arabinose at a concentration between 50 micromolar and 100 nM; L-arabinose at a concentration between 50 micromolar and 1 micromolar; L-rhamnose at a concentration between 1 M and 1 pM; L-rhamnose at a concentration between 1 mM and 1 nM; D-xylose at a concentration between 1 M and 1 pM; D-xylose at a concentration between 1 mM and 1 nM; propionate at a concentration between 1 M and 1 nM; propionate at a concentration between 1 mM and 1 nM.

Step D of Method I: Collecting the Host Cells and Storing them.
  D1: collecting the host cells by centrifugation.
  D2: collecting the host cells and storing them at a temperature of less than 0 degrees C.
  D3: collecting the host cells and storing them for a period longer than 24 hours.

Step E of Method I: Lysing the Host Cells.
  E1: lysing the host cells by chemical lysis.
    E1.1: lysing the host cells using lysozyme.

E2: lysing the host cells by mechanical disruption.
E2.1: lysing the host cells with a microfluidizer.
Step F of Method I: Purifying the Gene Product.
F1: purifying gene product from the soluble cell lysate fraction.
F1.1: purifying active gene product from the soluble cell lysate fraction.
F1.2: purifying gene product from the soluble cell lysate fraction, wherein the gene product contains properly formed disulfide bonds.

The present invention has been described in terms of several embodiments solely for the purpose of illustration. Persons skilled in the art will recognize from this description that the invention is not limited to the embodiments described, and may be practiced with modifications and alterations.

DETAILED DESCRIPTION OF THE INVENTION

Figure 1:
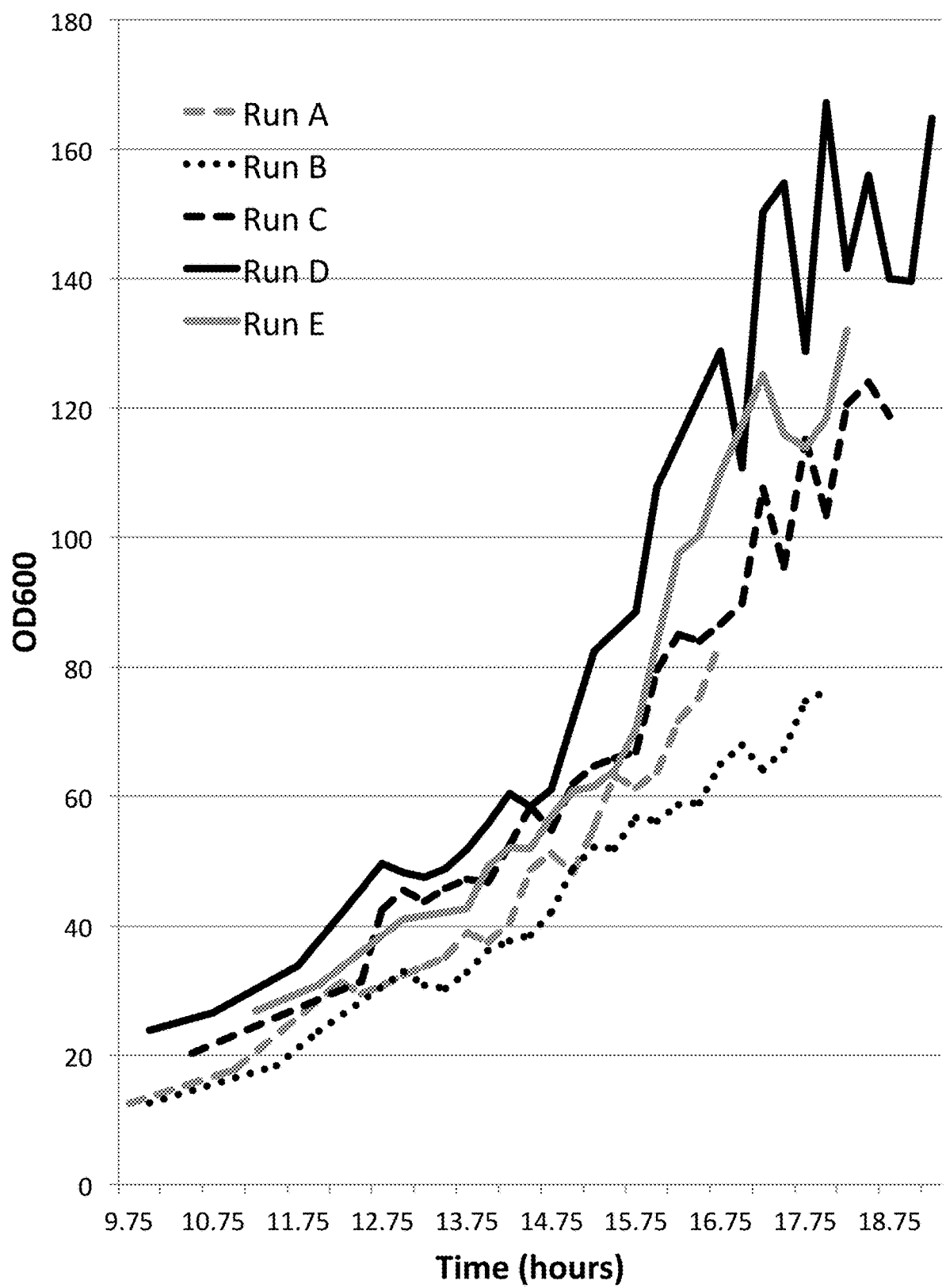
FIG. 1 shows the growth of *E. coli* EB0001(pBAD24-Infliximab_HC/pPRO33-Infliximab_LC) cells over time, measured as $OD_{600}$, in five fermentation runs performed under different conditions. The cells in Run D reached an $OD_{600}$ of 167.2 at 18.25 hours.

The problem of producing gene products such as therapeutic proteins at commercial scale and in soluble form is addressed by providing suitable host cells capable of growth at high cell density in fermentation culture, and which can produce soluble gene products in the oxidizing host cell cytoplasm through highly controlled inducible gene expression. Host cells of the invention with these qualities are produced by combining some or all of the following characteristics. (1) The host cells are genetically modified to have an oxidizing cytoplasm, through increasing the expression or function of oxidizing polypeptides in the cytoplasm, and/or by decreasing the expression or function of reducing polypeptides in the cytoplasm. Specific examples of such genetic alterations are provided herein. Optionally, host cells can also be genetically modified to express chaperones and/or cofactors that assist in the production of the desired gene product(s), and/or to glycosylate polypeptide gene products. (2) The host cells comprise one or more expression constructs designed for the expression of one or more gene products of interest; in certain embodiments, at least one expression construct comprises an inducible promoter and a polynucleotide encoding a gene product to be expressed from the inducible promoter. (3) The host cells contain additional genetic modifications designed to improve certain aspects of gene product expression from the expression construct(s). In particular embodiments, the host cells (A) have an alteration of gene function of at least one gene encoding a transporter protein for an inducer of at least one inducible promoter, and as another example, wherein the gene encoding the transporter protein is selected from the group consisting of araE, araF, araG, araH, rhaT, xylF, xylG, and xylH, or particularly is araE, or wherein the alteration of gene function more particularly is expression of araE from a constitutive promoter; and/or (B) have a reduced level of gene function of at least one gene encoding a protein that metabolizes an inducer of at least one inducible promoter, and as further examples, wherein the gene encoding a protein that metabolizes an inducer of at least one said inducible promoter is selected from the group consisting of araA, araB, araD, prpB, prpD, rhaA, rhaB, rhaD, xylA, and xylB; and/or (C) have a reduced level of gene function of at least one gene encoding a protein involved in biosynthesis of an inducer of at least one inducible promoter, which gene in further embodiments is selected from the group consisting of scpA/sbm, argK/ygfD, scpB/ygfG, scpC/ygfH, rmlA, rmlB, rmlC, and rmlD.

Host Cells with Oxidizing Cytoplasm.

The expression systems of the invention are designed to express gene products; in certain embodiments of the invention, the gene products are expressed in a host cell. Examples of host cells are provided that allow for the efficient and cost-effective expression of gene products, including components of multimeric products. Host cells can include, in addition to isolated cells in culture, cells that are part of a multicellular organism, or cells grown within a different organism or system of organisms. In certain embodiments of the invention, the host cells are microbial cells such as yeasts (*Saccharomyces, Schizosaccharomyces*, etc.) or bacterial cells, or are gram-positive bacteria or grain-negative bacteria, or are *E. coli*, or are an *E. coli* B strain, or are *E. coli* (B strain) EB0001 cells (also called *E. coli* ASE(DGH) cells), or are *E. coli* (B strain) EB0002 cells. In growth experiments with *E. coli* host cells having oxidizing cytoplasm, specifically the *E. coli* B strains SHuffle® Express (NEB Catalog No. C3028H) and SHuffle® T7 Express (NEB Catalog No. C3029H) and the *E. coli* K strain SHuffle® T7 (NEB Catalog No. C3026H), we have determined that these *E. coli* B strains with oxidizing cytoplasm are able to grow to much higher cell densities than the most closely corresponding *E. coli* K strain.

Prokaryotic Host Cells.

In some embodiments of the invention, expression constructs designed for expression of gene products are provided in host cells, such as prokaryotic host cells. Prokaryotic host cells can include archaea (such as *Haloferax volcanii, Sulfolobus solfataricus*), Grain-positive bacteria (such as *Bacillus subtilis, Bacillus licheniformis, Brevibacillus choshinensis, Lactobacillus brevis, Lactobacillus buchneri, Lactococcus lactis*, and *Streptomyces lividans*), or Grain-negative bacteria, including Alphaproteobacteria (*Agrobacterium tumefaciens, Caulobacter crescentus, Rhodobacter sphaeroides*, and *Sinorhizobium meliloti*), Betaproteobacteria (*Alcaligenes eutrophus*), and Gammaproteobacteria (*Acinetobacter calcoaceticus, Azotobacter vinelandii, Escherichia coli, Pseudomonas aeruginosa*, and *Pseudomonas putida*). Preferred host cells include Gammaproteobacteria of the family Enterobacteriaceae, such as *Enterobacter, Erwinia, Escherichia* (including *E. coli*), *Klebsiella, Proteus, Salmonella* (including *Salmonella typhimurium*), *Serratia* (including *Serratia marcescans*), and *Shigella*.

Eukaryotic Host Cells.

Many additional types of host cells can be used for the expression systems of the invention, including eukaryotic cells such as yeast (*Candida shehatae, Kluyveromyces lactis, Kluyveromyces fragilis*, other *Kluyveromyces* species, *Pichia pastoris, Saccharomyces cerevisiae, Saccharomyces pastorianus* also known as *Saccharomyces carlsbergensis, Schizosaccharomyces pombe, Dekkera/Brettanomyces* species, and *Yarrowia lipolytica*); other fungi (*Aspergillus nidulans, Aspergillus niger, Neurospora crassa, Penicillium, Tolypocladium, Trichoderma reesia*); insect cell lines (*Drosophila melanogaster* Schneider 2 cells and *Spodoptera frugiperda* Sf9 cells); and mammalian cell lines including immortalized cell lines (Chinese hamster ovary (CHO) cells, HeLa cells, baby hamster kidney (BHK) cells, monkey kidney cells (COS), human embryonic kidney (HEK, 293, or HEK-293) cells, and human hepatocellular carcinoma cells (Hep G2)). The above host cells are available from the American Type Culture Collection.

Alterations to Host Cell Gene Functions.

Certain alterations can be made to the gene functions of host cells comprising inducible expression constructs, to promote efficient and homogeneous induction of the host cell population by an inducer. Preferably, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. described in Example 9. For host cells other than *E. coli*, these alterations can involve the function of genes that are structurally similar to an *E. coli* gene, or genes that carry out a function within the host cell similar to that of the *E. coli* gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and/or an altered expression of chaperone proteins, it is also possible to alter the reduction-oxidation environment of the host cell.

Host Cell Reduction-Oxidation Environment.

In bacterial cells such as *E. coli*, proteins that need disulfide bonds are typically exported into the periplasm where disulfide bond formation and isomerization is catalyzed by the Dsb system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., "Strain engineering for improved expression of recombinant proteins in bacteria", Microb Cell Fact 2011 May 14; 10: 32). It is also possible to express cytoplasmic forms of these Dsb proteins, such as a cytoplasmic version of DsbA and/or of DsbC ('cDsbA' or 'cDsbC'), that lacks a signal peptide and therefore is not transported into the periplasm. Cytoplasmic Dsb proteins such as cDsbA and/or cDsbC are useful for making the cytoplasm of the host cell more oxidizing and thus more conducive to the formation of disulfide bonds in heterologous proteins produced in the cytoplasm. The host cell cytoplasm can also be made less reducing and thus more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductant, such as dithiothreitol (DTT). Suppressor mutations (such as ahpC* and ahpC$^\Delta$, Lobstein et al., "SHuffle, a novel *Escherichia coli* protein expression strain capable of correctly folding disulfide bonded proteins in its cytoplasm", Microb Cell Fact 2012 May 8; 11: 56; doi: 10.1186/1475-2859-11-56) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamylcysteine synthetase (gshA) and defective in trxB, to grow in the absence of DTT; these include AhpC V164G, AhpC S71F, AhpC E173/S71F, AhpC E171Ter, and AhpC dup162-169 (Faulkner et al., "Functional plasticity of a peroxidase allows evolution of diverse disulfide-reducing pathways", Proc Natl Acad Sci USA 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds. Other proteins that may be helpful to reduce the oxidative stress effects in host cells of an oxidizing cytoplasm are HPI (hydroperoxidase I) catalase-peroxidase encoded by *E. coli* katG and HPII (hydroperoxidase II) catalase-peroxidase encoded by *E. coli* katE, which disproportionate peroxide into water and $O_2$ (Farr and Kogoma, "Oxidative stress responses in *Escherichia coli* and *Salmonella typhimurium*", Microbiol Rev. 1991 December; 55(4): 561-585; Review). Increasing levels of KatG and/or KatE protein in host cells through induced coexpression or through elevated levels of constitutive expression is an aspect of some embodiments of the invention.

Another alteration that can be made to host cells is to express the sulfhydryl oxidase Erv1p from the inner membrane space of yeast mitochondria in the host cell cytoplasm, which has been shown to increase the production of a variety of complex, disulfide-bonded proteins of eukaryotic origin in the cytoplasm of E. coli, even in the absence of mutations in gor or trxB (Nguyen et al., "Pre-expression of a sulfhydryl oxidase significantly increases the yields of eukaryotic disulfide bond containing proteins expressed in the cytoplasm of E. coli" Microb Cell Fact 2011 Jan. 7; 10: 1).

Host cells comprising expression constructs preferably also express cDsbA and/or cDsbC and/or Erv1p; are deficient in trxB gene function; are also deficient in the gene function of either gor, gshB, or gshA; optionally have increased levels of katG and/or katE gene function; and express an appropriate mutant form of AhpC so that the host cells can be grown in the absence of DTT.

Chaperones.

In some embodiments, desired gene products are coexpressed with other gene products, such as chaperones, that are beneficial to the production of the desired gene product. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct, or can be expressed from the host cell chromosome; preferably, expression of chaperone protein(s) in the host cell is at a sufficiently high level to produce coexpressed gene products that are properly folded and/or assembled into the desired product. Examples of chaperones present in E. coli host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding and therefore expression of these chaperones in combinations has been shown to be beneficial for protein expression (Makino et al., "Strain engineering for improved expression of recombinant proteins in bacteria", Microb Cell Fact 2011 May 14; 10: 32). When expressing eukaryotic proteins in prokaryotic host cells, a eukaryotic chaperone protein, such as protein disulfide isomerase (PDI) from the same or a related eukaryotic species, is in certain embodiments of the invention coexpressed or inducibly coexpressed with the desired gene product.

One chaperone that can be expressed in host cells is a protein disulfide isomerase from *Humicola insolens*, a soil hyphomycete (soft-rot fungus). An amino acid sequence of *Humicola insolens* PDI is shown as SEQ ID NO:1; it lacks the signal peptide of the native protein so that it remains in the host cell cytoplasm. The nucleotide sequence encoding PDI was optimized for expression in E. coli; the expression construct for PDI is shown as SEQ ID NO:2. SEQ ID NO:2 contains a GCTAGC NheI restriction site at its 5' end, an AGGAGG ribosome binding site at nucleotides 7 through 12, the PDI coding sequence at nucleotides 21 through 1478, and a GTCGAC SalI restriction site at its 3' end. The nucleotide sequence of SEQ ID NO: 2 was designed to be inserted immediately downstream of a promoter, such as an inducible promoter. The NheI and SalI restriction sites in SEQ ID NO: 2 can be used to insert it into a vector multiple cloning site, such as that of the pSOL expression vector (SEQ ID NO:3), described in published US patent application US2015353940A1, which is incorporated by reference in its entirety herein. Other PDI polypeptides can also be expressed in host cells, including PDI polypeptides from a variety of species (*Saccharomyces cerevisiae* (UniProtKB P17967), *Homo sapiens* (UniProtKB P07237), *Mus musculus* (UniProtKB P09103), *Caenorhabditis elegans* (UniProtKB Q17770 and Q17967), *Arabdopsis thaliana* (UniProtKB O48773, Q9XI01, Q9SRG3, Q9LJU2, Q9MAU6, Q94F09, and Q9T042), *Aspergillus niger* (UniProtKB Q12730) and also modified forms of such PDI polypeptides. In certain embodiments of the invention, a PDI polypeptide expressed in host cells of the invention shares at least 70%, or 80%, or 90%, or 95% amino acid sequence identity across at least 50% (or at least 60%, or at least 70%, or at least 80%, or at least 90%) of the length of SEQ ID NO:1, where amino acid sequence identity is determined according to Example 10.

Cellular Transport of Cofactors.

When using the expression systems of the invention to produce enzymes that require cofactors for function, it is helpful to use a host cell capable of synthesizing the cofactor from available precursors, or taking it up from the environment. Common cofactors include ATP, coenzyme A, flavin adenine dinucleotide (FAD), $NAD^+/NADH$, and heme. Polynucleotides encoding cofactor transport polypeptides and/or cofactor synthesizing polypeptides can be introduced into host cells, and such polypeptides can be constitutively expressed, or inducibly coexpressed with the gene products to be produced by methods of the invention.

Glycosylation of polypeptide gene products. Host cells can have alterations in their ability to glycosylate polypeptides. For example, eukaryotic host cells can have eliminated or reduced gene function in glycosyltransferase and/or oligo-saccharyltransferase genes, impairing the normal eukaryotic glycosylation of polypeptides to form glycoproteins. Prokaryotic host cells such as E. coli, which do not normally glycosylate polypeptides, can be altered to express a set of eukaryotic and prokaryotic genes that provide a glycosylation function (DeLisa et al., "Glycosylated protein expression in prokaryotes", WO2009089154A2, 2009 Jul. 16).

Available Host Cell Strains with Altered Gene Functions.

To create preferred strains of host cells to be used in the expression systems and methods of the invention, it is useful to start with a strain that already comprises desired genetic alterations (Table A).

TABLE A

Host Cell Strains

| Strain: | Genotype: | Source: |
| --- | --- | --- |
| E. coli TOP10 | F- mcrA Δ(mrr-hsdRMS-mcrBC) φ80lacZΔM15 ΔlacX74 recA1 araD139 Δ(ara-leu)7697 galU galK rpsL ($Str^R$) endA1 nupG λ- | Invitrogen Life Technologies Catalog nos. C4040-10, C4040-03, C4040-06, C4040-50, and C4040-52 |

TABLE A-continued

Host Cell Strains

| Strain: | Genotype: | Source: |
|---|---|---|
| E. coli Origami™ 2 | Δ(ara-leu)7697 ΔlacX74 ΔphoA PvuII phoR araD139 ahpC galE galK rpsL F'[lac+ lacI<sup>q</sup> pro] gor522::Tn10 trxB (Str<sup>R</sup>, Tet<sup>R</sup>) | Merck (EMD Millipore Chemicals) Catalog No. 71344 |
| E. coli SHuffle ® Express | fhuA2 [lon] ompT ahpC gal λatt::pNEB3-r1-cDsbC (Spec, lacI) ΔtrxB sulA11 R(mcr-73::miniTn10--Tet<sup>S</sup>)2 [dcm] R(zgb-210::Tn10--Tet<sup>S</sup>) endA1 Δgor Δ(mcrC-mrr)114::IS10 | New England Biolabs Catalog No. C3028H |

Methods of Altering Host Cell Gene Functions.

There are many methods known in the art for making alterations to host cell genes in order to eliminate, reduce, or change gene function. Methods of making targeted disruptions of genes in host cells such as *E. coli* and other prokaryotes have been described (Muyrers et al., "Rapid modification of bacterial artificial chromosomes by ET-recombination", Nucleic Acids Res 1999 Mar. 15; 27(6): 1555-1557; Datsenko and Wanner, "One-step inactivation of chromosomal genes in *Escherichia coli* K-12 using PCR products", Proc Natl Acad Sci USA 2000 Jun. 6; 97(12): 6640-6645), and kits for using similar Red/ET recombination methods are commercially available (for example, the Quick & Easy *E. coli* Gene Deletion Kit from Gene Bridges GmbH, Heidelberg, Germany). In one embodiment of the invention, the function of one or more genes of host cells is eliminated or reduced by identifying a nucleotide sequence within the coding sequence of the gene to be disrupted, such as one of the *E. coli* K-12 substrain MG1655 coding sequences incorporated herein by reference to the genomic location of the sequence, and more specifically by selecting two adjacent stretches of 50 nucleotides each within that coding sequence. The Quick & Easy *E. coli* Gene Deletion Kit is then used according to the manufacturer's instructions to insert a polynucleotide construct containing a selectable marker between the selected adjacent stretches of coding sequence, eliminating or reducing the normal function of the gene. Red/ET recombination methods can also be used to replace a promoter sequence with that of a different promoter, such as a constitutive promoter, or an artificial promoter that is predicted to promote a certain level of transcription (De Mey et al., "Promoter knock-in: a novel rational method for the fine tuning of genes", BMC Biotechnol 2010 Mar. 24; 10: 26). The function of host cell genes can also be eliminated or reduced by RNA silencing methods (Man et al., "Artificial trans-encoded small non-coding RNAs specifically silence the selected gene expression in bacteria", Nucleic Acids Res 2011 April; 39(8): e50, Epub 2011 Feb. 3). Further, known mutations that alter host cell gene function can be introduced into host cells through traditional genetic methods.

Expression Constructs.

Expression constructs are polynucleotides designed for the expression of one or more gene products of interest, and thus are not naturally occurring molecules. Expression constructs can be integrated into a host cell chromosome, or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more gene products. One or more expression constructs can be integrated into a host cell chromosome or be maintained on an extrachromosomal polynucleotide such as a plasmid or artificial chromosome. The following are descriptions of particular types of polynucleotide sequences that can be used in expression constructs for the expression of gene products. In certain embodiments of the invention, the expression construct is the pSOL expression vector (SEQ ID NO:3), described in published US patent application US2015353940A1, which is incorporated by reference in its entirety herein.

Inducible Promoters.

The following is a description of inducible promoters that can be used in expression constructs for expression of gene products, along with some of the genetic modifications that can be made to host cells that contain such expression constructs. Examples of these inducible promoters and related genes are, unless otherwise specified, those derived from *Escherichia coli* (*E. coli*) strain MG1655 (American Type Culture Collection deposit ATCC 700926), which is a substrain of *E. coli* K-12 (American Type Culture Collection deposit ATCC 10798). Table 1 of International Application PCT/US13/53562 (published as WO2014025663A1) lists the genomic locations, in *E. coli* MG1655, of the nucleotide sequences for these examples of inducible promoters and related genes; the WO2014025663A1 publication is incorporated by reference in its entirety herein. Nucleotide and other genetic sequences, referenced by genomic location as in Table 1 of WO2014025663A1, are expressly incorporated by reference herein. Additional information about *E. coli* promoters, genes, and strains described herein can be found in many public sources, including the online EcoliWiki resource, located at ecoliwiki.net.

Arabinose Promoter.

(As used herein, 'arabinose' means L-arabinose.) Several *E. coli* operons involved in arabinose utilization are inducible by arabinose—araBAD, araC, araE, and araFGH—but the terms 'arabinose promoter' and 'ara promoter' are typically used to designate the araBAD promoter. Several additional terms have been used to indicate the *E. coli* araBAD promoter, such as $P_{ara}$, $P_{araB}$, $P_{araBAD}$, and $P_{BAD}$. The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from $P_{BAD}$, but in the presence of arabinose, the AraC protein, which alters its conformation upon binding arabinose, becomes a positive regulatory element that allows transcription from $P_{BAD}$. The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY(A177C) and the LacY(A177V) proteins, having a cysteine or a valine amino acid instead of alanine at position 177, respectively (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). In order to achieve homogenous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In similar manner, as additional alternatives for homogeneous induction of an arabinose-inducible promoter, a host cell that lacks AraE function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate promoter. The 'propionate promoter' or 'prp promoter' is the promoter for the *E. coli* prpBCDE operon, and is also called $P_{prpB}$. Like the am promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter, and activates transcription from the prp promoter when the PrpR protein binds 2-methylcitrate ('2-MC'). Propionate (also called propanoate) is the ion, $CH_3CH_2COO^-$, of propionic acid (or 'propanoic acid'), and is the smallest of the 'fatty' acids having the general formula $H(CH_2)_nCOOH$ that shares certain properties of this class of molecules: producing an oily layer when salted out of water and having a soapy potassium salt. Commercially available propionate is generally sold as a monovalent cation salt of propionic acid, such as sodium propionate ($CH_3CH_2COONa$), or as a divalent cation salt, such as calcium propionate ($Ca(CH_3CH_2COO)_2$). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-ygfDGH operon. These genes encode proteins required for the conversion of succinate to propionyl-CoA, which can then be converted to 2-MC by PrpC. Elimination or reduction of the function of these proteins would remove a parallel pathway for the production of the 2-MC inducer, and thus might reduce background levels of expression of a propionate-inducible promoter, and increase sensitivity of the propionate-inducible promoter to exogenously supplied propionate. It has been found that a deletion of sbm-ygfD-ygfG-ygfH-ygfI, introduced into *E. coli* BL21(DE3) to create strain JSB (Lee and Keasling, "A propionate-inducible expression system for enteric bacteria", Appl Environ Microbiol 2005 November; 71(11): 6856-6862), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfI also apparently affects ygfI, which encodes a putative LysR-family transcriptional regulator of unknown function. The genes sbm-ygfDGH are transcribed as one operon, and ygfI is transcribed from the opposite strand. The 3' ends of the ygfH and ygfI coding sequences overlap by a few base pairs, so a deletion that takes out all of the sbm-ygfDGH operon apparently takes out ygfI coding function as well. Eliminating or reducing the function of a subset of the sbm-ygfDGH gene products, such as YgfG (also called ScpB, methylmalonyl-CoA decarboxylase), or deleting the majority of the sbm-ygfDGH (or scpA-argK-scpBC) operon while leaving enough of the 3' end of the ygfH (or scpC) gene so that the expression of ygfI is not affected, could be sufficient to reduce background expression from a propionate-inducible promoter without reducing the maximal level of induced expression.

Rhamnose Promoter.

(As used herein, 'rhamnose' means L-rhamnose.) The 'rhamnose promoter' or 'rha promoter', or $P_{rhaSR}$, is the promoter for the E. coli rhaSR operon. Like the ara and pip promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al., "The AraC/XylS family activator RhaS negatively autoregulates rhaSR expression by preventing cyclic AMP receptor protein activation", J Bacteriol 2010 January; 192(1): 225-232). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxyacetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. E. coli cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlBDACX (or rfbBDACX operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD proteins. L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter.

(As used herein, 'xylose' means D-xylose.) The xylose promoter, or 'xyl promoter', or $P_{xylA}$, means the promoter for the E. coli xylAB operon. The xylose promoter region is similar in organization to other inducible promoters in that the xylAB operon and the xylFGHR operon are both expressed from adjacent xylose-inducible promoters in opposite directions on the E. coli chromosome (Song and Park, "Organization and regulation of the D-xylose operons in Escherichia coli K-12: XylR acts as a transcriptional activator", J Bacteriol. 1997 November; 179(22): 7025-7032). The transcriptional regulator of both the $P_{xylA}$ and $P_{xylF}$ promoters is XylR, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and XylB. The xylFGHR operon encodes XylF, XylG, and XylH, the subunits of an ABC superfamily high-affinity D-xylose transporter. The xylE gene, which encodes the E. coli low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose-inducible $P_{xylF}$ promoter, and with the xylE coding sequence expressed from a constitutive promoter rather than its native promoter. As another example, the xylR coding sequence is expressed from the $P_{xylA}$ or the $P_{xylF}$ promoter in an expression construct, while either the xylFGHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter.

The term 'lactose promoter' refers to the lactose-inducible promoter for the lacZYA operon, a promoter which is also called lacZp1; this lactose promoter is located at ca. 365603-365568 (minus strand, with the RNA polymerase binding ('-35') site at ca. 365603-365598, the Pribnow box ('-10') at 365579-365573, and a transcription initiation site at 365567) in the genomic sequence of the E. coli K-12 substrain MG1655 (NCBI Reference Sequence NC_000913.2, 11 Jan. 2012). In some embodiments, expression systems of the invention can comprise a lactose-inducible promoter such as the lacZYA promoter. In other embodiments, the expression systems of the invention comprise one or more inducible promoters that are not lactose-inducible promoters.

Alkaline Phosphatase Promoter.

The terms 'alkaline phosphatase promoter' and 'phoA promoter' refer to the promoter for the phoApsiF operon, a promoter which is induced under conditions of phosphate starvation. The phoA promoter region is located at ca. 401647-401746 (plus strand, with the Pribnow box ('-10') at 401695-401701 (Kikuchi et al., "The nucleotide sequence of the promoter and the amino-terminal region of alkaline phosphatase structural gene (phoA) of Escherichia coli", Nucleic Acids Res 1981 Nov. 11; 9(21): 5671-5678)) in the genomic sequence of the E. coli K-12 substrain MG1655 (NCBI Reference Sequence NC_000913.3, 16 Dec. 2014). The transcriptional activator for the phoA promoter is PhoB, a transcriptional regulator that, along with the sensor protein PhoR, forms a two-component signal transduction system in

*E. coli*. PhoB and PhoR are transcribed from the phoBR operon, located at ca. 417050-419300 (plus strand, with the PhoB coding sequence at 417,142-417,831 and the PhoR coding sequence at 417,889-419,184) in the genomic sequence of the *E. coli* K-12 substrain MG1655 (NCBI Reference Sequence NC_000913.3, 16 Dec. 2014). The phoA promoter differs from the inducible promoters described above in that it is induced by the lack of a substance—intracellular phosphate—rather than by the addition of an inducer. For this reason the phoA promoter is generally used to direct transcription of gene products that are to be produced at a stage when the host cells are depleted for phosphate, such as the later stages of fermentation. In some embodiments, expression systems of the invention can comprise a phoA promoter. In other embodiments, the expression systems of the invention comprise one or more inducible promoters that are not phoA promoters.

Inducible Promoter.

As described above, there are several different inducible promoters that can be included in expression constructs as part of the expression systems of the invention. Preferred inducible promoters share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 1 of WO2014025663A1, where percent polynucleotide sequence identity is determined using the methods of Example 10. Under 'standard' inducing conditions (see Example 3), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. (Example 9). Within the expression construct, an inducible promoter is placed 5' to (or 'upstream of') the coding sequence for the gene product that is to be inducibly expressed, so that the presence of the inducible promoter will direct transcription of the gene product coding sequence in a 5' to 3' direction relative to the coding strand of the polynucleotide encoding the gene product.

Carbon Catabolite Repression (CCR).

The presence of an active CCR regulatory system within a host can affect the ability of an inducer to activate transcription from an inducible promoter. For example, when a host cell such as *E. coli* is grown in a medium containing glucose, an active CCR regulatory system causes genes needed for the utilization of other carbon sources, such as the araBAD and prpBCDE operons, are expressed at a low level if at all, even if the arabinose or propionate inducer is also present in the growth medium. There is also a hierarchy of utilization of carbon sources other than glucose: as in the case of the ara and prp inducible promoter systems, where the presence of arabinose reduces the ability of propionate to induce expression from the prpBCDE promoter (Park et al., "The mechanism of sugar-mediated catabolite repression of the propionate catabolic genes in *Escherichia coli*", Gene 2012 Aug. 1; 504(1): 116-121; Epub 2012 May 3). The CCR mechanism of the cell therefore appears to make it more difficult to use two or more carbon-source inducers in an expression system, as the presence of the inducer that is the preferred carbon source is expected to inhibit induction by less-preferred carbon sources. The Park et al. authors attempted to relieve the repression of the prp promoter by arabinose, by using either a mutant crp gene that produces an altered cAMP receptor protein that can function independently of cAMP, or a deletion of PTS (phosphotransferase system) genes involved in the regulation of CCR; both approaches were largely unsuccessful.

However, host cells of the invention that have been genetically modified, so that they lack the ability to metabolize an inducer into another compound, do not necessarily exhibit CCR by that inducer on promoters regulated by less-preferred carbon sources. This absence of a significant CCR effect is observed when very low concentrations of the non-metabolized inducer are used; surprisingly, those very low concentrations are also the most effective for producing optimal yields of gene product. For example, coexpression of gene products can be carried out by expressing one gene product component from the L-arabinose-inducible araBAD promoter and another gene product component from the propionate-inducible prpBCDE promoter. In host cells such as *E. coli* EB0001 and EB0002 cells (described in Example 1 below), coexpression typically produces the best yields of multimeric gene product at L-arabinose inducer concentrations of less than 100 micromolar (0.0015%) per OD unit of cells, and at these L-arabinose concentrations very little or no L-arabinose-mediated CCR of the prpBCDE promoter is observed.

Products Made by the Methods of the Invention

There is broad versatility in utilizing the expression systems of the present invention in numerous expression applications, and in the properties of the products.

Gene products expressed by the methods of the invention are recombinant gene products, in that they are produced by recombinant engineering methods in which a polynucleotide encoding the gene product to be expressed is placed downstream of a promoter that is used to direct expression of the gene product in a host cell. Gene products expressed by the methods of the invention can also be heterologous gene products, in that the gene product is native to a species other than that of the host cell. For example, the methods of the invention can be used to express mammalian polypeptides in microbial cells. Further, gene products expressed by the methods of the invention can also be artificial (non-naturally occurring) gene products, in that the polynucleotide and/or amino acid sequences of the gene products are the product of human invention and do not occur in nature.

Gene products expressed by the methods of the invention are in some instances polypeptides, such as any, or more than one, of the following: 1-antitrypsin; 2C4; activin; addressins; alkaline phosphatase; anti-CD11a; anti-CD18; anti-CD20; anti-clotting factors such as Protein C; anti-HER-2 antibody; anti-IgE; anti-IgG; anti-VEGF; antibodies and antibody fragments; antibodies to ErbB2 domain(s) such as 2C4 (WO 01/00245 hybridoma ATCC HB-12697), which binds to a region in the extracellular domain of ErbB2 (e.g., any one or more residues in the region from about residue 22 to about residue 584 of ErbB2, inclusive); Apo2 ligand (Apo2L); atrial naturietic factor; BDNF; beta-lactamase; bombesin; bone morphogenetic protein (BMP); brain IGF-I; calcitonin; cardiotrophins (cardiac hypertrophy factor) such as cardiotrophin-1 (CT-1); CD proteins such as CD-3, CD-4, CD-8, and CD-19; clotting factors such as factor VIIIC, factor IX, tissue factor, and von Willebrands factor; colony stimulating factors (CSFs), e.g., M-CSF, GM-CSF, and G-CSF; decay-accelerating factor; des(1-3)-IGF-I (brain IGF-I); DNase; enkephalinase; epidermal growth factor (EGF); erythropoietin; fibroblast growth factor such as aFGF and bFGF; follicle-stimulating hormone; glucagon; gp120; growth hormone, including human growth hormone or bovine growth hormone; growth-hormone releasing factor; hemopoietic growth factor; homing receptors; HSA;

IGF-I; IGF-II; immunotoxins; inhibin; insulin chains (insulin A-chain, insulin B-chain) or proinsulin; insulin-like growth factor binding proteins; insulin-like growth factor-I and -II (IGF-I and IGF-II); integrin; interferon such as interferon-alpha, -beta, and -gamma; interleukins (ILs), e.g., IL-1 to IL-10; lipoproteins; lung surfactant; luteinizing hormone; mouse gonadotropin-associated peptide; mullerian-inhibiting substance; nerve growth factor (NGF); neurotrophic factor such as brain-derived neurotrophic factor (BDNF), neurotrophin-3, -4, -5, or -6 (NT-3, NT-4, NT-5, or NT-6); osteoinductive factors; parathyroid hormone; plasminogen activator, such as urokinase or human urine or tissue-type plasminogen activator (t-PA); platelet-derived growth factor (PDGF); prorelaxin; protein A or D; receptors for hormones or growth factors; regulatory proteins; relaxin A-chain; relaxin B-chain; rennin; rheumatoid factors; serum albumin, such as human serum albumin (HSA) or bovine serum albumin (BSA); superoxide dismutase; surface-membrane proteins; T-cell receptors; TGF-beta; thrombin; thrombopoietin; thyroid-stimulating hormone; transforming growth factor (TGF) such as TGF-alpha and TGF-beta, including TGF-1, TGF-2, TGF-3, TGF-4, or TGF-5; transport proteins; tumor necrosis factor-alpha and -beta; urokinase; vascular endothelial growth factor (VEGF); viral antigens such as, for example, a portion of the AIDS envelope; and fragments of any of the above-listed polypeptides.

Gene products expressed by the methods of the invention can include any, or more than one, of the following insulin polypeptides. An insulin polypeptide produced by the methods of the invention comprises in some embodiments the amino acid sequence of a mature A chain or of a mature B chain of insulin, and in other embodiments comprises both a mature A chain and a mature B chain. A proinsulin polypeptide comprises a mature A chain of insulin and a mature B chain of insulin. Insulin polypeptide chains in certain embodiments comprise one or more of any of the naturally occurring amino acid sequences of insulins, or fragments thereof, and in other embodiments comprise one or more insulin analogue amino acid sequences, or fragments thereof, and in further embodiments comprise combinations of naturally occurring insulin amino acid sequences and/or insulin analogue amino acid sequences. Examples of naturally occurring insulin amino acid sequences and insulin analogue amino acid sequences are shown in Table B. Insulin degludec and insulin detemir have modified B29 lysine residues as described in the "Sequences Presented in The Sequence Listing" table below.

TABLE B

Insulin Chain Amino Acid Sequences

| Name: | Description: | Sequence: |
|---|---|---|
| Insulin (regular) | Native human insulin | A: GIVEQCCTSICSLYQLENYCN (SEQ ID NO: 4)<br>B: FVNQHLCGSHLVEALYLVCGERGFFYTPKT (SEQ ID NO: 5) |
| Isophane insulin | Neutral protamine Hagedorn insulin; formulated to be intermediate-acting | A: GIVEQCCTSICSLYQLENYCN (SEQ ID NO: 4)<br>B: FVNQHLCGSHLVEALYLVCGERGFFYTPKT (SEQ ID NO: 5) |
| Insulin lispro | Insulin analogue, rapid-acting | A: GIVEQCCTSICSLYQLENYCN (SEQ ID NO: 4)<br>B: FVNQHLCGSHLVEALYLVCGERGFFYTKPT (SEQ ID NO: 6) |
| Insulin aspart | Insulin analogue, fast-acting | A: GIVEQCCTSICSLYQLENYCN (SEQ ID NO: 4)<br>B: FVNQHLCGSHLVEALYLVCGERGFFYTDKT (SEQ ID NO: 7) |
| Insulin glulisine | Insulin analogue, rapid-acting | A: GIVEQCCTSICSLYQLENYCN (SEQ ID NO: 4)<br>B: FVKQHLCGSHLVEALYLVCGERGFFYTPET (SEQ ID NO: 8) |
| Insulin glargine | Insulin analogue, slow-release, long-acting | A: GIVEQCCTSICSLYQLENYCG (SEQ ID NO: 9)<br>B: FVNQHLCGSHLVEALYLVCGERGFFYTPKTRR (SEQ ID NO: 10) |
| Insulin degludec | Insulin analogue, long-acting | A: GIVEQCCTSICSLYQLENYCN (SEQ ID NO: 4)<br>B: FVNQHLCGSHLVEALYLVCGERGFFYTPK* (SEQ ID NO: 11) |
| Insulin detemir | Insulin analogue, long-acting | A: GIVEQCCTSICSLYQLENYCN (SEQ ID NO: 4)<br>B: FVNQHLCGSHLVEALYLVCGERGFFYTPK* (SEQ ID NO: 12) |

A: mature A chain;
B: mature B chain;
Underlining: differences from native human insulin
*modified residue Disulfide Bonds.

Gene products expressed by the methods of the invention are in some instances polypeptides that form disulfide bonds. The numbers and locations of disulfide bonds formed by a polypeptide can be determined by methods such as that of Example 7). The number of disulfide bonds for a gene product such as a polypeptide is the total number of intramolecular and intermolecular bonds formed by that gene product when it is present in a functional product. For example, a light chain of a human IgG antibody typically has three disulfide bonds (two intramolecular bonds and one intermolecular bond), and a heavy chain of a human IgG antibody typically has seven disulfide bonds (four intramolecular bonds and three intermolecular bonds). In certain embodiments of the invention, a gene product expressed by methods of the invention is a polypeptide that forms at least one and fewer than twenty disulfide bonds, or at least two and fewer than seventeen disulfide bonds, or at least eighteen and fewer than one hundred disulfide bonds, or at least three and fewer than ten disulfide bonds, or at least three and fewer than eight disulfide bonds, or is a polypeptide that forms a number of disulfide bonds selected from the group consisting of one, two, three, four, five, six, seven, eight, and nine disulfide bonds.

Signal Peptides.

Polypeptide gene products expressed by the methods of the invention typically lack signal peptides, as it is desirable for such gene products to be retained in the oxidizing cytoplasm of the host cell. Signal peptides (also termed signal sequences, leader sequences, or leader peptides) are characterized structurally by a stretch of hydrophobic amino acids, approximately five to twenty amino acids long and often around ten to fifteen amino acids in length, that has a tendency to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that is recognized and cleaved by signal peptidase. Signal peptides can be characterized functionally by the ability to direct transport of a polypeptide, either co-translationally or post-translationally, through the plasma membrane of prokaryotes (or the inner membrane of grain negative bacteria like *E. coli*), or into the endoplasmic reticulum of eukaryotic cells. The degree to which a signal peptide enables a polypeptide to be transported into the periplasmic space of a host cell like *E. coli*, for example, can be determined by separating periplasmic proteins from proteins retained in the cytoplasm, using a method such as that provided in Example 8.

'Tags'.

In addition, gene products to be expressed by the methods of the invention can be designed to include molecular moieties that aid in the purification and/or detection of the gene products. Many such moieties are known in the art; as one example, a polypeptide gene product can be designed to include a polyhistidine 'tag' sequence—a run of six or more histidines, preferably six to ten histidine residues, and most preferably six histidines—at its N- or C-terminus. The presence of a polyhistidine sequence on the end of a polypeptide allows it to be bound by cobalt- or nickel-based affinity media, and separated from other polypeptides. The polyhistidine tag sequence can be removed by exopeptidases.

Additional tags, expressed at the N-terminal end of the amino acid sequence of a polypeptide gene product produced by the methods of the invention, comprise in certain embodiments: (1) the self-cleaving N-terminal portions ($N^{pro}$) of polyproteins from pestiviruses such as Hog cholera virus (strain Alfort) (SEQ ID NO:13), also called classical swine fever virus (CSFV), and from border disease virus (BDV) and bovine viral diarrhea virus (BVDV), and fragments thereof; (2) the N-terminal portion of carboxypeptidase B ('CPB') precursor, which is for example SEQ ID NO:14 (amino acids 21-110 of *Sus scrofa* CPB, SwissProt P09955.5), and fragments thereof; and/or (3) small ubiquitin-related modifier (SUMO) (SEQ ID NO:15, SwissProt P55853.1) Any N-terminal tag may itself be further tagged at its N-terminus with a polyhistidine tag such as 6×His, allowing for initial purification of the tagged polypeptide on a nickel column, followed by self-cleavage of tags such as $N^{pro}$, or enzymatic cleavage of the CPB or SUMO N-terminal tag by trypsin or SUMO protease, respectively, and elution of the freed polypeptide from the column. In one embodiment of this method, the SUMO protease polypeptides are also fusion proteins comprising 6×His tags, allowing for a two-step purification: in the first step, the expressed 6×His-SUMO-tagged polypeptide is purified by binding to a nickel column, followed by elution from the column. In the second step, the SUMO tags on the purified polypeptides are cleaved by the 6×His-tagged SUMO protease, and the SUMO protease-polypeptide reaction mixture is run through a second nickel column, which retains the SUMO protease but allows the now untagged polypeptide to flow through.

As another example, fluorescent protein sequences can be expressed as part of a polypeptide gene product, with the amino acid sequence for the fluorescent protein preferably added at the N- or C-terminal end of the amino acid sequence of the polypeptide gene product. The resulting fusion protein fluoresces when exposed to light of certain wavelengths, allowing the presence of the fusion protein to be detected visually. A well-known fluorescent protein is the green fluorescent protein of *Aequorea victoria*, and many other fluorescent proteins are commercially available, along with nucleotide sequences encoding them.

Glycosylation.

Gene products expressed by the methods of the invention may be glycosylated or unglycosylated. In one embodiment of the invention, the expressed gene products are polypeptides. Glycosylated polypeptides are polypeptides that comprise a covalently attached glycosyl group, and include polypeptides comprising all the glycosyl groups normally attached to particular residues of that polypeptide (fully glycosylated polypeptides), partially glycosylated polypeptides, polypeptides with glycosylation at one or more residues where glycosylation does not normally occur (altered glycosylation), and polypeptides glycosylated with at least one glycosyl group that differs in structure from the glycosyl group normally attached to one or more specified residues (modified glycosylation). An example of modified glycosylation is the production of "defucosylated" or "fucose-deficient" polypeptides, polypeptides lacking fucosyl moieties in the glycosyl groups attached to them, by expression of polypeptides in host cells lacking the ability to fucosylate polypeptides. Unglycosylated polypeptides are polypeptides that do not comprise a covalently bound glycosyl group. An unglycosylated polypeptide can be the result of deglycosylation of a polypeptide, or of production of an aglycosylated polypeptide. Deglycosylated polypeptides can be obtained by enzymatically deglycosylating glycosylated polypeptides, whereas aglycosylated polypeptides can be produced by expressing polypeptides in host cells that do not have the capability to glycosylate polypeptides, such as prokaryotic cells or cells in which the function of at least one glycosylation enzyme has been eliminated or reduced. In a particular embodiment, the expressed polypeptides are aglycosylated, and in a more specific embodiment, the aglycosylated polypeptides are expressed in prokaryotic cells such as *E. coli*.

Other Modifications of Gene Products.

Gene products expressed by the methods of the invention may be covalently linked to other types of molecules. Examples of molecules that may be covalently linked to expressed gene products, without limiting the scope of the invention, include polypeptides (such as receptors, ligands, cytokines, growth factors, polypeptide hormones, DNA-binding domains, protein interaction domains such as PDZ domains, kinase domains, antibodies, and fragments of any such polypeptides); water-soluble polymers (such as polyethylene glycol (PEG), carboxymethylcellulose, dextran, polyvinyl alcohol, polyoxyethylated polyols (such as glycerol), polyethylene glycol propionaldehyde, and similar compounds, derivatives, or mixtures thereof); and cytotoxic agents (such as chemotherapeutic agents, growth-inhibitory agents, toxins (such as enzymatically active toxins of bacterial, fungal, plant, or animal origin, or fragments thereof), and radioactive isotopes).

Antibodies.

In one embodiment of the invention, the expressed gene products are antibodies. The term 'antibody' is used in the broadest sense and specifically includes 'native' antibodies, fully-human antibodies, humanized antibodies, chimeric antibodies, multispecific antibodies (such as bispecific antibodies), monoclonal antibodies, polyclonal antibodies, antibody fragments, and other polypeptides derived from antibodies that are capable of binding antigen. Unless indicated otherwise herein, the numbering of the residues in an immunoglobulin heavy chain ('EU numbering') is that of the EU index (the residue numbering of the human IgG1 EU antibody) as in Kabat et al., Sequences of Proteins of Immunological Interest, Fifth Edition, 1991, National Institute of Health, Bethesda, Maryland.

'Native' antibodies are usually heterotetrameric glycoproteins of about 150,000 daltons, composed of two identical light (L) chains and two identical heavy (H) chains. Each light chain is linked to a heavy chain by one covalent disulfide bond, while the number of inter-chain disulfide linkages varies among the heavy chains of different immunoglobulin isotypes. Each heavy and light chain also has regularly spaced intrachain disulfide bridges. Each heavy chain has at its N-terminal end a variable domain ($V_H$) followed by a number of constant domains. Each light chain has a variable domain at it N-terminal end ($V_L$) and a constant domain at its C-terminal end; the constant domain of the light chain is aligned with the first constant domain of the heavy chain, and the light-chain variable domain is aligned with the variable domain of the heavy chain. The term 'variable' refers to the fact that certain portions of the variable domains differ extensively in sequence among antibodies and are used in the binding and specificity of each particular antibody for an antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, connected by three HVRs, and with the HVRs from the other chain, contribute to the formation of the antigen-binding site of antibodies.

The term 'Fc region' refers to a C-terminal region of an immunoglobulin heavy chain, and includes native Fc regions and variant Fc regions. Although the boundaries of the Fc region of an immunoglobulin heavy chain might vary, the human IgG heavy-chain Fc region can be defined to stretch from an amino acid residue at position Cys226, or from Pro230, to the carboxyl-terminus thereof. Alternatively, the Fc region can be defined to extend from the N-terminal residue (Ala231) of the conserved $C_H2$ immunoglobulin domain to the C-terminus, and may include multiple conserved domains such as $C_H2$, $C_H3$, and $C_H4$. The C-terminal lysine (residue 447 according to the EU numbering system) of the native Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain at least five different classes of Fc receptors. The binding of an antibody to FcRs determines its ability to recruit other immunological cells and the type of cell recruited. Hence, the ability to engineer antibodies with altered Fc regions that can recruit only certain kinds of cells can be critically important for therapy (US Patent Application 20090136936 A1, May 28, 2009, Georgiou, George). Native antibodies produced by mammalian cells typically comprise a branched, biantennary oligosaccharide that is generally attached by an N-linkage to Asn297 of the CH2 domain of the Fc region. In certain embodiments, antibodies produced by the methods of the invention are not glycosylated or are aglycosylated, for example, due to a substitution at residue 297 of the Fc region, or to expression in a host cell that does not have the capability to glycosylate polypeptides. Due to altered ADCC responses, unglycosylated antibodies may stimulate a lower level of inflammatory responses such as neuroinflammation. Also, since an antibody having an aglycosylated Fc region has very low binding affinity for Fc receptors, such antibodies would not bind to the large number of immune cells that bear these receptors. This is a significant advantage since it reduces non-specific binding, and also increases the half-life of the antibody in vivo, making this attribute very beneficial in therapeutics.

The terms 'full-length antibody', 'intact antibody', and 'whole antibody' are used interchangeably to refer to an antibody in its substantially intact 'native' form, not antibody fragments as defined below. The terms particularly refer to an antibody with heavy chains that each comprise a variable domain and an Fc region. 'Antibody fragments' comprise a portion of an intact antibody, preferably comprising the antigen-binding region thereof. Examples of antibody fragments include Fab, Fab', F(ab')$_2$, Fc, Fd, and Fv fragments; diabodies; linear antibodies; single-chain antibody molecules such as scFv; and multispecific antibodies formed from antibody fragments.

A 'human antibody' is one that possesses an amino-acid sequence corresponding to that of an antibody produced by a human. A 'chimeric' antibody is one in which a portion of the heavy and/or light chain is identical to, or shares a certain degree of amino acid sequence identity with, corresponding sequences in antibodies derived from a particular species or belonging to a particular antibody class or subclass, while the remainder of the chain(s) is identical to, or shares a certain degree of amino acid sequence identity with, corresponding sequences in antibodies derived from another species or belonging to another antibody class or subclass, as well as fragments of such antibodies. A 'humanized' antibody is a chimeric antibody that contains minimal amino acid residues derived from non-human immunoglobulin molecules. In one embodiment, a humanized antibody is a human immunoglobulin (recipient antibody) in which HVR residues of the recipient antibody are replaced by residues from an immunoglobulin HVR of a non-human species (donor antibody) such as mouse, rat, rabbit, or nonhuman primate. In some instances, FR residues of the human recipient antibody are replaced by corresponding non-human residues. Furthermore, humanized antibodies may comprise residues that are not found in the recipient antibody or in the donor antibody. The term 'monoclonal antibody' refers to an antibody obtained from a population of substantially homogeneous antibodies, in that the individual antibodies comprising the population are identical except for possible mutations, such as naturally occurring mutations, that may be present in minor amounts. Thus, the modifier 'monoclonal' indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against the same single determinant on an antigen. In addition to their specificity, monoclonal antibody preparations are advantageous in that they are typically uncontaminated by other immunoglobulins.

The 'binding affinity' of a molecule such as an antibody generally refers to the strength of the sum total of non-covalent interactions between a single binding site of a molecule and its binding partner (such as an antibody and the antigen it binds). Unless indicated otherwise, 'binding affinity' refers to intrinsic binding affinity that reflects a 1:1 interaction between members of a binding pair (such as antibody and antigen). The affinity of a molecule X for its partner Y can generally be represented by the dissociation constant (Kd). Low-affinity antibodies (higher Kd) generally bind antigen slowly and tend to dissociate readily, whereas high-affinity antibodies (lower Kd) generally bind antigen faster and tend to remain bound longer. A variety of ways to measure binding affinity are known in the art, any of which can be used for purposes of the present invention. Specific illustrative methods for measuring binding affinity are described in Example 6. Antibodies and antibody fragments produced by and/or used in methods of the invention preferably have binding affinities of less than 100 nM, more preferably have binding affinities of less than 10 nM, and most preferably have binding affinities of less than 2 nM, as measured by a surface-plasmon resonance assay as described in Example 6.

Enzymes Used in Industrial Applications.

Many industrial processes utilize enzymes that can be produced by the methods of the invention. These processes include treatment of wastewater and other bioremediation and/or detoxification processes; bleaching of materials in the paper and textile industries; and degradation of biomass into material that can be fermented efficiently into biofuels. In many instances it would be desirable to produce enzymes for these applications in microbial host cells or preferably in bacterial host cells, but the active enzyme is difficult to express in large quantities due to problems with enzyme folding and/or a requirement for a cofactor. In certain embodiments of the invention, the expression methods of the invention are used to produce enzymes with industrial applications, such as arabinose- and xylose-utilization enzymes (e.g. xylose isomerase (EC 5.3.1.5)) or lignin-degrading peroxidases (e.g. lignin peroxidase (EC 1.11.1.14), manganese peroxidase (EC 1.11.1.13), versatile peroxidase (EC 1.11.1.16), or laccase (EC 1.10.3.2)).

Solubility and Activity of Products Made by the Methods of the Invention

As described above, the methods of the invention can be used to produce a wide variety of gene products in soluble and active form, as opposed to in inclusion bodies, which are insoluble and in which the gene product is inactive. The production of gene products in soluble form can be confirmed using the methods described in Example 4. With regard to the activity of the gene product, the selection of methods for characterizing gene product activity will depend on the nature of the gene product. For example, if the gene product is an antibody, then the methods of Example 6 can be used to measure the degree to which the antibody can bind antigen, an important aspect of antibody activity. If the gene product is an enzyme, the ability of the enzyme to catalyze an appropriate biochemical reaction can be measured. For polypeptides that form disulfide bonds, one indication that a polypeptide has been produced in active form is the presence of correctly positioned disulfide bonds in the polypeptide, as can be determined using the methods of Example 7.

Growth Methods and Media

The fermentation processes involved in the production of recombinant proteins will use a mode of operation which falls within one of the following categories: (1) discontinuous (batch process) operation, (2) continuous operation, and (3) semi-continuous (fed-batch) operation. A batch process is characterized by inoculation of the sterile culture medium (batch medium) with microorganisms at the start of the process, cultivated for a specific reaction period. During cultivation, cell concentrations, substrate concentrations (carbon source, nutrient salts, vitamins, etc.) and product concentrations change. Good mixing ensures that there are no significant local differences in composition or temperature of the reaction mixture. The reaction is non-stationary and cells are grown until the growth-limiting substrate (generally the carbon source) has been consumed.

Continuous operation is characterized in that fresh culture medium (feed medium) is added continuously to the fermentor and spent media and cells are drawn continuously from the fermentor at the same rate. In a continuous operation, growth rate is determined by the rate of medium addition, and the growth yield is determined by the concentration of the growth limiting substrate (i.e. carbon source). All reaction variables and control parameters remain constant in time and therefore a time-constant state is established in the fermentor followed by constant productivity and output.

Semi-continuous operation can be regarded as a combination of batch and continuous operation. The fermentation is started off as a batch process and when the growth-limiting substrate has been consumed, a continuous feed medium containing glucose and minerals is added in a specified manner (fed-batch). In other words, this operation employs both a batch medium and a feed medium to achieve cell growth and efficient production of the desired protein. No cells are added or taken away during the cultivation period and therefore the fermentor operates batchwise as far as the microorganisms are concerned. While the present invention can be utilized in a variety of processes, including those mentioned above, a particular utilization is in conjunction with a fed-batch process.

In each of the above processes, cell growth and product accumulation can be monitored indirectly by taking advantage of a correlation between metabolite formation and some other variable, such as medium pH, optical density, color, and titrable acidity. For example, optical density provides an indication of the accumulation of insoluble cell particles and can be monitored on-stream using a micro-OD unit coupled to a display device or a recorder, or off-line by sampling. Optical density readings at 600 nanometers (OD600) are used as a means of determining dry cell weight.

High-cell-density fermentations are generally described as those processes which result in a yield of >30 g cell dry weight/liter ($OD_{600}$>60) at a minimum, and in certain embodiments result in a yield of >40 g cell dry weight/liter (OD$_{600}$>80). All high-cell-density fermentation processes employ a concentrated nutrient media that is gradually metered into the fermentor in a "fed-batch" process. A concentrated nutrient feed media is required for high-cell-density processes in order to minimize the dilution of the fermentor contents during feeding. A fed-batch process is required because it allows the operator to control the carbon source feeding, which is important because if the cells are exposed to concentrations of the carbon source high enough to generate high cell densities, the cells will produce so much of the inhibitory byproduct, acetate, that growth will stop (Majewski and Domach, "Simple constrained-optimization view of acetate overflow in *E. coli*", Biotechnol Bioeng 1990 Mar. 25; 35(7): 732-738).

Acetic acid and its deprotonated ion, acetate, together represent one of the main inhibitory byproducts of bacterial growth and recombinant protein production in bioreactors. At pH 7, acetate is the most prevalent form of acetic acid. Any excess carbon energy source may be converted to acetic acid when the amount of the carbon energy source greatly exceeds the processing ability of the bacterium. Research has shown that saturation of the tricarboxylic acid cycle and/or the electron transport chain is the most likely cause of the acetic acid accumulation. The choice of growth medium may affect the level of acetic acid inhibition; cells grown in defined media may be affected by acetic acid more than those grown in complex media. Replacement of glucose with glycerol may also greatly decrease the amount of acetic acid produced. It is believed that glycerol produces less acetic acid than glucose because its rate of transport into a cell is much slower than that of glucose. However, glycerol is more expensive than glucose, and may cause the bacteria to grow more slowly. The use of reduced growth temperatures can also decrease the speed of carbon source uptake and growth rate thus decreasing the production of acetic acid. Bacteria produce acetic acid not only in the presence of an excess carbon energy source or during fast growth, but also under anaerobic conditions. When bacteria such as *E. coli* are allowed to grow too fast, they may exceed the oxygen delivery ability of the bioreactor system which may lead to anaerobic growth conditions. To prevent this from happening, a slower constant growth rate may be maintained through nutrient limitation. Other methods for reducing acetic acid accumulation include genetic modification to prevent acetic acid production, addition of acetic acid utilization genes, and selection of strains with reduced acetic acid. *E. coli* BL21(DE3) is one of the strains that has been shown to produce lower levels of acetic acid because of its ability to use acetic acid in its glyoxylate shunt pathway.

Various larger-scale fed-batch fermentors are available for production of recombinant proteins. Larger fermentors have at least 1000 liters of capacity, preferably about 1000 to 100,000 liters of capacity (i.e. working volume), leaving adequate room for headspace. These fermentors use agitator impellers or other suitable means to distribute oxygen and nutrients, especially glucose (the preferred carbon/energy source). Small-scale fermentation refers generally to fermentation in a fermentor that is no more than approximately 100 liters in volumetric capacity, and in some specific embodiments no more than approximately 10 liters.

Standard reaction conditions for the fermentation processes used to produce recombinant proteins generally involve maintenance of pH at about 5.0 to 8.0 and cultivation temperatures ranging from 20 to 50 degrees C. for microbial host cells such as *E. coli*. In one embodiment of the present invention which utilizes *E. coli* as the host system, fermentation is performed at an optimal pH of about 7.0 and an optimal cultivation temperature of about 30 degrees C.

The standard nutrient media components in these fermentation processes generally include a source of energy, carbon, nitrogen, phosphorus, magnesium, and trace amounts of iron and calcium. In addition, the media may contain growth factors (such as vitamins and amino acids), inorganic salts, and any other precursors essential to product formation. The media may contain a transportable organophosphate such as a glycerophosphate, for example an alpha-glycerophosphate and/or a beta-glycerophosphate, and as a more specific example, glycerol-2-phosphate and/or glycerol-3-phosphate. The elemental composition of the host cell being cultivated can be used to calculate the proportion of each component required to support cell growth. The component concentrations will vary depending upon whether the process is a low-cell-density or a high-cell-density process. For example, the glucose concentrations in low-cell-density batch fermentation processes range from 1 to 5 g/L, while high-cell-density batch processes use glucose concentrations ranging from 45 g/L to 75 g/L. In addition, growth media may contain modest concentrations (for example, in the range of 0.1-5 mM, or 0.25 mM, 0.5 mM, 1 mM, 1.5 mM, or 2 mM) of protective osmolytes such as betaine, dimethylsulfoniopropionate, and/or choline.

During exponential growth of host cells, the metabolic rate is directly proportional to availability of oxygen and a carbon/energy source; thus, reducing the levels of available oxygen or carbon/energy sources, or both, will reduce metabolic rate. Manipulation of fermentor operating parameters, such as agitation rate or back pressure, or reducing $O_2$ pressure, modulates available oxygen levels and can reduce host cell metabolic rate. Reducing concentration or delivery rate, or both, of the carbon/energy source(s) has a similar effect. Furthermore, depending on the nature of the expression system, induction of expression can lead to a decrease in host cell metabolic rate. Finally, upon reaching maximum cell density, the growth rate stops or decreases dramatically. Reduction in host cell metabolic rate can result in more controlled expression of the gene product(s) of interest, including the processes of protein folding and assembly. Host cell metabolic rate can be assessed by measuring cell growth rates, either specific growth rates or instantaneous growth rates (by measuring optical density (OD) such as OD600 and or optionally by converting OD to biomass), as described in Example 1 below. Desirable growth rates are, in certain embodiments of the invention, in the range of 0.01 to 0.7, or are in the range of 0.05 to 0.3, or are in the range of 0.1 to 0.2, or are approximately 0.15 (0.15 plus-or-minus 10%), or are 0.15.

Example 1

Production of Soluble Protein (Infliximab) in Cells with Oxidizing Cytoplasm, Grown to High Cell Densities A. Preparation of *E. coli* EB0001(pBAD24-Infliximab_HC/pPRO33-Infliximab_LC) Cells.

The *E. coli* EB0001 strain, which is also called ASE (DGH), was prepared as described in Example 3 of International Application PCT/US13/53562 (published as WO2014025663A1) and in Example 1.B. of International Application PCT/US14/14968 (published as WO2015020690A1); the WO2014025663A1 and WO2015020690A1 publications are incorporated by reference in their entirety herein. The genotype of *E. coli* EB0001 can be expressed as:

ΔaraBAD fhuA2 [lon] ompT ahpC$^\Delta$ gal λatt::pNEB3-r1-cDsbC (Spec, lacI) ΔtrxB sulA11 R(mcr-73::miniTn10-Tet$^S$)2 [dcm] R(zgb-210::Tn10-Tet$^S$) ΔaraEp::J23104 ΔscpA-argK-scpBC endA1 rpsL-Arg43 Δgor Δ(mcrC-mrr)114::IS10

Strain EB0002 has a genotype which can be expressed as EB0001 prpD, or as:

ΔaraBAD fhuA2 prpD [lon] ompT ahpC$^\Delta$ gal λatt::pNEB3-r1-cDsbC (Spec, lacI) ΔtrxB sulA11 R(mcr-73::miniTn10-Tet$^S$)2 [dcm] R(zgb-210::Tn10-Tet$^S$) ΔaraEp::J23104 ΔscpA-argK-scpBC endA1 rpsL-Arg43 Δgor Δ(mcrC-mrr)114::IS10

Infliximab is a chimeric monoclonal antibody that binds to TNF-alpha. Codon-optimized polynucleotide sequences encoding the infliximab heavy chain and the infliximab light chain were cloned into the pBAD24 and pPRO33 vectors, respectively, as described in Example 5 of WO2014025663A1. The resulting pBAD24-Infliximab_HC and pPRO33-Infliximab_LC expression constructs were transformed into *E. coli* EB0001 by heat shock at 42 degrees C. followed by incubation at 37 degrees C. overnight to create *E. coli* EB0001(pBAD24-Infliximab_HC/pPRO33-Infliximab_LC) host cells.

B. Growth of *E. coli* EB0001(pBAD24-Infliximab_HC/pPRO33-Infliximab_LC) Cells.

*E. coli* EB0001(pBAD24-Infliximab_HC/pPRO33-Infliximab_LC) host cells were grown to high cell densities using the following methods. The equipment and media common to six fermentation runs, referred to as Run A-Run F, are described below, followed by the unique aspects of each fermentation run for the growth periods shown in FIGS. 1-3.

Fermentation Equipment.

The host cells were grown in a New Brunswick BioFlo/CelliGen 115 water jacketed fermentor (Eppendorf North America, Hauppauge, New York), 1 L vessel size with a 2× Rushton impeller and a BioFlo/CelliGen 115 Fermentor/Bioreactor controller; temperature, pH, and dissolved oxygen (DO) were monitored.

It is also possible to grow the host cells in a four-fold configurable DASGIP system (Eppendorf North America, Hauppauge, New York) comprising four 60- to 250-ml DASbox fermentation vessels, each with a 2× Rushton impeller, a DASbox exhaust condenser, and a DASbox feeding and monitoring module (which includes a temperature sensor, a pH/redox sensor, and a dissolved oxygen sensor).

Fermentation Media.

In a 1 L Corning bottle, the following were combined:
29 g soytone (2.9%)
14.3 g yeast extract (1.43%)
1.74 g potassium phosphate (monobasic)
3.00 g potassium phosphate (dibasic)
1.33 g sodium phosphate (monobasic, monohydrate)
5.77 g ammonium sulfate
1.15 g sodium citrate, dihydrate
0.75 mL antifoam 204 (Sigma-Aldrich, St. Louis, Missouri)

The bottle was filled to 1 L with MilliQ double-distilled H$_2$O, and the pH adjusted to 7.0 with ammonium hydroxide. 900 mL of the fermentation media solution was transferred to the fermentor vessels and autoclaved for 45 minutes. After autoclaving, the fermentor vessels were allowed to cool, the sensors were calibrated, and a further six hours were allowed for equilibration after calibration.

After equilibration, the following amounts of filter-sterilized solutions were added by syringe to the fermentor (amounts shown per 1 L):
2.40 mL 50% MgSO$_4$
0.3 mL 50 mg/mL ferrous sulfate, heptahydrate
1 mL 1000× Trace Metals (preparation of this solution is described below)
Appropriate amount/type of antibiotics (100 micrograms/mL ampicillin (AMP) for pBAD24 and 34 micrograms/mL chloramphenicol (CAM) for pPRO33)
2.5% glucose using a sterile 40% glucose stock 1000× Trace Metals (Store at 4 Degrees C.):
In a 250 mL Corning bottle, the following were combined:
0.8 g zinc sulfate heptahydrate
0.8 g cupric sulfate pentahydrate
0.2 g boric acid
0.7 g sodium molybdate dihydrate
0.5 g manganese(II) sulfate monohydrate
8.0 g Ferrous Sulfate
6N sulfuric acid 3.125 mL
   Note that the quantity of sulfuric acid can vary as required to dissolve the other components properly, the usual range is between 2-5 mL
Filled to 100 mL with MilliQ double-distilled H$_2$O
Filter sterilized and stored at 4 degrees C.

Figure 2:
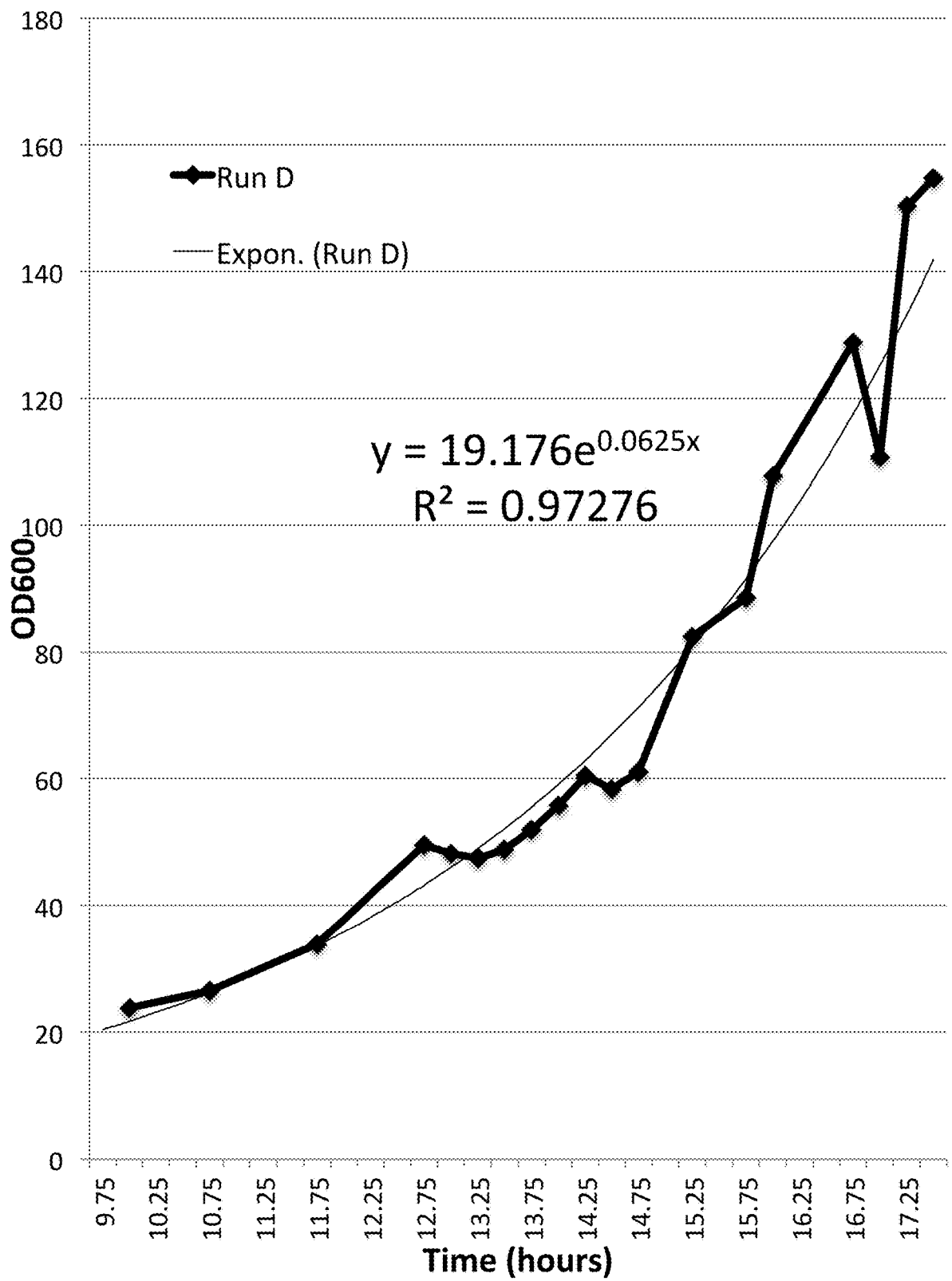
FIG. 2 shows the growth of *E. coli* EB0001(pBAD24-Infliximab_HC/pPRO33-Infliximab_LC) cells over time, measured as $OD_{600}$, for the exponential growth phase portion of fermentation Run D shown in FIG. 1. The growth curve was fit to an exponential curve to determine a specific growth rate indicator, 0.0625/hour, for the cells in this fermentation run.
Figure 3:
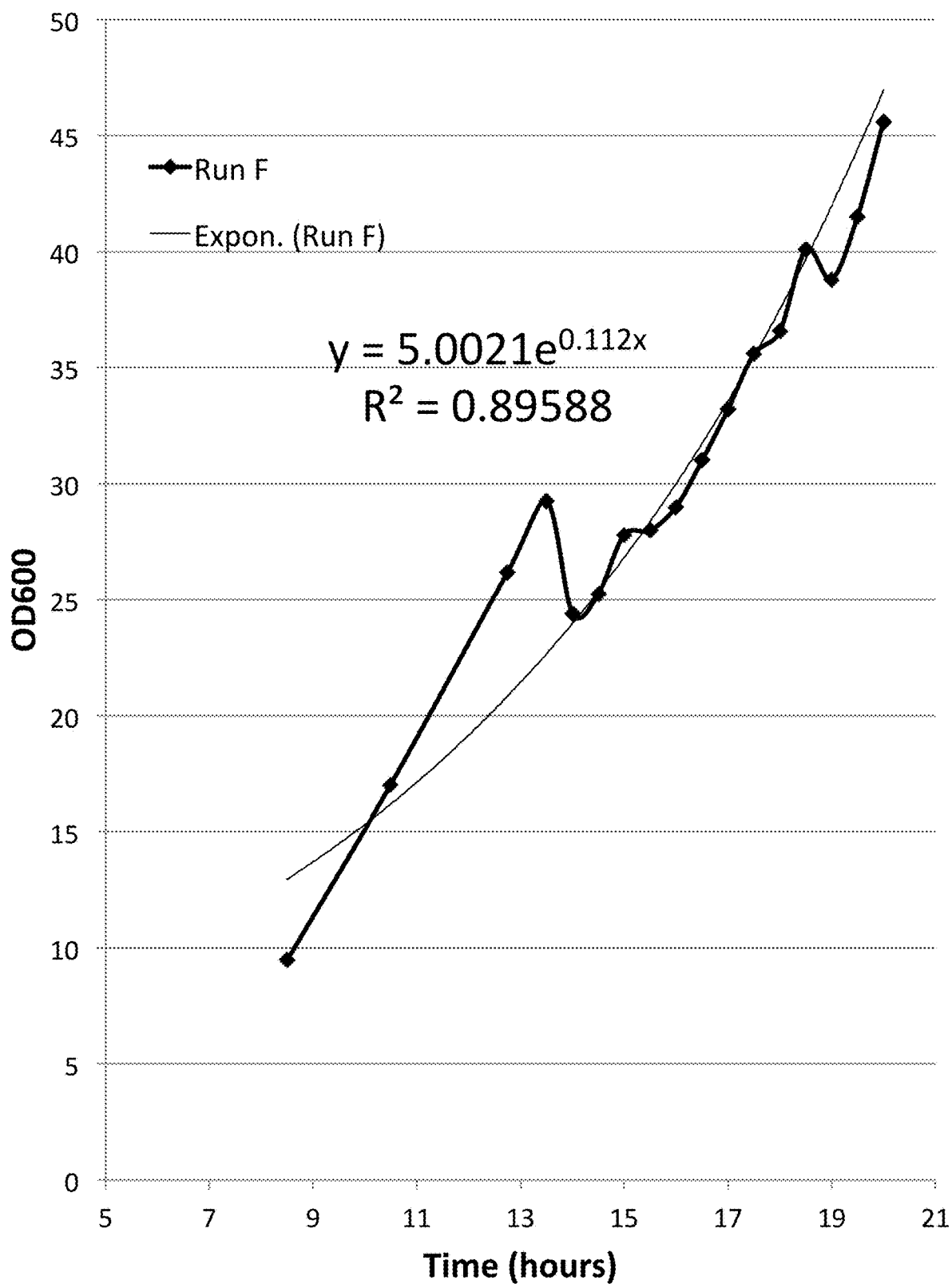
FIG. 3 shows the growth of *E. coli* EB0001(pBAD24-Infliximab_HC/pPRO33-Infliximab_LC) cells over time, measured as $OD_{600}$, for the exponential growth phase portion of fermentation Run F. The growth curve was fit to an exponential curve to determine a specific growth rate indicator, 0.112/hour, for the cells in this fermentation run.

The initial set points for the fermenter conditions were:
Agitation: 250 RPM, with cascade to high agitation at 1200 RPM
Temperature: 30.0 degrees C.
pH: 7.0
DO: 30.0%
Air: 100.0 L/min
Gas flow: 0.2 L/min, with cascade to high gas flow at 4 L/min
O$_2$ tank output pressure: ~150 (upper)/21 (lower) kPa Inoculum and Sampling:

a feeder culture of *E. coli* EB0001(pBAD24-Infliximab_HC/pPRO33-Infliximab_LC) host cells was prepared and used to inoculate the fermentation medium at an initial OD$_{600}$ of 0.1. After an initial fermentation period of 9 to 10 hours, samples of the fermentation culture were collected at 15-minute intervals and the OD$_{600}$ of the samples was determined. Growth rates for each fermentation run were determined by plotting the change in OD$_{600}$ over time for the exponential phase of the growth curve, and then determining the best-fit exponential curve, as shown in FIGS. 2 and 3. The value of the exponent for the best-fit exponential curve is one indicator of the specific growth rate per hour, and is referred to herein as a 'specific growth rate indicator'. Changes in biomass over time can also be used to determine specific growth rates. The approximate biomass (cell dry weight) at each assayed point is calculated: approximate biomass (g)=(OD$_{600}$÷2)×volume (L). In addition to specific growth rates, instantaneous growth rates for each successive point assayed during the fermentation run can be determined as follows. For a pair of time points at which the fermentation culture has been assayed, with 'time$_i$' being an earlier such time point than the time point the instantaneous growth rate at time$_i$ is calculated as: (ln(biomass at time$_i$)−ln(biomass at time$_{i-1}$))/(time$_i$−time$_{i-1}$). Instantaneous growth rates are often used to determine whether a fermentation culture is achieving growth rates comparable to a desired specific growth rate in response to an automated feeding schedule.

Run A:
Glucose was added to 2% at time points (hours): 11.09, 13.25, 14.8, and 15.5.

Glucose was added to 2.25% at 15.8 hours.

The cells demonstrated a specific growth rate indicator of 0.24/hour.

Run B:

$O_2$: high limit at 2 L/min, low limit at 0.2 L/min.

Glucose was added to 2% at time points (hours): 12, 14.6, 16.3, and 17.75.

Nitrogen feed solution (see below) was added at 12.6 hours.

$MgSO_4$ (6 ml of 1M $MgSO_4$ solution) was added at 15 hours.

The cells demonstrated a specific growth rate indicator of 0.21/hour.

Nitrogen feed: when the culture reached approximately 20 $OD_{600}$, 125 mL salt solution containing (amounts per 125 mL) was added:

1.25 g ammonium sulfate
3.25 g potassium phosphate (dibasic)
1.625 g sodium phosphate (monobasic, monohydrate)
0.25 g sodium citrate dehydrate
1.875 g potassium phosphate (monobasic)
30 ml 0.5 mg/ml Ferrous Sulfate
5 ml trace elements
pH to 7.0 with ammonium hydroxide Run C:

Glucose was added to 2% at time points (hours): 10.7, 13.1, 14.4, 15.35, 16.3, 16.8, 17.3, and 18.1.

$MgSO_4$ (6 ml of 1M $MgSO_4$ solution) was added at 12.9 hours.

Nitrogen feed solution (see above) was added automatically between 12.5 and 13.6 hours, at a pump output of 33% to deliver approximately 67 ml of nitrogen feed solution in 60.1 minutes.

A maximum OD of 124.68 was obtained in 18.5 hours with a specific growth rate indicator of 0.21/hour.

Run D:

$O_2$: high limit at 2 L/min, low limit at 0.2 L/min.

Glucose was added to 2% at time points (hours): 10.14, 11.9, 13, 14.26, 16.1, 17.25, 17.8, 18.3, and 18.8.

Glucose was added to 1% at time points (hours): 15.1, 15.45, and 15.83.

$MgSO_4$ (6 ml of 1M $MgSO_4$ solution) was added at 12.8 hours.

Nitrogen feed solution (see above) was added automatically between 12.5 and 13.6 hours, as in Run C.

A maximum OD of 167.2 was obtained in 18.25 hours, with a specific growth rate indicator of 0.0625/hour (see FIGS. 1 and 2).

Run E:

Oxygen tank pressure brought down to 10.0-8 kPa.

$O_2$: high limit initially set at 20 L/min, then to 40 L/min mid-run; low limit at 0.2 L/min.

$MgSO_4$ (6 ml of 1M $MgSO_4$ solution) was added at 13.3 hours.

Glucose as a 40% solution was added automatically, starting at 10.25 hours, according to the exponential equation X (output %)=6.2947 exp (0.2524 (EFT−10.25)), where 'EFT' is elapsed fermentation time.

Nitrogen feed solution (see above) was added automatically between 12.5 and 13.6 hours, as in Runs C and D.

A maximum OD of 132.1 was obtained in 19.0 hours, with a specific growth rate indicator of 0.2393/hour.

Run F:

In Run F, the amounts of the following two components of the Fermentation Media were changed:

20 g soytone (2%)
10 g yeast extract (1%)

O2 Tank settings: Output pressure: ~10-8 kPa $O_2$: high limit initially set at 20 L/min, then to 40 L/min mid-run; low limit at 0.2 L/min.

The nitrogen feed solution was changed from that shown in Run B, in that the ferrous sulfate and trace elements were removed from the solution; these compounds were added in the glucose feed instead. Two periods of automatic nitrogen feeding were performed, at 11.75-12.75 hours and at 19.25-20.25 hours, with a 27% pump output.

In this run, the glucose feed solution was changed to a buffered 70% glucose solution:

200 ml 70% glucose in a 250-ml bottle and autoclave for 20 min at 121° C.

Add 140 g glucose to 93 ml water and autoclave for 20 min at 120° C. Store at room temperature.

Complete the "glucose feed" by adding the following components:

8.0 mL 50% MgSO4 solution
  Dissolve 50 g MgSO4-7×H2O in 71 mL MilliQ double-distilled H2O. Filter sterilize and store at room temperature.
2.0 mL 1000× trace metal solution
0.6 mL 50 mg/mL ferrous sulfate, heptahydrate The equation to determine automated glucose feed rates was also changed to X (output %)=2.1708 exp (0.3459 (EFT−10.25)) to reflect the use of a 70% glucose solution. A maximum OD of 45.6 was obtained in 20.0 hours, with a specific growth rate indicator of 0.112/hour.

C. Induction of Expression and Purification of Expressed Infliximab

Smaller-volume growth and induction experiments with *E. coli* EB0001(pBAD24-Infliximab_HC/pPRO33-Infliximab_LC) host cells, for example in 200- to 500-ml shake flasks and generally as described in Example 3 below, are used to determine optimal growth times and inducer concentrations for expression of infliximab by the host cells.

*E. coli* EB0001(pBAD24-Infliximab_HC/pPRO33-Infliximab_LC) host cells are grown to high cell density as described above, until the cells reach a suitable growth phase for induction of protein expression, which is generally performed when cells have reached or are nearing the end of the exponential growth phase. For example, an inoculum of these cells in fermentation media, producing an initial $OD_{600}$ of 0.1, is grown in a fermenter until the cell culture reaches an $OD_{600}$ between 80 and 90; at a specific growth rate of approximately 0.15/hour, with growth taking roughly 24 hours. Host cells such as the *E. coli* EB0001(pBAD24-Infliximab_HC/pPRO33-Infliximab_LC) host cells can also be induced at higher cell densities, for example up to an $OD_{600}$ of 120 or more, by adjusting the feeding conditions described above, producing higher cell densities at the end of the exponential growth phase. At this point the inducers L-arabinose and propionate are introduced into the fermentation media, at concentrations determined by smaller-volume inducer titration experiments, with application of an appropriate scaling factor, which is less than 1. On this basis, the optimal concentrations of L-arabinose and propionate for induction of *E. coli* EB0001(pBAD24-Infliximab_HC/pPRO33-Infliximab_LC) host cell fermentation cultures are in the range of 1 to 266 micromolar (approximately 0.000015 to 0.004%) per OD unit of cells, and more specifically 6 to 67 micromolar (approximately 0.00009 to 0.001%) per OD unit of cells for L-arabinose, and 1 to 100 mM per OD unit of cells, and more specifically 5 to 50 mM per OD unit of cells for propionate.

The host cells are allowed to grow under inducing conditions for a length of time sufficient to produce the desired protein, with longer growth times used to produce proteins having longer polypeptide chains or a more complex structure, such as a multimeric structure; for the production of infliximab, the host cells are allowed to grow for 14-24 hours post-induction. The fermentation culture is then centrifuged at 4300 RPM for seven minutes to harvest the cells. The host cells containing infliximab in the cytoplasm can be frozen at that point for storage and/or transport, or can be lysed to release the expressed protein. Host cells can be lysed using known chemical and enzymatic methods, for example by resuspending the cells in a solution containing lysozyme. The *E. coli* EB0001(pBAD24-Infliximab_HC/pPRO33-Infliximab_LC) host cells are preferrably lysed by mechanical methods, such as cell disruption using a Microfluidics model LV1 microfluidizer for volumes up to 60 ml, or a Microfluidics model M-110Y microfluidizer for volumes greater than 60 mL (Microfluidics International Corp., Westwood, Massachusetts). Optionally, for quantification of expressed proteins using assays such as capillary electrophoresis Western blots, as described below, protein can be separated from cell membranes and other insoluble components in the mixture of lysis products using an extraction solution comprising Triton X-100 (0.5% to 15%; for most applications 1% to 8%) and urea (0.1M to 8M; for most applications 1M to 5M). The most effective concentrations of Triton X-100 and urea in the extraction solution will vary depending on the type of protein to be extracted and other factors, so testing different concentrations would be advantageous. This optional extraction procedure is not sufficient to solubilize inclusion bodies. Centrifugation at 20,000×g for 15 minutes at room temperature is then used to separate out the insoluble fraction, and the supernatant containing soluble protein including the expressed infliximab is collected.

D. Characterization of Expressed Infliximab

The infliximab antibodies are detected and quantified using a capillary electrophoresis Western blot, run on a WES system (ProteinSimple, San Jose, California), according to the manufacturer's instructions. Soluble protein extracts are loaded into the capillary set, proteins are electrophoretically separated by size, and then the infliximab antibodies in the samples are detected with a blocking step (instead of the use of a primary antibody), and incubation with an HRP-conjugated goat anti-human secondary antibody that recognizes human antibody heavy and light chains. Antibody detection is accomplished by addition of the chemiluminescent substrate to the capillary and the direct capture of the light emitted during the enzyme-catalyzed reaction. Molecular weight estimates are calculated using a standard curve generated using six biotinylated proteins ranging from 12 k to 230 kDa for each run. Fluorescent standards are included in the sample loading buffer, giving each sample an internal standard that is used to align the sample with the molecular weight standard.

To determine the amount of protein present at a given molecular weight, known amounts of a protein standard are run in some of the capillaries. In this case, serial dilutions are prepared of commerically available infliximab having a known protein concentration, starting for example at 10 micrograms/mL and diluted down to 1.0 nanograms/mL. Approximately five WES system capillaries are used to run the serial dilution. For each infliximab protein band in both the experimental and the serial dilution capillaries, a curve is generated by the WES system software representing the protein band's chemiluminescence intensity, and the area under each curve is evaluated, with a standard curve of these areas plotted for the infliximab protein bands in the infliximab serial dilution capillaries. To determine the concentration of the experimental samples, the area under each curve representing the chemiluminescence intensity of an experimental infliximab sample can the compared to the standard curve generated for the samples of known infliximab concentration.

The infliximab antibodies can be further purified as described in Example 5, and additional characterization of the infliximab antibodies is described in Example 6 (measurement of antibody binding affinity) and Example 7 (characterizing the disulfide bonds present in coexpression products).

Example 2

Production of Soluble Protein (Proinsulin Glargine) in Cells with Oxidizing Cytoplasm, Grown to High Cell Densities A. Preparation of EB0001(pSOL-Proglargine/Erv1p) Cells.

Figure 4:
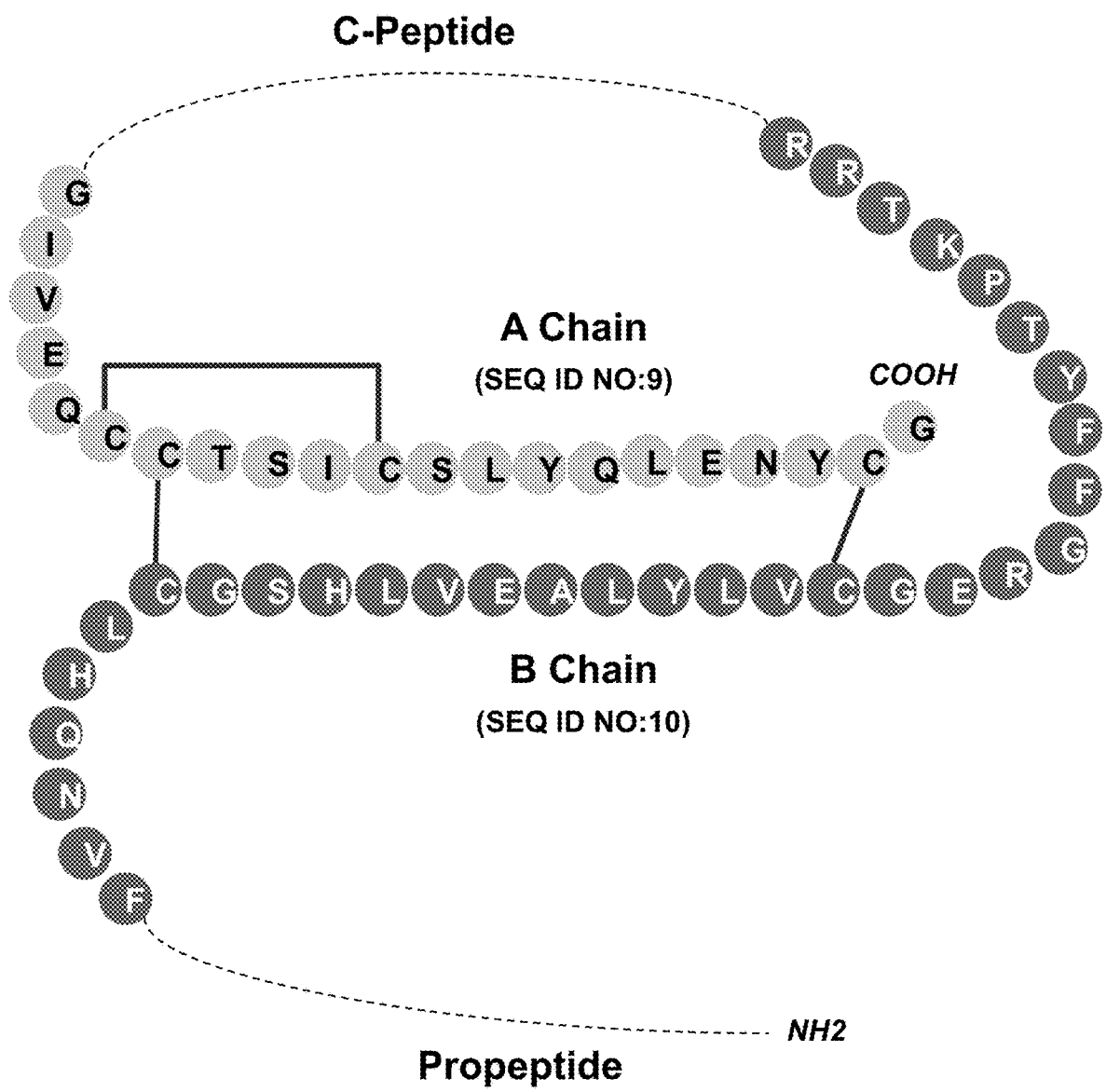
FIG. 4 is a schematic representation of a proinsulin glargine polypeptide. The amino acids of the A and B chains are shown as light gray and dark gray circles, respectively. The N-terminal propeptide and the C-peptide (or 'connecting peptide') that connects the A and B chains are shown as dashed lines. The solid dark gray lines between cysteine residues in the A and B chains, and connecting two cysteines within the A chain, represent the disulfide bonds present in correctly folded mature insulin glargine.

The form of insulin glargine that was expressed lacks the signal sequence that is present in preproglargine, and will be referred to herein as proglargine. The proglargine polypeptide that was expressed has the following structure, and is shown schematically in FIG. 4: an N-terminal propeptide, the insulin glargine B chain (SEQ ID NO:10), a connecting C-peptide, and the insulin glargine A chain (SEQ ID NO:9) at its C-terminus. The N-terminal propeptide portion of the insulin glargine polypeptide comprises an N-terminal methionine residue and an arginine residue as the C-terminal residue of the N-terminal propeptide, located immediately upstream of the insulin glargine B chain (SEQ ID NO:10), so that tryptic cleavage releases the N-terminal propeptide from the B chain. Similarly, the insulin glargine B chain (SEQ ID NO:10) and the C-peptide each also have an arginine residue as the C-terminal residue of those portions of the proglargine polypeptide; as a result, digestion with trypsin also releases the C-peptide from the insulin glargine B and A chains.

The pSOL expression vector (SEQ ID NO:3), also described in published US patent application US2015353940A1, has two multiple cloning sites: one downstream of the L-arabinose-inducible araBAD promoter, and another downstream of the propionate-inducible prpBCDE promoter. A polynucleotide encoding the above proglargine polypeptide was cloned into the pSOL expression vector (SEQ ID NO:3) downstream of the araBAD promoter. A polynucleotide (SEQ ID NO:17), encoding the yeast Erv1p polypeptide (SEQ ID NO:16, see also GenPept database, accession no. NP_011543.4) and optimized for expression in *E. coli*, was cloned into pSOL downstream of the prpBCDE promoter. The resulting pSOL-proglargine/Erv1p expression vector was transformed into EB0001 cells (also called *E. coli* ASE(DGH) cells, described in Example 1 above) by heat shock at 42 degrees C., followed by incubation at 37 degrees C. overnight, to create EB0001 (pSOL-proglargine/Erv1p) cells.

B. Growth of EB0001(pSOL-Proglargine/Erv1p) Cells.

The combination of EB0001 host cells with the expression vector pSOL-proglargine/Erv1p is also referred to as AbS0092. The *E. coli* EB0001(pSOL-proglargine/Erv1p) host cells were grown to high cell densities, greater than 170 $OD_{600}$, and produced soluble proglargine with properly formed disulfide bonds.

Fermentation Equipment and Conditions.

The EB0001(pSOL-proglargine/Erv1p) host cells were grown in a DASGIP fermentation system (Eppendorf North America, Hauppauge, New York) in two separate 250-ml DASbox fermentation vessels, which are further described in Example 1. The bioreactors used for these host cells were bioreactor 3 ('BR3') and bioreactor 4 ('BR4'); the cells in each bioreactor were grown under conditions designed to minimize any differences in the growth of the cells when compared to those in the other bioreactor. The bioreactors were calibrated as follows:

|  | BR3: | BR4: |
| --- | --- | --- |
| pH offset (pH): | 0.624 | 0.511 |
| pH slope (%): | 100.752 | 100.746 |
| DO offset (nA): | 0.009 | 0.008 |
| DO slope (nA): | 55.95 | 60.82 |

Fermentation included cascaded dissolved oxygen (DO) control, with the following varying conditions: agitation (400-1600 rpm), concentration of added oxygen ('XO2', 21-100%), with total input gas flow at 6-12 sLph. The fermentation conditions for the initial growth stage were 30.0 degrees C., DO 30%, pH 7.0, growth feed with 70% glucose at an initial feed rate of 0.6 mL/hr, for a set growth rate of 0.15/hr. The fermentation conditions for the induction stage were 27.0 degrees C., DO 30%, pH 7.0, induction feed with 70% glycerol at an induction feed coefficient of 0.15 mL/$g_{DCW}$·hr ('DCW' is dry cell weight).

Fermentation Media.

Fermentation medium; pre-sterilization components, concentration in g/L per 90 mL volume added to each bioreactor:

| | |
| --- | --- |
| Potassium phosphate (monobasic) | 14.8 |
| Potassium citrate tribasic (monohydrate) | 3.3 |
| Ammonium sulfate | 4.4 |
| Sodium chloride | 2.2 |
| Yeast extract | 11.1 |

Modified Korz trace metals (100× stock); combine components below, where final concentration is shown in g/L, and filter sterilize:

| | |
| --- | --- |
| $CoCl_2 \cdot 6H_2O$ | 0.25 |
| $MnCl_2 \cdot 4H_2O$ | 1.5 |
| $CuSO_4 \cdot 5H_2O$ | 0.22 |
| $H_3BO_3$ | 0.3 |
| $Na_2MoO_4 \cdot 2H_2O$ | 0.25 |
| $ZnSO_4 \cdot 7H_2O$ | 1.7 |

Fermentation medium; post-sterilization components (sterile stock concentration), amount in mL added to reach total volume of ca. 100 mL in each bioreactor:

| | |
| --- | --- |
| Glucose (700 g/L) | 1.4 |
| EDTA (100× stock, 0.84 g/L) | 1.0 |
| Modified Korz trace metals (100× stock) | 1.0 |
| Ferrous ammonium sulfate (40 g/L) | 0.8 |
| 1:5 diluted magnesium sulfate heptahydrate (500 g/L) | 1.3 |
| Sterile Antifoam 204, 10% dissolved in 70% ethanol/30% $H_2O$ (Sigma-Aldrich, St. Louis, Missouri) | 0.3 |
| 1:10 diluted kanamycin (50 g/L) | 1.0 |
| Calcium chloride (200 g/L) | 1.0 |

Growth feed; components (sterile stock concentration), amount in mL:

| | |
| --- | --- |
| Glucose (700 g/L) | 500 |
| EDTA (100× stock, 0.84 g/L) | 8.5 |
| Modified Korz trace metals (100× stock) | 9.0 |
| Ferrous ammonium sulfate (40 g/L) | 8.8 |
| Magnesium sulfate heptahydrate (500 g/L) | 25.0 |
| Kanamycin (50 g/L) | 0.50 |
| Yeast extract (250 g/L) | 17.5 |

Induction feed; components (sterile stock concentration), amount in mL:

| | |
| --- | --- |
| Glycerol (700 g/L) | 500 |
| EDTA (100× stock, 0.84 g/L) | 8.50 |
| Modified Korz trace metals (100× stock) | 9.00 |
| Ferrous ammonium sulfate (40 g/L) | 8.75 |
| Magnesium sulfate heptahydrate (500 g/L) | 25.0 |
| Kanamycin (50 g/L) | 0.50 |
| Arabinose (500 g/L) | 6.0 |

10× Tremendous Broth ('10×TB'):

Add the following to 90 mL distilled $H_2O$: 12 g soytone, 24 g yeast extract. Adjust to 100 mL with distilled $H_2O$. Sterilize by autoclaving. Allow to cool to room temperature.

Fermentation Procedure.

A feeder culture of EB0001(pSOL-proglargine/Erv1p) host cells, grown in LB medium with 10 g/L glucose to a final cell density of $OD_{600}$ 2.44, was used to inoculate the fermentation processes in each bioreactor. A 4.1-mL aliquot of these host cells were added to the ca. 100 mL of media in each bioreactor so that the initial optical density reading would be ca. $OD_{600}$ 0.1.

The cells were grown under the growth stage conditions (30.0 degrees C., DO 30%, pH 7.0, growth feed containing 70% glucose at an initial feed rate of 0.6 mL/hr, for a set growth rate of 0.15/hr) for 26 hours, and were sampled ($OD_{600}$ 136.4 and 131.2, respectively). Immediately prior to the start of induction, 5 mL of 10× Tremendous Broth was added to each bioreactor. Induction was initiated; the fermentation conditions were set to the induction stage conditions: 27.0 degrees C., DO 30%, pH 7.0, and induction feed containing 70% glycerol at an induction feed coefficient of 0.15 mL/$g_{Dcw}$/hr. The induction feed also contained the inducer L-arabinose, at a concentration calculated as follows from the total volume of components added to create the induction feed:

[L-arabinose] in induction feed: (6.0 mL×500 g/L)/
558 mL=5.4 g/L

The host cells in each bioreactor were sampled again at 27, 37, 39, 42, and 45 hours total fermentation time; these time points when expressed in terms of elapsed induction time (EIT(hrs)) are 0, 10, 12, 15, and 18.

TABLE C

Optical density ($OD_{600}$), flow rate (F), volume (V), cumulative grams of L-arabinose added ($g_{ara}$), L-arabinose concentration ([ara]), and L-arabinose concentration/$OD_{600}$ ([ara]/$OD_{600}$) for BR3, BR4 as a measure of elapsed induction time (EIT).

| EIT (hrs) | $OD_{600}$ | F (mL/hr) | V (mL) | $g_{ara}$ | [ara] (g/L) | [ara]/$OD_{600}$ (%/$OD_{600}$) | [ara]/$OD_{600}$ (µM/$OD_{600}$) |
|---|---|---|---|---|---|---|---|
| 0 | 140.8, | 1.90, | 179.8, | 0, | 0, | 0, | 0, |
|   | 137.6 | 1.82 | 176.3 | 0 | 0 | 0 | 0 |
| 10 | 170.8, | 2.57, | 200.8, | 0.103, | 0.512, | 0.000300, | 20.0, |
|   | 158.0 | 2.33 | 196.3 | 0.099 | 0.502 | 0.000318 | 21.2 |
| 12 | 172.4, | 2.66, | 205.8, | 0.131, | 0.636, | 0.000369, | 24.6, |
|   | 173.2 | 2.59 | 199.3 | 0.124 | 0.621 | 0.000359 | 23.9 |
| 15 | 178.0, | 2.85, | 213.8, | 0.174, | 0.814, | 0.000457, | 30.5, |
|   | 164.4 | 2.56 | 207.3 | 0.166 | 0.800 | 0.000487 | 32.4 |
| 18 | 174.4, | 2.89, | 220.8, | 0.220, | 0.999, | 0.000573, | 38.2, |
|   | 165.6 | 2.65 | 213.3 | 0.207 | 0.973 | 0.000588 | 39.1 |

Figure 5:
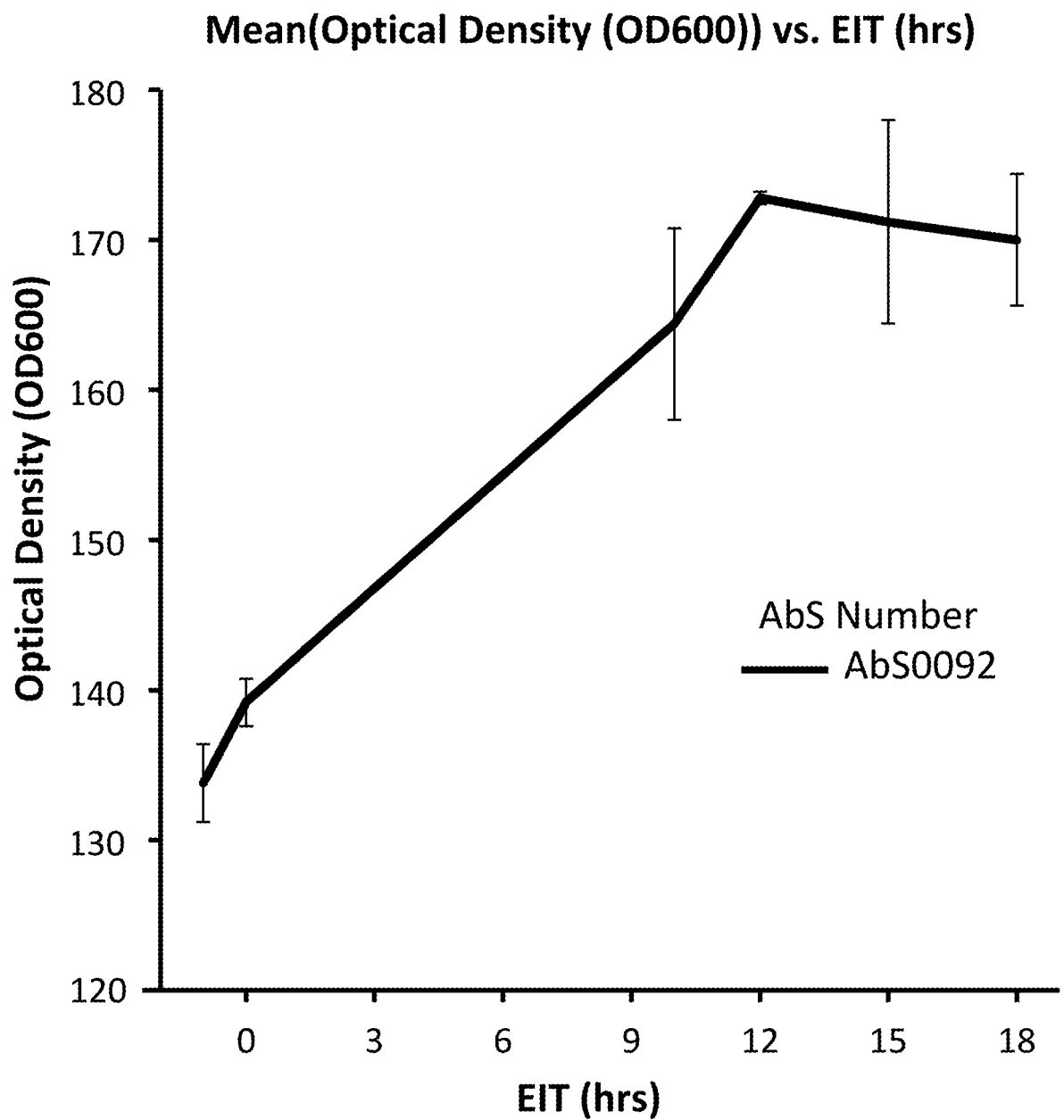
FIG. 5 shows the growth of EB0001(pSOL-proglargine/Erv1p) cells, also referred to as strain AbS0092, measured as optical density at 600 nm ($OD_{600}$). Cell growth was measured for the period of time (EIT or Elapsed Induction Time) in which the EB0001(pSOL-proglargine/Erv1p) cells were induced to express proinsulin glargine. The time point at 0 hours indicates the time at which induction was started. The points plotted are the average of optical density measurements taken from two separate bioreactors; the error bars indicate the range of values at each time point.

The mean optical densities (the average of the two $OD_{600}$ readings, one from each bioreactor) observed at each time point are shown graphically in FIG. 5, with the time points labeled in terms of elapsed induction time (EIT(hrs)). During the fermentation period shown in FIG. 5, the host cells reached cell densities of $OD_{600}$ 178.0 (BR3) and 173.2 (BR4).

The values in the columns of Table C were calculated as follows:

The flow rate (F) in mL/hr is the flow rate of induction feed with inducer set manually based on an induction feed coefficient of 0.15 mL/$g_{DCW}$/hr and OD measurement.

The volume (V) in mL is the volume of fermentation medium in the bioreactor, calculated from data generated by the DASbox fermenter system and taking into account the starting volume; minus the volume of media lost during autoclaving; plus any additions that the bioreactor made, such as growth feed, induction feed, and base and/or acid; plus the volume of nutrient solution (TB) added; minus the total volume of cumulative samples removed.

The cumulative grains of L-arabinose added ($g_{ara}$) in grams is calculated using the concentration of L-arabinose in the induction feed as calculated above, 5.4 g/L, multiplied by the flow rate (F) in mL/hr during the time period preceding the time of sampling, multiplied by the total duration of the induction feed (EIT) in hr, then divided by 1000 mL/L. For example, for BR3, the cumulative grams of L-arabinose added ($g_{ara}$), at EIT=10, is 5.4 g/L×1.90 mL/hr× 10 hr÷1000 mL/L=0.103 g.

The L-arabinose concentration ([ara]) in g/L is the grams of L-arabinose added ($g_{ara}$) divided by the volume (V) in mL and multiplied by the conversion factor 1000 ml/L.

The L-arabinose concentration/$OD_{600}$ ([ara]/$OD_{600}$) is calculated by dividing the L-arabinose concentration ([ara]) in g/L or mg/L by the $OD_{600}$, then converting to % per $OD_{600}$ or mM per $OD_{600}$ or micromolar (µM) per $OD_{600}$ using the following conversion factors:

1 g/L=0.1%=6.661 mM L-arabinose 1 mg/L=0.0001%=6.661 micromolar L-arabinose

The samples taken from BR3 and BR4 at the above time points were analyzed to determine amounts of soluble proglargine produced, according to the methods described in Example 1.0 and 1.D above, with quantitation of the proglargine performed by capillary electrophoresis Western blot (WES system). The primary antibody used to detect proglargine was the mouse monoclonal antibody L6B10 (catalog number 8138, Cell Signaling Technologies; Danvers, Massachusetts,), and the HRP-conjugated anti-mouse secondary antibody was supplied by the manufacturer of the WES system (ProteinSimple, San Jose, California). At each of the time points sampled during the induction period, each bioreactor produced at least 0.87 g/L of proglargine, which when adjusted for cell density was at least 5.2 mg/L/$OD_{600}$.

At the end of 45 hours of total fermentation time, the host cells were harvested by centrifugation at 4300 RPM for seven minutes, and stored as frozen pellets.

C. Purification and Characterization of Proglargine Produced by Fermentation of EB0001(pSOL-Proglargine/Erv1p) Cells.

The stored host cell pellet from Bioreactor 3 is thawed, and 10 g wet cell pellet is suspended in 100 mL lysis buffer: 50 mM Tris, 8M urea, pH 7.5 with 4 microliters benzonase. The suspension is passed twice through a Microfluidics model LV1 microfluidizer (Microfluidics International Corp., Westwood, Massachusetts), with a 3×6 mL lysis buffer chase. The LV1 has a void volume and ca. 70-80% of the material makes it through in a single pass; passing through twice results in an average 1.5× lytic treatment of the cell suspension. The cell lysate is centrifuged at 20,000×g for 30 minutes at 4 degrees C. to precipitate the insoluble material, and the supernatant—also termed the soluble fraction—is collected and passed through a 2-micron filter.

The filtered soluble fraction is then passed over a 25-mL DEAE Sepharose Fast Flow (GE Healthcare Life Sciences, Pittsburgh, Pennsylvania) column, with an equilibration/wash buffer: 50 mM Tris, 8M urea, pH 7.5, and an elution buffer: 50 mM Tris, 8M urea, 1M NaCl, pH 7.5. Proteins are eluted using a 0-40% NaCl gradient over 15 CV (column volumes), followed by 100% NaCl over 5 CV. Fractions eluted from the DEAE column that contain the proglargine product, as detected on a non-reducing SDS-PAGE gel, are pooled and diluted with 2-3 volumes of 50 mM Tris pH 7.5 to reduce conductivity.

The pooled fractions containing proglargine are then passed over a 1.7-mL Mono Q column (GE Healthcare Life Sciences, Pittsburgh, Pennsylvania), with an equilibration/wash buffer: 50 mM Tris, 4M urea, pH 7.5 for 10 CV, and an elution buffer: 50 mM Tris, 4M urea, 1M NaCl, pH 7.5. Proteins are eluted using a 0-40% NaCl gradient (step 1) over 40 CV, followed by 100% NaCl over 10 CV (step 2). Fractions eluted from the Mono Q column that contain the proglargine product, as detected on a non-reducing SDS-PAGE gel, are pooled and concentrated to 3 mL using 3-kDa MWCO (molecular weight cut-off) centrifugal concentrators (Amicon Ultra-4 Centrifugal Filter Units, EMD Millipore, Billerica, Massachusetts).

In the final purification step, the concentrated proglargine fractions are passed over a 120-mL 16-by-600 Superdex 200-pg column (HiLoad, GE Healthcare Life Sciences, Pittsburgh, Pennsylvania), with an equilibration/wash buffer: 50 mM Tris, 4M urea, 200 mM NaCl, pH 7.5. Column fractions are again run on a non-reducing SDS-PAGE gel, and fractions containing the proglargine protein are pooled, concentrated using 3-kDa MWCO centrifugal concentrators, and buffer-exchanged into a formulation buffer of 10 mM potassium phosphate, 200 mM L-arginine, pH 6.8 for characterization by analytical reversed-phase chromatography and by mass spectroscopy.

Figure 6:
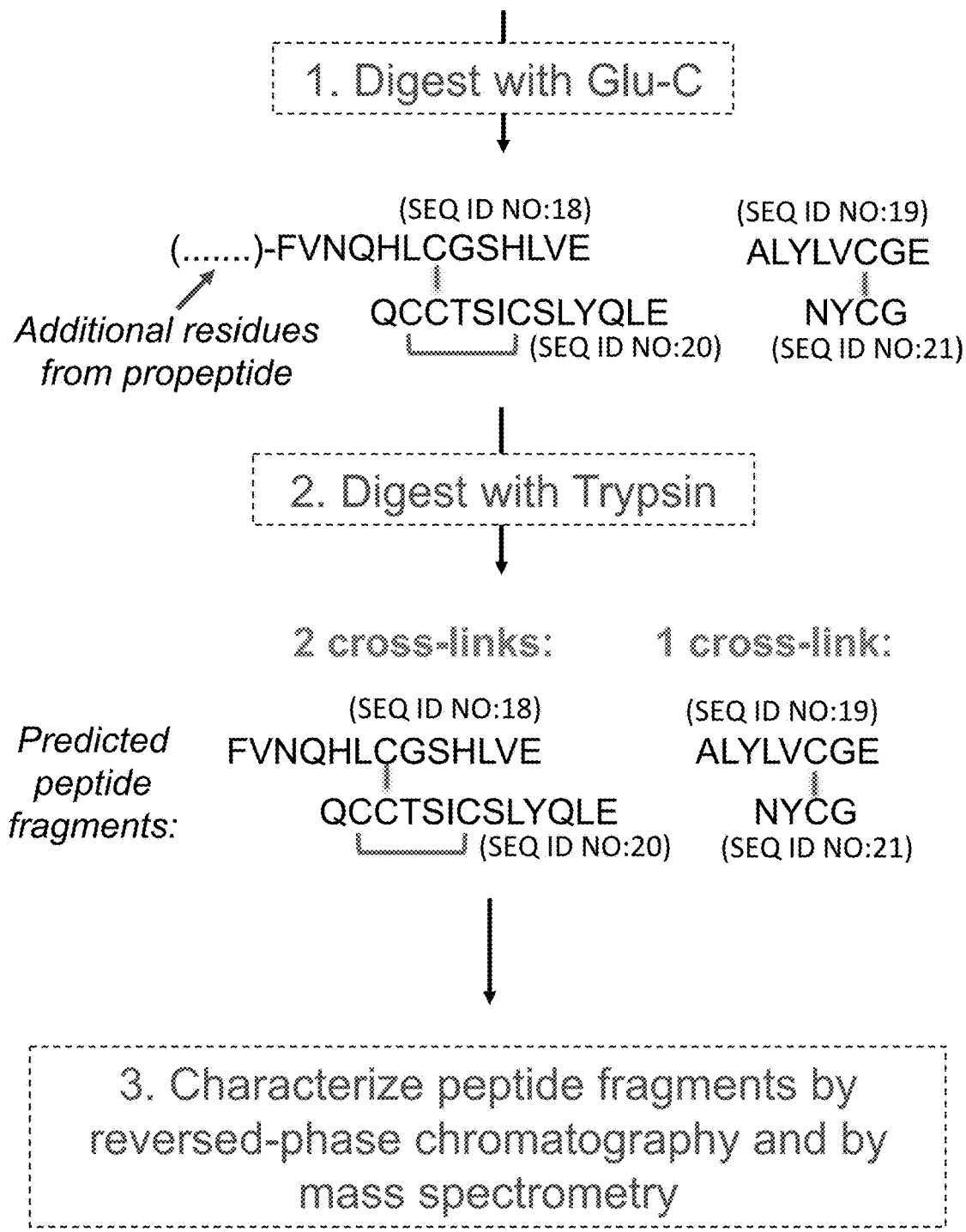
FIG. 6 is a schematic diagram showing the digestion of purified proinsulin glargine with glutamyl endopeptidase ('Glu-C') and with trypsin to generate crosslinked peptide fragments for characterization by reverse-phase chromatography and by mass spectometry. Disulfide bonds are represented by solid dark gray lines connecting cysteine residues.

The method of preparation of the purified proglargine samples for analysis by mass spectrometry (MS) is summarized in FIG. 6. The proglargine is first digested with glutamyl endopeptidase ('Glu-C'), which cleaves on the C-terminal side of glutamic acid residues. Proglargine fragments produced by this digestion are shown in FIG. 6, along with the locations of the disulfide bonds in properly assembled insulin glargine that would be expected to be present in these fragments. The fragment containing two disulfide bonds and the amino acid sequences of SEQ ID NO:18 and SEQ ID NO:20 also has additional amino acid residues from the N-terminal propeptide attached to the N-terminal residue of SEQ ID NO:18. A trypsin digest is performed to cleave the propeptide from the amino acid sequence of SEQ ID NO:18 prior to MS analysis, which is carried out as described in Example 7. A sample containing an insulin glargine standard known to have disulfide bonds in the proper positions, such as commercially available insulin glargine, is prepared for MS analysis in the same way as the purified proglargine samples produced by the methods of the invention.

The results of the MS analysis are shown in base-peak chromatograms. The MS peaks created by non-reduced proglargine peptide fragments are compared to those created by reduced and alkylated proglargine peptide fragments. Peaks corresponding to the disulfide-bonded proglargine fragments are expected to be seen in the non-reduced sample, but are absent in the reduced and alkylated sample. The presence and retention time of the peptide fragments containing two crosslinks and a single crosslink, respectively, is a determinant of the disulfide bond confirmation. The +4 charge state of the doubly crosslinked peptide is predominant and it elutes in the extracted ion chromatogram at a retention time similar to the properly folded insulin glargine standard. The +2 charge state of the singly crosslinked species is also observed as the predominant species and elutes as a single peak at a retention time comparable to the properly folded insulin glargine standard.

Purification of the proglargine and mass spectrometry results as described above are to provide confirmation that the proglargine produced by fermentation of the EB0001 (pSOL-proglargine/Erv1p) host cells is present in the soluble cell lysate fraction and has correctly formed disulfide bonds.

Example 3

Titration of Expression by Varying Inducer Concentration

To optimize production of a gene product using the expression systems of the invention, it is possible to independently adjust or titrate the concentrations of the inducers. Host cells containing expression constructs comprising inducible promoters—such as L-arabinose-inducible, propionate-inducible, L-rhamnose-inducible, or D-xylose-inducible promoters—are grown to the desired density for small-volume titrations (such as an $OD_{600}$ of approximately 0.5) in M9 minimal medium containing the appropriate antibiotics, then cells are aliquoted into small volumes of M9 minimal medium, optionally prepared with no carbon source such as glycerol, and with the appropriate antibiotics and varying concentrations of each inducer. Small-volume titrations can be performed in 200- to 500-ml shake flasks. The concentration of L-arabinose, L-rhamnose, or D-xylose necessary to induce expression is typically less (and is often substantially less) than 0.02% per OD unit of cells. In a titration experiment, the tested concentrations of L-arabinose can range from 2% to 1.5%, 1%, 0.5%, 0.2%, 0.1%, 0.05%, 0.04%, 0.03%, 0.02%, 0.01%, 0.005%, 0.002%, 0.001%, 0.0005%, 0.0002%, 0.0001%, 0.00005%, 0.00002%, 0.00001%, 0.000005%, 0.000002%, 0.000001%, 0.0000005%, 0.0000002%, 0.0000001%, 0.00000005%, 0.00000002%, and 0.00000001%, all per OD unit of cells. A concentration of 66.61 micromolar L-arabinose corresponds to 0.001% L-arabinose. An alternative titratation experiment for L-arabinose, L-rhamnose, or D-xylose would be to test the following concentrations, expressed in terms of molarity: 250 mM, 100 mM, 50 mM, 25 mM, 10 mM, 5 mM, 2.5 mM, 1.0 mM, 500 micromolar, 250 micromolar, 100 micromolar, 75 micromolar, 50 micromolar, 25 micromolar, 10 micromolar, 5.0 micromolar, 2.5 micromolar, 1.0 micromolar, 500 nM, 250 nM, 100 nM, 50 nM, 25 nM, 10 nM, 5.0 nM, 2.5 nM, 1.0 nM, 500 pM, 250 pM, 100 pM, 50 pM, 25 pM, 10 pM, 5.0 pM, 2.5 pM, and 1.0 pM, all per OD unit of cells. For propionate, concentrations to be tested can range from 1 M to 750 mM, 500 mM, 250 mM, 100 mM, 75 mM, 50 mM, 25 mM, 10 mM, 5 mM, 1 mM, 750 micromolar, 500 micromolar, 250 micromolar, 100 micromolar, 50 micromolar, 25 micromolar, 10 micromolar, 5.0 micromolar, 2.5 micromolar, 1.0 micromolar, 500 nM, 250 nM, 100 nM, 50 nM, 25 nM, 10 nM, 5.0 nM, 2.5 nM, and 1.0 nM all per OD unit of cells.

For each concentration 'x' of L-arabinose (or L-rhamnose or D-xylose) that is tested, the concentration of a different inducer such as propionate, added to each of the tubes containing concentration 'x' of the first inducer, is varied in each series of samples. Alternatively, titration experiments can start at a 'standard' combination of inducer concentrations, which for host cells having a reduced level of gene function of at least one gene encoding a protein that metabolizes the inducer is 0.0015% (100 micromolar) of any of L-arabinose, L-rhamnose, or D-xylose per OD unit of cells, and/or 100 micromolar propionate per OD unit of cells. For host cells in which the proteins that metabolize the inducer are functional, the 'standard' combination of inducer concentrations is 0.0033% (220 micromolar) of any of L-arabinose, L-rhamnose, or D-xylose per OD unit of cells, and/or 83 mM propionate per OD unit of cells. Additional combinations of inducer concentrations that vary from that of the 'standard' combination are tested; in a series of titration experiments, the results from initial experiments can be used to 'fine-tune' the inducer concentrations used in later experiments. Similar titration experiments can be performed with any combination of inducers used in an expression system of the invention, including but not limited to L-arabinose, propionate, L-rhamnose, and D-xylose. After growth in the presence of inducers for 6 hours, the cells are pelleted, the desired product is extracted from the cells, and the yield of product per mass value of cells is determined by a quantitative immunological assay such as ELISA, or by purification of the product and quantification by UV absorbance at 280 nm.

It is also possible to titrate inducer concentrations using a high-throughput assay, in which the proteins to be expressed are engineered to include a fluorescent protein moiety, such as that provided by the mKate2 red fluorescent protein (Evrogen, Moscow, Russia), or the enhanced green fluorescent proteins from *Aequorea victoria* and *Bacillus cereus*. Another approach to determining the amount and activity of gene products produced by different concentrations of inducers in a high-throughput titration experiment, is to use a sensor capable of measuring biomolecular binding interactions, such as a sensor that detects surface plasmon resonance, or a sensor that employs bio-layer interferometry (BLI) (for example, an Octet® QK system from forteBIO, Menlo Park, CA). If an antibody is available that binds with sufficient specificity to the gene product that is being expressed, the gene product can be detected and quantified using a capillary electrophoresis Western blot, such as that run on a WES system as described in Example 1 above.

Example 4

Determination of Solubility of Expression Products; Methods of Detecting Inclusion Bodies When methods of the invention are used to express gene products in the cytoplasm of host cells, the following procedures can be used to determine the degree to which the gene products are produced in the cell in soluble form.

The most straightforward approach is to lyse cells using any effective method, such as enzymatic lysis with lysozyme, as described in more detail in Example 8 below, or by cell disruption with a microfluidizer, as described in Example 1 above. The lysed cells are then centrifuged at 20,000×g for 15 minutes at room temperature to separate out the insoluble fraction as a pellet; the soluble fraction (the supernatant) is collected. Any method, such as ELISA or capillary electrophoresis Western blots, that can be used to detect the gene product, and preferably to specifically and quantifiably detect the gene product in each fraction, is employed and the amounts present in the soluble and insoluble fractions are compared. To test the effectiveness of this approach, endogenous host cell proteins, known to be soluble and present only in the host cell cytoplasm, are detected in both the soluble and insoluble fractions to determine whether the lysis and fractionation methods are trapping detectable amounts of soluble cytoplasmic products in the insoluble fraction.

It is also possible to directly assess whether gene products produced by methods of the invention are forming insoluble inclusion bodies. Inclusion bodies can be harvested by centrifugation of lysed host cells, stained with dyes such as Congo Red, and visualized using bright-field or cross-polarized light microscopy at modest (10×) magnification (Wang et al., "Bacterial inclusion bodies contain amyloid-like structure", PLoS Biol 2008 Aug. 5; 6(8): e195; doi: 10.1371/journal.pbio.0060195). When gene products are produced using the methods of the invention, should any appreciable amount of gene product be detected in the insoluble fraction as described above, any inclusion bodies present can be purified from the insoluble fraction and detected using light microscopy. Such inclusion bodies can also be resolubilized (Singh and Panda, "Solubilization and refolding of bacterial inclusion body proteins", J Biosci Bioeng 2005 April; 99(4): 303-310; Review) and tested, using specific binding assays or other methods of protein identification, for example, to determine if they include the gene products that are being produced.

Example 5

Purification of Antibodies

Antibodies produced by the expression systems of the invention are purified by centrifuging samples of lysed host cells at 10,000×g for 10 minutes to remove any cells and debris. The supernatant is filtered through a 0.45 micrometer filter. A 1-ml HiTrap MabSelect Protein A column (GE Healthcare Life Sciences, Pittsburgh, PA) is set up to achieve flow rates of 1 ml/min, and is used with the following buffers: binding buffer: 0.02 M sodium phosphate, pH 7.0; elution buffer: 0.1 M glycine-HCl, pH 2.7; and neutralization buffer: 1 M Tris-HCl, pH 9.0. The column is equilibrated with 5 column volumes (5 ml) of binding buffer, and then the sample is applied to the column. The column is washed with 5-10 column volumes of the binding buffer to remove impurities and unbound material, continuing until no protein is detected in the eluent (determined by UV absorbance at 280 nm). The column is then eluted with 5 column volumes of elution buffer, and the column is immediately re-equilibrated with 5-10 column volumes of binding buffer.

Example 6

Measurement of Antibody Binding Affinity

The antibody binding affinity, expressed as "Kd" or "Kd value", is measured by a radiolabeled antigen-binding assay (RIA) performed with the Fab version of an antibody of interest and its antigen as described by the following assay. Production of the Fab version of a full-length antibody is well known in the art. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, for example, Chen et al., "Selection and analysis of an optimized anti-VEGF antibody: crystal structure of an affinity-matured Fab in complex with antigen", J Mol Biol 1999 Nov. 5; 293(4): 865-881). To establish conditions for the assay, microtiter plates (DYNEX Technologies, Inc., Chantilly, Virginia) are coated overnight with 5 micrograms/ml of a capturing anti-Fab antibody (Cappel Labs, West Chester, Pennsylvania) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620; Thermo Scientific, Rochester, New York), 100 pM or 26 pM [$^{125}$I]-antigen are mixed with serial dilutions of a Fab of interest (e.g., consistent with assessment of the anti-VEGF antibody, Fab-12, in Presta et al., "Humanization of an anti-vascular endothelial growth factor monoclonal antibody for the therapy of solid tumors and other disorders", Cancer Res 1997 Oct. 15; 57(20): 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 microliters/well of scintillant (MICROSCINT-20™; PerkinElmer, Waltham, Massachusetts) is added, and the plates are counted on a TOPCOUNT™ gamma counter (PerkinElmer) for ten minutes. Concentrations of each Fab that give less than or equal to 20% of maximal binding are chosen for use in competitive-binding assays.

Alternatively, the Kd or Kd value is measured by using surface-plasmon resonance assays using a BIACORE®-2000 or a BIACORE®-3000 instrument (BIAcore, Inc., Piscataway, New Jersey) at 25° C. with immobilized antigen CMS chips at ~10 response units (RU). Briefly, carboxymethylated dextran biosensor chips (CMS, BIAcore Inc.) are activated with N-ethyl-N'-(3-dimethylamino-propyl)-carbodiimide hydrochloride (EDC) and N-hydroxysuccinimide (NHS) according to the supplier's instructions. Antigen is diluted with 10 mM sodium acetate, pH 4.8, to 5 micrograms/ml (~0.2 micromolar) before injection at a flow rate of 5 microliters/minute to achieve approximately 10 RU of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 microliters/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

Another method for determining the equilibrium dissociation constant (Kd) for antibody-antigen binding uses the Octet Red system (ForteBio, Pall Corporation, Port Washington, New York) (www.fortebio.com/octet-RED96.html). The initial measurement step determines the baseline, followed by loading the His-tagged antigen at a concentration of 25 nM onto Ni-NTA biosensors for 10 minutes in 1×KB+ buffer (0.01% BSA, 0.002% Tween-20 in PBS, pH7.4), followed by another baseline measurement step (1×KB+ buffer only for 2 minutes). The sensor is then dipped into a well containing antibody (the association step) for 10 minutes, followed by a 20-minute wash in 1×KB+ buffer to measure dissociation. The equilibrium dissociation constant (Kd) is calculated as the ratio of $k_{off}/k_{on}$, with the Octet software determining the $k_{off}$ and $k_{on}$ rates.

Example 7

Characterizing the Disulfide Bonds Present in Expression Products

The number and location of disulfide bonds in protein expression products can be determined by digestion of the protein with a protease, such as trypsin, under non-reducing conditions, and subjecting the resulting peptide fragments to mass spectrometry (MS) combining sequential electron transfer dissociation (ETD) and collision-induced dissociation (CID) MS steps (MS2, MS3) (Nili et al., "Defining the disulfide bonds of insulin-like growth factor-binding protein-5 by tandem mass spectrometry with electron transfer dissociation and collision-induced dissociation", J Biol Chem 2012 Jan. 6; 287(2): 1510-1519; Epub 2011 Nov. 22). Digestion of Expressed Protein.

To prevent disulfide bond rearrangements, any free cysteine residues are first blocked by alkylation: the expressed protein is incubated protected from light with the alkylating agent iodoacetamide (5 mM) with shaking for 30 minutes at 20° C. in buffer with 4 M urea. Alternatively and preferably, NEM is used as the alkylating reagent, with trypsin proteolysis in combination with reduction/alkylation conducted under denaturing conditions (6M GuaHCl). Following alkylation, the expressed protein is separated by non-reducing SDS-PAGE using precast gels. Alternatively, the expressed protein is incubated in the gel after electrophoresis with iodoacetamide or NEM, or without as a control. Protein bands are stained, de-stained with double-deionized water, excised, and incubated twice in 500 microliters of 50 mM ammonium bicarbonate, 50% (v/v) acetonitrile while shaking for 30 minutes at 20° C. Protein samples are dehydrated in 100% acetonitrile for 2 minutes, dried by vacuum centrifugation, and rehydrated with 10 mg/ml of trypsin or chymotrypsin in buffer containing 50 mM ammonium bicarbonate and 5 mM calcium chloride for 15 minutes on ice. Excess buffer is removed and replaced with 50 microliters of the same buffer without enzyme, followed by incubation for 16 hours at 37° C. or 20° C., for trypsin and chymotrypsin, respectively, with shaking. Digestions are stopped by addition of 3 microliters of 88% formic acid, and after brief vortexing, the supernatant is removed and stored at −20° C. until analysis. Alternative protein fragmentation methods, such as the use of endoproteinase Lys-C, glutamyl endopeptidase ('Glu-C'), or cyanogen bromide (CNBr) are used if trypsinolysis provides insufficient sequence coverage (<75%). Using the reducing agent TCEP (tris(2-carboxyethyl)phosphine) under acidic conditions in the presence of NEM provides access to fragments with partly intact disulfide linkages. The disulfide-intact digest map is compared to the reduced (DTT or TCEP) digest map.

Localization of Disulfide Bonds by Mass Spectrometry.

Peptides are injected onto a 1 mm×8 mm trap column (Michrom BioResources, Inc., Auburn, CA) at 20 microliters/minute in a mobile phase containing 0.1% formic acid. The trap car-tridge is then placed in-line with a 0.5 mm×250 mm column containing 5 mm Zorbax SB-C18 stationary phase (Agilent Technologies, Santa Clara, CA), and peptides separated by a 2-30% acetonitrile gradient over 90 minutes at 10 micro-liters/minute with a 1100 series capillary HPLC (Agilent Technologies); alternatively, a C18 column suitable for UPLC is used. Peptides are analyzed using a LTQ Velos linear ion trap with an ETD source (Thermo Fisher Scientific Inc., Waltham, Massachusetts). Electrospray ionization is performed using a Captive Spray source (Michrom Bioresources, Inc.), or preferably, an uncoated, pulled fused silica emitter (New Objective Inc., Woburn, Massachuetts) at 3.0 kV. Alternatively, analysis of medium-sized proteolytic fragments is performed using a Thermo LTQ-FT MS (7 Tesla) instrument, or a Synapt G2-Si quadrupole traveling wave ion mobility time-of-flight (ToF) mass spectrometer (Waters Corp., Milford, Massachusetts). Preferably, peptides are analyzed using an Orbitrap Fusion™ Tribrid™ mass spectrometer (Thermo Fisher Scientific).

Disulfide-linked peptides have charge states of +4 or greater following trypsinization due to the presence of two N-termini and two basic residues (arginine or lysine) at the carboxy termini. These disulfide-linked peptides are preferentially isolated by the Orbitrap Fusion™ instrument so that the disulfide bonds can be broken using ETD fragmentation.

Survey MS scans are followed by seven data-dependant scans consisting of CID and ETD MS2 scans on the most intense ion in the survey scan, followed by five MS3 CID scans on the first- to fifth-most intense ions in the ETD MS2 scan. CID scans use normalized collision energy of 35, and ETD scans use a 100 ins activation time with supplemental activation enabled. Minimum signals to initiate MS2 CID and ETD scans are 10,000, minimum signals for initiation of MS3 CID scans are 1000, and isolation widths for all MS2 and MS3 scans are 3.0 m/z. The dynamic exclusion feature of the software is enabled with a repeat count of 1, exclusion list size of 100, and exclusion duration of 30 seconds. Inclusion lists to target specific cross-linked species for collection of ETD MS2 scans are used. Separate data files for MS2 and MS3 scans are created by Bioworks 3.3 (Thermo Fisher Scientific) using ZSA charge state analysis. Matching of MS2 and MS3 scans to peptide sequences is performed by Sequest (V27, Rev 12, Thermo Fisher Scientific). The analysis is performed without enzyme specificity, a parent ion mass tolerance of 2.5, fragment mass tolerance of 1.0, and a variable mass of +16 for oxidized methionine residues. Results are then analyzed using the program Scaffold (V3_00_08, Proteome Software, Portland, OR) with minimum peptide and protein probabilities of 95 and 99% being used. Software tools for data interpretation also include Proteome Discoverer™ 2.0 with the Disulfinator node (Thermo Fisher Scientific). Peptides from MS3 results are sorted by scan number, and cysteine containing peptides are identified from groups of MS3 scans produced from the five most intense ions observed in ETD MS2 scans. The identities of cysteine peptides participating in disulfide-linked species are further confirmed by manual examination of the parent ion masses observed in the survey scan and the ETD MS2 scan.

Example 8

Isolation of Expression Products from Bacterial Cell Periplasm, from Spheroplasts, and from Whole Cells The expression system of the invention can be used to express gene products that accumulate in different compartments of the cell, such as the cytoplasm or periplasm. Host cells such as *E. coli* or *S. cerevisiae* have an outer cell membrane or cell wall, and can form spheroplasts when the outer membrane or wall is removed. Expressed proteins made in such hosts can be purified specifically from the periplasm, or from spheroplasts, or from whole cells, using the following method (Schoenfeld, "Convenient, rapid enrichment of periplasmic and spheroplasmic protein fractions using the new PeriPreps™ Periplasting Kit", Epicentre Forum 1998 5(1): 5; see www.epibio.com/newsletter/f5_1/f5_1pp.asp). This method, using the PeriPreps™ Periplasting Kit (Epicentre® Biotechnologies, Madison WI; protocol available at www.epibio.com/pdftechlit/107p10612.pdf), is designed for *E. coli* and other grain negative bacteria, but the general approach can be modified for other host cells such as *S. cerevisiae*.

1. The bacterial host cell culture is grown to late log phase only, as older cell cultures in stationary phase commonly demonstrate some resistance to lysozyme treatment. If the expression of recombinant protein is excessive, cells may prematurely lyse; therefore, cell cultures are not grown in rich medium or at higher growth temperatures that might induce excessive protein synthesis. Protein expression is then induced; the cells should be in log phase or early stationary phase.

2. The cell culture is pelleted by centrifugation at a minimum of 1,000×g for 10 minutes at room temperature. Note: the cells must be fresh, not frozen. The wet weight of the cell pellet is determined in order to calculate the amount of reagents required for this protocol.

3. The cells are thoroughly resuspended in a minimum of 2 ml of PeriPreps Periplasting Buffer (200 mM Tris-HCl pH 7.5, 20% sucrose, 1 mM EDTA, and 30 U/microliter Ready-Lyse Lysozyme) for each gram of cells, either by vortex mixing or by pipeting until the cell suspension is homogeneous. Note: excessive agitation may cause premature lysing of the spheroplasts resulting in contamination of the periplasmic fraction with cytoplasmic proteins.

4. Incubate for five minutes at room temperature. Ready-Lyse Lysozyme is optimally active at room temperature. Lysis at lower temperatures (0° C.–4° C.) requires additional incubation time; at such temperatures incubation times are extended 2- to 4-fold.

5. Add 3 ml of purified water at 4° C. for each gram of original cell pellet weight (Step 2) and mix by inversion.

6. Incubate for 10 minutes on ice.

7. The lysed cells are pelleted by centrifugation at a minimum of 4,000×g for 15 minutes at room temperature.

8. The supernatant containing the periplasmic fraction is transferred to a clean tube.

9. To degrade contaminating nucleic acids, OmniCleave Endonuclease is optionally added to PeriPreps Lysis Buffer. Inclusion of a nuclease will generally improve the yield of protein and the ease of handling of the lysates, but addition of a nuclease is undesirable in some cases: for example, the use of a nuclease should be avoided if residual nuclease activity or transient exposure to the magnesium cofactor will interfere with subsequent assays or uses of the purified protein. The addition of EDTA to the lysate to inactivate OmniCleave Endonuclease, likewise, may interfere with subsequent assay or use of the purified protein. If nuclease is to be added, 2 microliters of OmniCleave Endonuclease and 10 microliters of 1.0 M $MgCl_2$ are diluted up to 1 ml with PeriPreps Lysis Buffer (10 mM Tris-HCl pH 7.5, 50 mM KCl, 1 mM EDTA, and 0.1% deoxycholate) for each milliliter of Lysis Buffer needed in Step 10.

10. The pellet is resuspended in 5 ml of PeriPreps Lysis Buffer for each grain of original cell pellet weight.

11. The pellet is incubated at room temperature for 10 minutes (if included, OmniCleave Endonuclease activity will cause a significant decrease in viscosity; the incubation is continued until the cellular suspension has the consistency of water).

12. The cellular debris is pelleted by centrifugation at a minimum of 4,000×g for 15 minutes at 4° C.

13. The supernatant containing the spheroplast fraction is transferred to a clean tube.

14. If OmniCleave Endonuclease was added to the PeriPreps Lysis Buffer, 20 microliters of 500 mM EDTA is added for each milliliter of the resultant spheroplastic fraction, to chelate the magnesium (the final concentration of EDTA in the lysate is 10 mM). Following hydrolysis of nucleic acids with OmniCleave Endonuclease, lysates may contain substantial amounts of mono- or oligonucleotides. The presence of these degradation products may affect further processing of the lysate: for example, nucleotides may decrease the binding capacity of anion exchange resins by interacting with the resin.

The above protocol can be used to prepare total cellular protein with the following modifications. The cells pelleted in Step 2 can be fresh or frozen; at Step 4, the cells are incubated for 15 minutes; Steps 5 through 8 are omitted; at Step 10, 3 ml of PeriPreps Lysis Buffer is added for each gram of original cell pellet weight.

After preparation of periplasmic, or spheroplastic, or whole-cell protein samples, the samples can be analyzed by any of a number of protein characterization and/or quantification methods. In one example, the successful fractionation of periplasmic and spheroplastic proteins is confirmed by analyzing an aliquot of both the periplasmic and spheroplastic fractions by SDS-PAGE (two microliters of each fraction is generally sufficient for visualization by staining with Coomassie Brilliant Blue). The presence of unique proteins or the enrichment of specific proteins in a given fraction indicates successful fractionation. For example, if the host cell contains a high-copy number plasmid with the ampicillin resistance marker, then the presence of β-lactamase (31.5 kDa) mainly in the periplasmic fraction indicates successful fractionation. Other E. coli proteins found in the periplasmic space include alkaline phosphatase (50 kDa) and elongation factor Tu (43 kDa). The amount of protein found in a given fraction can be quantified using any of a number of methods (such as SDS-PAGE and densitometry analysis of stained or labeled protein bands, scintillation counting of radiolabeled proteins, enzyme-linked immunosorbent assay (ELISA), or scintillation proximity assay, among other methods.) Comparing the amounts of a protein found in the periplasmic fraction as compared to the spheroplastic fraction indicates the degree to which the protein has been exported from the cytoplasm into the periplasm.

Example 9

Measurement of the Strength of Promoters and the Homogeneity of Inducible Expression The strength of a promoter is measured as the amount of transcription of a gene product initiated at that promoter, relative to a suitable control. For constitutive promoters directing expression of a gene product in an expression construct, a suitable control could use the same expression construct, except that the 'wild-type' version of the promoter, or a promoter from a 'housekeeping' gene, is used in place of the promoter to be tested. For inducible promoters, expression of the gene product from the promoter can be compared under inducing and non-inducing conditions.

A. Measuring Promoter Strength Using Quantitative PCR to Determine Levels of RNA Transcribed from the Promoter The method of De Mey et al. ("Promoter knock-in: a novel rational method for the fine tuning of genes", BMC Biotechnol 2010 Mar. 24; 10: 26) is used to determine the relative strength of promoters in host cells that can be grown in culture. Host cells containing an expression construct with the promoter to be tested, and control host cells containing a control expression construct, are grown in culture in triplicate. One-ml samples are collected at $OD_{600}=1.0$ for mRNA and protein collection. Total RNA extraction is done using an RNeasy mini kit (QIAGEN, The Netherlands). The purity of RNA is verified on a FA-agarose gel as recommended by QIAGEN and the RNA concentration is determined by measuring the absorbance at 260 nm. Two micrograms of RNA is used to synthesize cDNA using a random primer and RevertAid H Minus M-MulV reverse transcriptase (Fermentas, Glen Burnie, Maryland). The strength of the promoter is determined by RT-qPCR carried out in an iCycler IQ® (Bio-Rad, Eke, Belgium) using forward and reverse primers designed to amplify the cDNA corresponding to the transcript produced from the promoter. (For this purpose, the De Mey et al. authors used the Fw-ppc-qPCR and Rv-ppc-qPCR primers, and the primers Fw-rpoB-qPCR and Rv-rpoB-qPCR from the control housekeeping gene rpoB.) SYBR GreenER qPCR supermix (Life Technologies, Grand Island, New York) is used to perform a brief UDG (uracil DNA glycosylase) incubation (50° C. for 2 min) immediately followed by PCR amplification (95° C. for 8.5 min; 40 cycles of 95° C. for 15 s and 60° C. for 1 min) and melting curve analysis (95° C. for 1 min, 55° C. for 1 min and 80 cycles of 55° C.+0.5° C./cycles for 10 s) to identify the presence of primer dimers and analyze the specificity of the reaction. This UDG incubation step before PCR cycling destroys any contaminating dU-containing products from previous reactions. UDG is then inactivated by the high temperatures during normal PCR cycling, thereby allowing the amplification of genuine target sequences. Each sample is performed in triplicate. The relative expression ratios are calculated using the "Delta-delta ct method" of PE Applied Biosystems (PerkinElmer, Forster City, California).

B. Measuring Inducible Promoter Strength and Homogeneity of Induction Using a Fluorescent Reporter Gene These experiments are performed using the methods of Khlebnikov et al. ("Regulatable arabinose-inducible gene expression system with consistent control in all cells of a culture", J Bacteriol 2000 December; 182(24): 7029-7034). Experiments measuring the induction of an inducible promoter are performed in C medium supplemented with 3.4% glycerol as a carbon source (Helmstetter, "DNA synthesis during the division cycle of rapidly growing Escherichia coli B/r", J Mol Biol 1968 Feb. 14; 31(3): 507-518). E. coli strains containing expression constructs comprising at least one inducible promoter controlling expression of a fluorescent reporter gene are grown at 37° C. under antibiotic selection to an optical density at 600 nm (OD600) of 0.6 to 0.8. Cells are collected by centrifugation (15,000×g), washed in C medium without a carbon source, resuspended in fresh C medium containing antibiotics, glycerol, and/or inducer (for the induction of gene expression) to an OD600 of 0.1 to 0.2, and incubated for 6 h. Samples are taken routinely during the growth period for analysis. Culture fluorescence is measured on a Versafluor Fluorometer (Bio-Rad Inc., Hercules, California) with 360/40-nm-wavelength excitation and 520/10-nm-wavelength emission filters. The strength of expression from an inducible promoter upon induction can be expressed as the ratio of the maximum population-averaged fluorescence (fluorescence/OD ratio) of the induced cells relative to that of control (such as uninduced) cells. To determine the homogeneity of induction within the cell population, flow cytometry is performed on a Beckman-Coulter EPICS XL flow cytometer (Beckman Instruments Inc., Palo Alto, California) equipped with an argon laser (emission at a wavelength of 488 nm and 15 mW) and a 525-nm-wavelength band pass filter. Prior to the analysis, sampled cells are washed with phosphate-buffered saline that had been filtered (filter pore size, 0.22 micrometers), diluted to an OD600 of 0.05, and placed on ice. For each sample, 30,000 events are collected at a rate between 500 and 1,000 events/s. The percentage of induced (fluorescent) cells in each sample can be calculated from the flow cytometry data.

Example 10

Determination of Polynucleotide or Amino Acid Sequence Similarity

Percent polynucleotide sequence or amino acid sequence identity is defined as the number of aligned symbols, i.e. nucleotides or amino acids, that are identical in both aligned sequences, divided by the total number of symbols in the alignment of the two sequences, including gaps. The degree of similarity (percent identity) between two sequences may be determined by aligning the sequences using the global alignment method of Needleman and Wunsch (*J. Mol. Biol.* 48:443, 1970), as implemented by the National Center for Biotechnology Information (NCBI) in the Needleman-Wunsch Global Sequence Alignment Tool, available through the website blast.ncbi.nlm.nih.gov/Blast.cgi. In one embodiment, the Needleman and Wunsch alignment parameters are set to the default values (Match/Mismatch Scores of 2 and −3, respectively, and Gap Costs for Existence and Extension of 5 and 2, respectively). Other programs used by those skilled in the art of sequence comparison may also be used to align sequences, such as, for example, the basic local alignment search tool or BLAST® program (Altschul et al., "Basic local alignment search tool", J Mol Biol 1990 Oct. 5; 215(3): 403-410), as implemented by NCBI at the blast.ncbi.nlm.nih.gov/Blast.cgi website, using the default parameter settings described. The BLAST algorithm has multiple optional parameters including two that may be used as follows: (A) inclusion of a filter to mask segments of the query sequence that have low compositional complexity or segments consisting of short-periodicity internal repeats, which is preferably not utilized or set to 'off', and (B) a statistical significance threshold for reporting matches against database sequences, called the 'Expect' or E-score (the expected probability of matches being found merely by chance; if the statistical significance ascribed to a match is greater than this E-score threshold, the match will not be reported). If this 'Expect' or E-score value is adjusted from the default value (10), preferred threshold values are 0.5, or in order of increasing preference, 0.25, 0.1, 0.05, 0.01, 0.001, 0.0001, 0.00001, and 0.000001.

In practicing the present invention, many conventional techniques in molecular biology, microbiology, and recombinant DNA technology are optionally used. Such conventional techniques relate to vectors, host cells, and recombinant methods. These techniques are well known and are explained in, for example, Berger and Kimmel, Guide to Molecular Cloning Techniques, Methods in Enzymology volume 152 Academic Press, Mc, San Diego, CA; Sambrook et al., Molecular Cloning—A Laboratory Manual (3rd Ed.), Vol. 1-3, Cold Spring Harbor Laboratory, Cold Spring Harbor, New York, 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, for example for cell isolation and culture and for subsequent nucleic acid or protein isolation, include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, NY; Gamborg and Phillips (Eds.) (1995) Plant Cell, Tissue and Organ Culture; Fundamental Methods Springer Lab Manual, Springer-Verlag (Berlin Heidelberg New York); and Atlas and Parks (Eds.) The Handbook of Microbiological Media (1993) CRC Press, Boca Raton, FL Methods of making nucleic acids (for example, by in vitro amplification, purification from cells, or chemical synthesis), methods for manipulating nucleic acids (for example, by site-directed mutagenesis, restriction enzyme digestion, ligation, etc.), and various vectors, cell lines, and the like useful in manipulating and making nucleic acids are described in the above references. In addition, essentially any polynucleotide (including labeled or biotinylated polynucleotides) can be custom or standard ordered from any of a variety of commercial sources.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

All cited references, including patent publications, are incorporated herein by reference in their entirety. Nucleotide and other genetic sequences, referred to by published genomic location or other description, are also expressly incorporated herein by reference.

SEQUENCES PRESENTED IN THE SEQUENCE LISTING

| SEQ ID NO: | Length: | Type: | Organism: | Description; 'Other Information' |
|---|---|---|---|---|
| 1 | 486 | PRT | Artificial Sequence | *Humicola insolens* protein disulfide isomerase (PDI) amino acid sequence, without signal peptide |
| 2 | 1487 | DNA | Artificial Sequence | Protein disulfide isomerase (PDI) expression construct |
| 3 | 5304 | DNA | Artificial Sequence | Dual-promoter vector, pSOL |
| 4 | 21 | PRT | *Homo sapiens* | Native human insulin, mature A chain |
| 5 | 30 | PRT | *Homo sapiens* | Native human insulin, mature B chain |
| 6 | 30 | PRT | Artificial Sequence | Insulin lispro, mature B chain |
| 7 | 30 | PRT | Artificial Sequence | Insulin aspart, mature B chain |
| 8 | 30 | PRT | Artificial Sequence | Insulin glulisine, mature B chain |
| 9 | 21 | PRT | Artificial Sequence | Insulin glargine, mature A chain |
| 10 | 32 | PRT | Artificial Sequence | Insulin glargine, mature B chain |
| 11 | 29 | PRT | Artificial Sequence | Insulin degludec, mature B chain; deletion of B30 threonine and modification of lysine at B29 with a hexadecanedioic acid molecule bound to B29 through an L-gamma-Glu linker |
| 12 | 29 | PRT | Artificial Sequence | Insulin detemir, mature B chain; deletion of B30 threonine and modification of lysine at B29 with a myristic acid molecule |
| 13 | 168 | PRT | Hog cholera virus (strain Alfort) | Hog cholera virus/classical swine fever virus (CSFV) N$^{pro}$ |
| 14 | 90 | PRT | *Sus scrofa* | Amino acids 21-110 of *Sus scrofa* carboxypeptidase B ('CPB') precursor |
| 15 | 91 | PRT | *Caenorhabditis elegans* | Small ubiquitin-related modifier (SUMO) |

-continued

| SEQ ID NO: | Length: | Type: | Organism: | Description; 'Other Information' |
|---|---|---|---|---|
| 16 | 189 | PRT | S. cerevisiae (strain S288c) | Saccharomyces cerevisiae (strain S288c) Erv1p |
| 17 | 570 | DNA | Artificial Sequence | Polynucleotide encoding Erv1p, optimized for expression in prokaryotes such as E. coli |
| 18 | 13 | PRT | Homo sapiens | Fragment of human insulin B chain produced by Glu-C and trypsin digests; amino acids 1-13 of SEQ ID NO: 5 |
| 19 | 8 | PRT | Homo sapiens | Fragment of human insulin B chain produced by Glu-C digest; amino acids 14-21 of SEQ ID NO: 5 |
| 20 | 13 | PRT | Homo sapiens | Fragment of human insulin A chain produced by Glu-C digest; amino acids 5-17 of SEQ ID NO: 4 |
| 21 | 4 | PRT | Artificial Sequence | Fragment of human insulin glargine A chain produced by Glu-C digest; amino acids 18-21 of SEQ ID NO: 9 |

What is claimed is:

1. A method of producing an insulin polypeptide with correctly-formed disulfide bonds, the method comprising:
   providing one or more host cells comprising at least one expression construct comprising at least one inducible promoter and at least one polynucleotide sequence encoding an insulin polypeptide to be transcribed from at least one said inducible promoter;
   wherein the host cells have an altered gene function of at least one gene that makes the reduction/oxidation environment of the host cell cytoplasm more oxidizing;
   growing the host cells until the host cells reach a density greater than 145 ($OD_{600}$);
   inducing expression of the insulin polypeptide with an inducer selected from the group consisting of L-arabinose, propionate, rhamnose, xylose, and lactose;
   lysing the host cells; and
   purifying the insulin polypeptide with correctly-formed disulfide bonds from a soluble cell lysate fraction.

2. The method of claim 1, wherein the at least one inducible promoter is selected from the group consisting of an L-arabinose-inducible promoter, a propionate-inducible promoter, a rhamnose-inducible promoter, a xylose-inducible promoter, and a lactose-inducible promoter.

3. The method of claim 2, wherein the at least one inducible promoter is selected from the group consisting of an araBAD promoter, a prpBCDE promoter, a rhaSR promoter, a xlyA promoter, and a lacZYA promoter.

4. The method of claim 1, further comprising adding an inducer to the host cells per host cell density ($OD_{600}$) unit, wherein the inducer is selected from the group consisting of: L-arabinose at a concentration between 200 micromolar and 1 pM; L-rhamnose at a concentration between 1 M and 1 pM; D-xylose at a concentration between 1 M and 1 pM; and propionate at a concentration between 1 M and 1 nM.

5. The method of claim 1 wherein the at least one gene that makes the reduction/oxidation environment of the host cell cytoplasm more oxidizing is selected from the group consisting of gor, gshA, gshB, and trxB.

6. The method of claim 5 wherein the host cells further have an altered gene function of ahpC, wherein the ahpC gene is ahpC$^\Delta$.

7. The method of claim 1 wherein the host cells further have a reduced level of gene function of at least one gene encoding a protein that metabolizes an inducer of at least one said inducible promoter.

8. The method of claim 7 wherein the at least one gene encoding a protein that metabolizes an inducer of at least one said inducible promoter is selected from the group consisting of araA, araB, araD, prpB, prpD, rhaA, rhaB, rhaD, xylA, and xylB.

9. The method claim 1 wherein the host cells have an alteration of gene function of at least one gene encoding a transporter protein for an inducer of at least one said inducible promoter.

10. The method of claim 9 wherein the at least one gene encoding a transporter protein is selected from the group consisting of araE, araF, araG, araH, rhaT, xylF, xvlG, and xylH.

11. The method of claim 10 wherein araE is expressed from a constitutive promoter.

12. The method of claim 1 wherein the host cells further express a polypeptide selected from the group consisting of: cDsbA, cDshC, a protein disulfide isomerase, Ervip, a chaperone, and a transporter protein.

13. The method of claim 1 wherein the host cells comprise an expression construct comprising the polynucleotide sequence of pSOL (SEQ ID NO:3).

14. The method of claim 1 wherein the host cells comprise at least two expression constructs.

15. The method of claim 1 wherein the insulin polypeptide to be transcribed from the at least one said inducible promoter is a polypeptide that lacks a signal sequence.

16. The method of claim 1 wherein the insulin polypeptide comprises an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

17. The method of claim 1 wherein the insulin polypeptide to be transcribed from the at least one said inducible promoter further comprises a tag selected from the group consisting of: polyhistidine, pestivirus $N^{pro}$, CSFV $N^{pro}$, CSFV $N^{pro}$ (strain Alfort), BDV $N^{pro}$, BVDV $N^{pro}$, SEQ ID NO: 13, SEQ ID NO: 14, and SEQ ID NO: 15.

18. The method of claim 1 wherein the insulin polypeptide to be transcribed from the at least one said inducible promoter forms a number of disulfide bonds selected from the group consisting of: one, two, three and four disulfide bonds.

19. The method of claim 1 wherein the host cells are grown until the host cells reach a density greater than a cell density selected from the group consisting of: 150 ($OD_{600}$); 155 ($OD_{600}$); 160 ($OD_{600}$); 165 ($OD_{600}$); 170 ($OD_{600}$); and 175 ($OD_{600}$).

20. The method of claim 1, wherein the host cells are prokaryotic cells.

21. The method of claim 20, wherein the host cells are *E. coli* cells.

22. The method of claim 21, wherein the host cells are *E. coli* EB0001 cells.

23. The method of claim 1 further comprising collecting the host cells and storing them prior to lysis.

\* \* \* \* \*

SEQUENCE LISTING

<160> NUMBER OF SEQ ID NOS: 21

<210> SEQ ID NO 1
<211> LENGTH: 486
<212> TYPE: PRT
<213> ORGANISM: Artificial Sequence
<220> FEATURE:
<223> OTHER INFORMATION: Humicola insolens protein disulfide isomerase
      (PDI) amino acid sequence, without signal peptide

<400> SEQUENCE: 1

Met Ser Asp Val Val Gln Leu Lys Lys Asp Thr Phe Asp Asp Phe Ile
1               5                   10                  15

Lys Thr Asn Asp Leu Val Leu Ala Glu Phe Phe Ala Pro Trp Cys Gly
                20                  25                  30

His Cys Lys Ala Leu Ala Pro Glu Tyr Glu Ala Ala Thr Thr Leu
            35                  40                  45

Lys Glu Lys Asn Ile Lys Leu Ala Lys Val Asp Cys Thr Glu Thr
        50                  55                  60

Asp Leu Cys Gln Gln His Gly Val Glu Gly Tyr Pro Thr Leu Lys Val
65                  70                  75                  80

Phe Arg Gly Leu Asp Asn Val Ser Pro Tyr Lys Gly Gln Arg Lys Ala
                85                  90                  95

Ala Ala Ile Thr Ser Tyr Met Ile Lys Gln Ser Leu Pro Ala Val Ser
            100                 105                 110

Glu Val Thr Lys Asp Asn Leu Glu Glu Phe Lys Lys Ala Asp Lys Ala
        115                 120                 125

Val Leu Val Ala Tyr Val Asp Ala Ser Asp Lys Ala Ser Ser Glu Val
    130                 135                 140

Phe Thr Gln Val Ala Glu Lys Leu Arg Asp Asn Tyr Pro Phe Gly Ser
145                 150                 155                 160

Ser Ser Asp Ala Ala Leu Ala Glu Ala Glu Gly Val Lys Ala Pro Ala
                165                 170                 175

Ile Val Leu Tyr Lys Asp Phe Asp Glu Gly Lys Ala Val Phe Ser Glu
            180                 185                 190

Lys Phe Glu Val Glu Ala Ile Glu Lys Phe Ala Lys Thr Gly Ala Thr
        195                 200                 205

Pro Leu Ile Gly Glu Ile Gly Pro Glu Thr Tyr Ser Asp Tyr Met Ser
    210                 215                 220

```
Ala Gly Ile Pro Leu Ala Tyr Ile Phe Ala Glu Thr Ala Glu Glu Arg
225                 230                 235                 240

Lys Glu Leu Ser Asp Lys Leu Lys Pro Ile Ala Glu Ala Gln Arg Gly
            245                 250                 255

Val Ile Asn Phe Gly Thr Ile Asp Ala Lys Ala Phe Gly Ala His Ala
        260                 265                 270

Gly Asn Leu Asn Leu Lys Thr Asp Lys Phe Pro Ala Phe Ala Ile Gln
    275                 280                 285

Glu Val Ala Lys Asn Gln Lys Phe Pro Phe Asp Gln Glu Lys Glu Ile
290                 295                 300

Thr Phe Glu Ala Ile Lys Ala Phe Val Asp Asp Phe Val Ala Gly Lys
305                 310                 315                 320

Ile Glu Pro Ser Ile Lys Ser Glu Pro Ile Pro Glu Lys Gln Glu Gly
            325                 330                 335

Pro Val Thr Val Val Ala Lys Asn Tyr Asn Glu Ile Val Leu Asp
        340                 345                 350

Asp Thr Lys Asp Val Leu Ile Glu Phe Tyr Ala Pro Trp Cys Gly His
    355                 360                 365

Cys Lys Ala Leu Ala Pro Lys Tyr Glu Glu Leu Gly Ala Leu Tyr Ala
370                 375                 380

Lys Ser Glu Phe Lys Asp Arg Val Val Ile Ala Lys Val Asp Ala Thr
385                 390                 395                 400

Ala Asn Asp Val Pro Asp Glu Ile Gln Gly Phe Pro Thr Ile Lys Leu
            405                 410                 415

Tyr Pro Ala Gly Ala Lys Gly Gln Pro Val Thr Tyr Ser Gly Ser Arg
        420                 425                 430

Thr Val Glu Asp Leu Ile Lys Phe Ile Ala Glu Asn Gly Lys Tyr Lys
    435                 440                 445

Ala Ala Ile Ser Glu Asp Ala Glu Glu Thr Ser Ser Ala Thr Glu Thr
450                 455                 460

Thr Thr Glu Thr Ala Thr Lys Ser Glu Glu Ala Ala Lys Glu Thr Ala
465                 470                 475                 480

Thr Glu His Asp Glu Leu
            485

<210> SEQ ID NO 2
<211> LENGTH: 1487
<212> TYPE: DNA
<213> ORGANISM: Artificial Sequence
<220> FEATURE:
<223> OTHER INFORMATION: Protein disulfide isomerase (PDI) expression
      construct

<400> SEQUENCE: 2
gctagcagga ggaattcacc atgtctgatg ttgtacaact gaagaaagat acgttcgatg     60
actttatcaa aactaatgac ttggtgctgg cagagttttt cgccccgtgg tgtggccact    120
gcaaagctct ggctccggag tacgaagagg ccgcgaccac cctgaaagaa agaacatca    180 aactggcgaa agtggactgt acggaagaaa ccgacctgtg tcagcagcac ggcgtggaag    240
gttacccgac cctgaaggtg tttcgtggcc tggacaatgt tagcccgtac aaaggtcaac    300
gtaaggccgc agcgatcacc agctacatga tcaagcagtc gctgcctgca gtctctgagg    360
tgaccaaaga taatctggaa gagttcaaaa aggcagataa ggcggtgctg gttgcctatg    420
ttgatgcaag cgacaaggcg agcagcgagg tctttaccca ggtcgcggag aaattgcgcg    480
```

| | |
|---|---|
| ataactaccc gttcggcagc agctccgatg cagctttggc cgaggcggaa ggtgtcaagg | 540 |
| ctccggcgat cgttctgtac aaagatttcg acgagggtaa agcggtgttc agcgaaaagt | 600 |
| ttgaggtgga agcaattgaa aagttcgcaa aaaccggtgc cacgcctttg attggcgaaa | 660 |
| tcggtccgga aacctattct gactatatga gcgccggtat cccgctggcc tacattttcg | 720 |
| cagaaacggc agaagagcgc aaagaactga gcgacaagtt gaagccaatt gcagaggcac | 780 |
| agcgtggcgt catcaacttt ggtaccattg acgcgaaagc atttggtgcg catgccggta | 840 |
| acctgaatct gaaaacggac aaatttccgg cgtttgcgat tcaagaggtg gcgaagaacc | 900 |
| aaaagtttcc gttcgatcaa gaaaaagaga ttaccttcga ggcgatcaaa gcgttcgttg | 960 |
| acgactttgt tgccggtaaa atcgagccga gcattaagag cgagccgatc ccggagaagc | 1020 |
| aggaaggccc ggtgaccgtc gtcgtcgcga agaattacaa cgagattgtt ctggatgaca | 1080 |
| cgaaagacgt cctgattgag ttctatgcgc cgtggtgcgg tcattgcaaa gcgctggccc | 1140 |
| cgaaatatga agagctgggt gcgctgtacg cgaagagcga gtttaaggac cgtgtggtta | 1200 |
| tcgcgaaagt agatgcgacc gccaatgacg ttcctgacga gatccaaggc ttcccgacca | 1260 |
| ttaaactgta tccggctggt gctaaaggcc agccagttac ctatagcggt agccgcacgg | 1320 |
| ttgaggatct gattaagttc attgccgaga acggcaagta caaggcggca atcagcgagg | 1380 |
| atgcagaaga aacgagctcc gcaaccgaaa ccacgacgga aaccgctact aagtccgaag | 1440 |
| aggcggcgaa agaaaccgcg acggagcacg atgagctgta agtcgac | 1487 |

<210> SEQ ID NO 3
<211> LENGTH: 5304
<212> TYPE: DNA
<213> ORGANISM: Artificial Sequence
<220> FEATURE:
<223> OTHER INFORMATION: Dual-promoter vector, pSOL

<400> SEQUENCE: 3

| | |
|---|---|
| ggcctttctt cggtagaagt cttcccccag aggcaggtat caaaggatct tcttgagatc | 60 |
| cttttttttct gcgcgtaatc tgctgcttgc aaacaaaaaa accaccgcta ccagcggtgg | 120 |
| tttgtttgcc ggatcaagag ctaccaactc ttttttccgag gtaactggct tcagcagagc | 180 |
| gcagatacca aatactgttc ttctagtgta gccgtagtta ggccaccact tcaagaactc | 240 |
| tgtagcaccg cctacatacc tcgctctgct aatcctgtta ccagtggctg ctgccagtgg | 300 |
| cgataagtcg tgtcttaccg ggttggactc aagacgatag ttaccggata aggcgcagcg | 360 |
| gtcgggctga acggggggtt cgtgcacaca gcccagcttg gagcgaacga cctacaccga | 420 |
| actgagatac ctacagcgtg agctatgaga aagcgccacg cttcccgaag ggagaaaggc | 480 |
| ggacaggtat ccggtaagcg gcagggtcgg aacaggagag cgcacgaggg agcttccagg | 540 |
| gggaaacgcc tggtatcttt atagtcctgt cgggtttcgc cacctctgac ttgagcatcg | 600 |
| attttttgtga tgctcgtcag gggggcgag cctatggaaa aacgccagca acgcagaaag | 660 |
| gcccacccga aggtgagcca ggtgattaca tttgggccct catcagaggt tttcaccgtc | 720 |
| atcaccgaaa cgcgcgaggc agctgcggta aagctcatca gcgtggtcgt gaagcgattc | 780 |
| acagatgtct gcctgttcat ccgcgtccag ctcgttgagt ttctccagaa gcgttaatgt | 840 |
| ctggcttctg ataaagcggg ccatgttaag gcggtttttt cctgtttggg tcatacctgc | 900 |
| ttagaaaaac tcatcgagca tcaaatgaaa ttgcaattta ttcatatcag gattatcaat | 960 |
| accatatttt tgaaaagcc gtttctgtaa tgaaggagaa aactcaccga ggcagttcca | 1020 |
| taggatggca agatcctggt atcggtctgc gattccgact cgtccaacat caatacaacc | 1080 |

-continued

```
tattaatttc ccctcgtcaa aaataaggtt atcaagtgag aaatcaccat gagtgacgac    1140
tgaatccggt gagaatggca aaagtttatg catttcttc cagacttgtt caacaggcca    1200
gccattacgc tcgtcatcaa aatcactcgc atcaaccaaa ccgttattca ttcgtgattg    1260
cgcctgagcg aggcgaaata cgcgatcgct gttaaaagga caattacaaa caggaatcga    1320
gtgcaaccgg cgcaggaaca ctgccagcgc atcaacaata ttttcacctg aatcaggata    1380
ttcttctaat acctggaacg ctgttttcc ggggatcgca gtggtgagta accatgcatc    1440
atcaggagta cggataaaat gcttgatggt cggaagtggc ataaattccg tcagccagtt    1500
tagtctgacc atctcatctg taacatcatt ggcaacgcta cctttgccat gtttcagaaa    1560
caactctggc gcatcgggct tcccatacaa gcgatagatt gtcgcacctg attgcccgac    1620
attatcgcga gccatttat acccatataa atcagcatcc atgttggaat ttaatcgcgg    1680
cctcgacgtt tcccgttgaa tatggctcat agctcctgaa aatctcgata actcaaaaaa    1740
tacgcccggt agtgatctta tttcattatg gtgaaagttg gaacctctta cgtgccgatc    1800
aagaagacgg tcaaaagcct ccggtcggag gccgggagag tgttcaccga caaacaacag    1860
ataaaacaaa aggcccagtc ttccgactga gccttttgtt ttatttgatg tctggcagtt    1920
cccgagacgt tatgacaact tgacggctac atcattcact ttttcttcac aaccggcacg    1980
gaactcgctc gggctggccc cggtgcattt tttaaatacc cgcgagaaat agagttgatc    2040
gtcaaaacca acattgcgac cgacggtggc gataggcatc cgggtggtgc tcaaaagcag    2100
cttcgcctgg ctgatacgtt ggtcctcgcg ccagcttaag acgctaatcc ctaactgctg    2160
gcggaaaaga tgtgacagac gcgacggcga caagcaaaca tgctgtgcga cgctggcgat    2220
atcaaaattg ctgtctgcca ggtgatcgct gatgtactga caagcctcgc gtacccgatt    2280
atccatcggt ggatggagcg actcgttaat cgcttccatg cgccgcagta acaattgctc    2340
aagcagattt atcgccagca gctccgaata gcgcccttcc ccttgcccgg cgttaatgat    2400
ttgcccaaac aggtcgctga aatgcggctg gtgcgcttca tccgggcgaa agaacccgt    2460 attggcaaat attgacggcc agttaagcca ttcatgccag taggcgcgcg gacgaaagta    2520
aacccactgg tgataccatt cgcgagcctc cggatgacga ccgtagtgat gaatctctcc    2580
tggcgggaac agcaaaatat cacccggtcg gcaaacaaat tctcgtccct gattttcac    2640 caccccctga ccgcgaatgg tgagattgag aatataacct ttcattccca gcggtcggtc    2700
gataaaaaaa tcgagataac cgttggcctc aatcggcgtt aaacccgcca ccagatgggc    2760
attaaacgag tatcccggca gcaggggatc attttgcgct tcagccatac ttttcatact    2820
cccgccattc agagaagaaa ccaattgtcc atattgcatc agacattgcc gtctctgcgt    2880
cttttactgg ctcttctcgc taaccaaacc ggtaaccccg cttattaaaa gcattctgta    2940
acaaagcggg accaaagcca tgacaaaaac gcgtaacaaa agtgtctata atcacggcag    3000
aaaagtccac attgattatt tgcacggcgt cacactttgc tatgccatag cattttatc    3060 cataagatta gcggatccta cctgacgctt tttatcgcaa ctctctactg tttctccata    3120 cccgttttt tgggctagca ggaggtaaaa aaaatgtgag accggtctcg gtctagatcg    3180
gtcagtttca cctgatttac gtaaaaaccc gcttcggcgg gttttgctt ttggaggggc    3240 agaaagatga atgactgtct ctcctgttag tgagggttaa tgcccggaac gaagaaaggc    3300
ccacccgtga aggtgagcca gtgagttggt tacatttct cttgagggtt tagcttttca    3360
gacgacgcca aaggtcgta cgtgaaatac ccaaatagtt ggccgcagcc gtcttgtcac    3420
```

```
cattaaactt ctcaagcgct tgctgcgggg tcagcaaacg cggagccggc gtctttgcgc    3480
tctcacgcgc cagctccggc agcagcaact gcatgaattg cggagtcaga tccggggtcg    3540
gctcaacgga caggaacagc gccaggcgtt ccatcatatt acgcagctcg cggatgttac    3600
ccggccagtc ataatgcagc agcaccgttt cgctcgcctg cagaccctgg cgcagtgccg    3660
cagagaacgg tgcgctcagg gctgccagcg agactttcag gaaagactcc gccagcggta    3720
aaatgtcggc gacacgttca cgcaacgcg ggagctgcag acgcagaatg ctcaggcggt    3780
agaacaggtc gcgacgaaaa cggccctgtt gcatatcctc ttccagattg cagtgggtcg    3840
cgctaatcac gcgcacgtct accggaaccg gttgatgacc accgacgcgg gtcacttctt    3900
tctcttccag cacacgcagc agacgggttt gcaatggcag cggcatctca ccgatctcgt    3960
ccaggaacaa ggtgccgccg tgggcaattt caaacaaacc agcacggcca ccgcgacggc    4020
tacccgtgaa tgcgccctct tcgtagccaa acagctcagc ttccagcagg ctttccgcga    4080
ttgcaccgca attaactgcc acaaacggat gagatttctt accctggcgg gcatcgtgac    4140
gggcgaaata ctcacgatgg attgcttgcg cagccagttc cttacccgta ccagtctcgc    4200
cttcgatcag aacagccgcg ctgctacgtg catacagcag aatggtctgg cgaacttgct    4260
ccatttgagg gctttggccc agcatatcac ccaggacata acgggtacgc agcgcattac    4320
gcgtcgcatc gtgggtgttg tggcgcaggc tcattctggt catgtccagg gcgtcgctga    4380
acgcctgacg caccgttgcc gcgctgtaga taaagatgcc cgtcatgccc gcttcttcgg    4440
ccaagtccgt gatcagaccc gcaccaacca cagcctcggt accgttcgct ttcagttcgt    4500
tgatctggcc acgtgcatct tcctcggtaa tgtagctgcg ttggtccagg cgcagattaa    4560
aggtcttttg aaacgcgacc agcgcaggga tcgtttcctg gtaggtgaca cgccaatcg    4620 aggaggtcag tttgcctgcc ttcgccacgc cctgcaagac atcgtaaccg ctcggcttaa    4680
tcaggatcac cggcacggac agacgggatt tcaggtaggc accattgcta cccgctgcga    4740
taatggcgtc acaacgctcg ttggccagct ttttgcgaat gtaggtaacg gctttctcga    4800
aacccagctg aatcggagtg atgttcgcca ggtgatcaaa ctccaggcta atgtcgcgga    4860
acaactcgaa cagacgggtg acgctaacgg tccaaataac tggtttatca tcgttcaaac    4920
gcggtgggtg tgccatggtg aatacctcct gttaagaaac cgaatattgg gtttaaactt    4980
gtttcataat tgttgcaatg aaacgcggtg aaacattgcc tgaaacgtta actgaaacgc    5040
atatttgcgg attagttcat gactttatct ctaacaaatt gaaattaaac atttaatttt    5100
attaaggcaa ttgtggcaca ccccttgctt tgtctttatc aacgcaaata acaagttgat    5160
aacaaaagct taggaggaaa acatagagac cggtctctct cgagtaacta gttgatagag    5220
atcaagcctt aacgaactaa gacccccgca ccgaaaggtc cgggggtttt ttttgacctt    5280
aaaaacataa ccgaggagca gaca                                           5304
```

<210> SEQ ID NO 4
<211> LENGTH: 21
<212> TYPE: PRT
<213> ORGANISM: Homo sapiens

<400> SEQUENCE: 4

```
Gly Ile Val Glu Gln Cys Cys Thr Ser Ile Cys Ser Leu Tyr Gln Leu
1               5                   10                  15

Glu Asn Tyr Cys Asn
            20
```

```
<210> SEQ ID NO 5
<211> LENGTH: 30
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Insulin lispro, mature B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Insulin aspart, mature B chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Insulin glulisine, mature B chain

<400> SEQUENCE: 8

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

<210> SEQ ID NO 9
<211> LENGTH: 21
<212> TYPE: PRT
<213> ORGANISM: Artificial Sequence
<220> FEATURE:
<223> OTHER INFORMATION: Insulin glargine, mature A chain

<400> SEQUENCE: 9

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 10
```

-continued

<211> LENGTH: 32
<212> TYPE: PRT
<213> ORGANISM: Artificial Sequence
<220> FEATURE:
<223> OTHER INFORMATION: Insulin glargine, mature B chain

<400> SEQUENCE: 10

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

<210> SEQ ID NO 11
<211> LENGTH: 29
<212> TYPE: PRT
<213> ORGANISM: Artificial Sequence
<220> FEATURE:
<223> OTHER INFORMATION: Insulin degludec, mature B chain; deletion of B30 threonine and modification of lysine at B29 with a hexadecanedioic acid molecule bound to B29 through an L-gamma-Glu linker

<400> SEQUENCE: 11

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

<210> SEQ ID NO 12
<211> LENGTH: 29
<212> TYPE: PRT
<213> ORGANISM: Artificial Sequence
<220> FEATURE:
<223> OTHER INFORMATION: Insulin detemir, mature B chain; deletion of B30 threonine and modification of lysine at B29 with a myristic acid molecule

<400> SEQUENCE: 12

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25
```

<210> SEQ ID NO 13
<211> LENGTH: 168
<212> TYPE: PRT
<213> ORGANISM: Hog cholera virus (strain Alfort)

<400> SEQUENCE: 13

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110
```

```
Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 14
<211> LENGTH: 90
<212> TYPE: PRT
<213> ORGANISM: Sus scrofa

<400> SEQUENCE: 14

His Phe Glu Gly Glu Lys Val Phe Arg Val Asn Val Glu Asp Glu Asn
1               5                   10                  15

Asp Ile Ser Leu Leu His Glu Leu Ala Ser Thr Arg Gln Ile Asp Phe
            20                  25                  30

Trp Lys Pro Asp Ser Val Thr Gln Ile Lys Pro His Ser Thr Val Asp
        35                  40                  45

Phe Arg Val Lys Ala Glu Asp Ile Leu Ala Val Glu Asp Phe Leu Glu
    50                  55                  60

Gln Asn Glu Leu Gln Tyr Glu Val Leu Ile Asn Asn Leu Arg Ser Val
65                  70                  75                  80

Leu Glu Ala Gln Phe Asp Ser Arg Val Arg
                85                  90

<210> SEQ ID NO 15
<211> LENGTH: 91
<212> TYPE: PRT
<213> ORGANISM: Caenorhabditis elegans

<400> SEQUENCE: 15

Met Ala Asp Asp Ala Ala Gln Ala Gly Asp Asn Ala Glu Tyr Ile Lys
1               5                   10                  15

Ile Lys Val Val Gly Gln Asp Ser Asn Glu Val His Phe Arg Val Lys
            20                  25                  30

Tyr Gly Thr Ser Met Ala Lys Leu Lys Lys Ser Tyr Ala Asp Arg Thr
        35                  40                  45

Gly Val Ala Val Asn Ser Leu Arg Phe Leu Phe Asp Gly Arg Arg Ile
    50                  55                  60

Asn Asp Asp Asp Thr Pro Lys Thr Leu Glu Met Glu Asp Asp Asp Val
65                  70                  75                  80

Ile Glu Val Tyr Gln Glu Gln Leu Gly Gly Phe
                85                  90

<210> SEQ ID NO 16
<211> LENGTH: 189
<212> TYPE: PRT
<213> ORGANISM: Saccharomyces cerevisiae

<400> SEQUENCE: 16

Met Lys Ala Ile Asp Lys Met Thr Asp Asn Pro Pro Gln Glu Gly Leu
1               5                   10                  15

Ser Gly Arg Gly Lys Ile Ile Tyr Asp Glu Asp Gly Lys Pro Cys Arg Ser
            20                  25                  30
```

```
Cys Asn Thr Leu Leu Asp Phe Gln Tyr Val Thr Gly Lys Ile Ser Asn
             35                  40                  45
Gly Leu Lys Asn Leu Ser Ser Asn Gly Lys Leu Ala Gly Thr Gly Ala
 50                  55                  60
Leu Thr Gly Glu Ala Ser Glu Leu Met Pro Gly Ser Arg Thr Tyr Arg
 65                  70                  75                  80
Lys Val Asp Pro Pro Asp Val Glu Gln Leu Gly Arg Ser Ser Trp Thr
                 85                  90                  95
Leu Leu His Ser Val Ala Ala Ser Tyr Pro Ala Gln Pro Thr Asp Gln
                100                 105                 110
Gln Lys Gly Glu Met Lys Gln Phe Leu Asn Ile Phe Ser His Ile Tyr
            115                 120                 125
Pro Cys Asn Trp Cys Ala Lys Asp Phe Glu Lys Tyr Ile Arg Glu Asn
130                 135                 140
Ala Pro Gln Val Glu Ser Arg Glu Glu Leu Gly Arg Trp Met Cys Glu
145                 150                 155                 160
Ala His Asn Lys Val Asn Lys Lys Leu Arg Lys Pro Lys Phe Asp Cys
                165                 170                 175
Asn Phe Trp Glu Lys Arg Trp Lys Asp Gly Trp Asp Glu
            180                 185
```

<210> SEQ ID NO 17
<211> LENGTH: 570
<212> TYPE: DNA
<213> ORGANISM: Artificial Sequence
<220> FEATURE:
<223> OTHER INFORMATION: Polynucleotide encoding Erv1p, optimized for
      expression in prokaryotes such as E. coli

<400> SEQUENCE: 17

```
atgaaagcga ttgataagat gaccgataat ccaccgcaag aaggtctgag cggccgtaaa     60
atcatctacg acgaagatgg caaaccgtgt cgtagctgca acaccctgct ggactttcaa    120
tatgtgacgg gtaagatttc caatggcctg aaaaacctga gcagcaatgg caagctggcc    180
ggtacgggtg cttttgaccg tgaggcgtct gaactgatgc ctggtagccg tacgtaccgc    240
aaggttgatc cgccggacgt tgagcagctg ggtcgctcca gctggacttt gctgcatagc    300
gtcgcggcga gctacccggc acagccgacc gaccagcaaa agggtgagat gaaacagttt    360
ctgaacattt tctcgcacat ctatccgtgc aattggtgtg ccaaagactt tgaaaagtat    420
atccgtgaga atgcgccgca agtggagagc cgcgaagaac tgggccgttg gatgtgtgag    480
gcacacaaca aagtcaacaa aaagctgcgt aaaccgaagt tcgattgcaa cttctgggag    540
aagcgctgga agacggctg ggatgagtaa                                      570
```

<210> SEQ ID NO 18
<211> LENGTH: 13
<212> TYPE: PRT
<213> ORGANISM: Homo sapiens

<400> SEQUENCE: 18

```
Phe Val Asn Gln His Leu Cys Gly Ser His Leu Val Glu
 1               5                  10
```

<210> SEQ ID NO 19
<211> LENGTH: 8
<212> TYPE: PRT
<213> ORGANISM: Homo sapiens

<400> SEQUENCE: 19

```
Ala Leu Tyr Leu Val Cys Gly Glu
1               5

<210> SEQ ID NO 20
<211> LENGTH: 13
<212> TYPE: PRT
<213> ORGANISM: Homo sapiens

<400> SEQUENCE: 20

Gln Cys Cys Thr Ser Ile Cys Ser Leu Tyr Gln Leu Glu
1               5                   10

<210> SEQ ID NO 21
<211> LENGTH: 4
<212> TYPE: PRT
<213> ORGANISM: Artificial Sequence
<220> FEATURE:
<223> OTHER INFORMATION: Fragment of human insulin glargine A chain
      produced by Glu-C digest; amino acids 18-21 of SEQ ID NO:9

<400> SEQUENCE: 21

Asn Tyr Cys Gly
1
```